(12) United States Patent
Migeotte et al.

(10) Patent No.: US 7,842,795 B2
(45) Date of Patent: Nov. 30, 2010

(54) NUCLEIC ACIDS ENCODING A HEME BINDING PROTEIN POLYPEPTIDE

(75) Inventors: Isabelle Migeotte, Brussels (BE); Marc Parmentier, Beersel (BE); David Communi, Braine le Chateau (BE); Maryse Brait, Brussels (BE)

(73) Assignee: Euroscreen S.A., Brussels (BE)

( * ) Notice: Subject to any disclaimer, the term of this patent is extended or adjusted under 35 U.S.C. 154(b) by 80 days.

(21) Appl. No.: 12/075,971

(22) Filed: Mar. 13, 2008

(65) Prior Publication Data

US 2010/0009406 A1 Jan. 14, 2010

Related U.S. Application Data

(62) Division of application No. 11/129,107, filed on May 13, 2005, now Pat. No. 7,582,416.

(30) Foreign Application Priority Data

May 14, 2004 (EP) .................................. 04447122
Oct. 18, 2004 (EP) .................................. 04447231

(51) Int. Cl.
*C07H 21/04* (2006.01)
*C07K 14/00* (2006.01)
(52) U.S. Cl. ...................................... 536/23.1; 530/300
(58) Field of Classification Search ........................ None
See application file for complete search history.

(56) References Cited

FOREIGN PATENT DOCUMENTS

WO WO-01/75067 A2 10/2001

OTHER PUBLICATIONS

GenBank accession No. AF117615, *Homo sapiens* heme-binding protein (HBP) mRNA, complete cds. Jan. 28, 2000.*
Zylka et al., Discovery of a putative heme-binding protein family (SOUL/HBP) by two-tissue suppression subtractive hybridization and database searches. Brain Res. Mol. Brain Res. 74 (1-2), 175-181, 1999.*
De Yang, et al.; "Human dendritic cells express functional formyl peptide receptor-like-2 (FPRL2) throughout maturation"; Journal of Leukocyte Biology; vol. 72; No. 3; Sep. 2002; pp. 598-607.
Le Yingying et al.; "*The Role of Formyl Peptide Receptors in Microbial Infection and Inflammation*"; Current Medicinal Chemistry—Anti-Infective Agents; vol. 2; No. 1; Mar. 2003; pp. 83-93.
Thierry Christophe, et al.; "The Synthetic Peptide Trp-Lys-Tyr-Met-Val-Met-$NH_2$ Specifically Activates Neutrophils through FPRL1/Lipoxin $A_4$ Receptors and Is an Agonist for the Orphan Monocyte-expressed Chemoattractant Receptor FPRL2"; The Journal of Biological Chemistry, American Society of biological Chemists,Baltimore MD; vol. 276; No. 24; Jun. 15, 2001; pp. 21585-21593.
Shigeru Taketani, et al.; "Molecular Characterization of a Newly Identified Heme-binding Protein Induced during Differentiation of urine Erythroleukemia Cells"; The Journal of Biological Chemistry; vol. 273; No. 47; Nov. 20, 1998; pp. 31388-31394.
B. Jacob Bklackmon, et al.; "*Characterization of a human and mouse tetrapyrrole-binding protein*"; Archives of Biochemistry and Biophysics; vol. 407; No. 2; Nov. 15, 2002; pp. 196-201.
Isabelle Migeotte, et al.; "*Identification and characterization of an endogenous chemotactic ligand specific for FPRL2*"; Journal of Experimental Medicine; vol. 201; No. 1; Jan. 3, 2005; pp. 83-93.
S. Costagliola, et al.; "Genetic Immunization Against the Human Thyrotropin Receptor Causes Thyroiditis and Allows Production of Monoclonal Antibodies Recognizing the Native Receptor"; Journal of Immunology; vol. 160, No. 3; Feb. 1, 1998; pp. 1458-1465.
Asa Betten, et al.; "A proinflammatory peptide from *Helicobacter pylori* activates monocytes to induce lymphocyte dysfunction and apoptois"; The Journal of Clinical Investigation; vol. 108; No. 8; Oct. 2001; pp. 1221-1228.
MichaelC. Braun, et al.; "Activation of the formyl peptide receptor by the HIV-derived peptide T-20 suppresses interleukin-12 p70 production by human monocytes"; Blood; vol. 97; No. 11; Jun. 1, 2001; pp. 3531-3536.
Philip M. Murphy, et al.; "A Structural Homologue of the N-Formyl Peptide Receptor Characterization and Chromosome Mapping of a Peptide Chemoattractant Receptor Family"; The Journal of Biological Chemistry; vol. 267, No. 11; Apr. 15, 1992; pp. 7637-7643.
T. Gudermann, et al.; "Receptors and G proteins as primary components of transmembrane signal transduction"; J. Mol. Med.; 1995; vol. 73; pp. 51-63.
Francois Boulay, et al.; "The Human N-Formylpeptide receptor. Characterization of Two cDNA Isolates and Evidence for a New Subfamily of G-Protein-Coupled Receptors"; Biochemistry; 1990; vol. 29; pp. 11123-11133.
Richard D. Ye, et al.; "*Isolation of a cDMA That Encodes a Novel Granulocyte N0-Formyl Peptide Receptor*"; Biochemical and Biophysical Research Communications; vol. 184; No. 2; Apr. 30, 1992; pp. 582-589.
Francois Boulay, et al.; "*Synthesis and Use of a Novel N-Formyl Peptide Derivative to Isolate a Human N-Formyl Peptide receptor cDNA*"; Biochemical and Biophysical Research Communications; vol. 168; No. 3; May 16, 1990; pp. 1103-1109.

* cited by examiner

*Primary Examiner*—Ruixiang Li
(74) *Attorney, Agent, or Firm*—Edwards Angell Palmer & Dodge LLP; Kathleen Williams; Amy DeCloux

(57) ABSTRACT

The present invention relates to methods, reagents and kits for detecting of formyl peptide receptor like-2 (FPRL2) polypeptide activity in a sample and identifying agents which modulate polypeptide activity. It further relates to antibodies raised against FPRL2. It further relates to substances for preventing, treating and/or alleviating diseases or disorders characterized by dysregulation of FPRL2 polypeptide signalling.

1 Claim, 23 Drawing Sheets

```
                                                          gaattcacc
  1 ATG GAA ACC AAC TTC TCC ATT CCT CTG AAT GAA ACT GAG GAG GTG   45
  1  M   E   T   N   F   S   I   P   L   N   E   T   E   E   V   15

46 CTC CCT GAG CCT GCT GGC CAC ACC GTT CTG TGG ATC TTC TCA TTG   90
 16  L   P   E   P   A   G   H   T   V   L   W   I   F   S   L   30

91 CTA GTC CAC GGA GTC ACC TTT GTC TTC GGG GTC CTG GGC AAT GGG  135
 31  L   V   H   G   V   T   F   V   F   G   V   L   G   N   G   45

136 CTT GTG ATC TGG GTG GCT GGA TTC CGG ATG ACA CGC ACA GTC AAC  180
 46  L   V   I   W   V   A   G   F   R   M   T   R   T   V   N   60

181 ACC ATC TGT TAC CTG AAC CTG GCC CTA GCT GAC TTC TCT TTC AGT  225
 61  T   I   C   Y   L   N   L   A   L   A   D   F   S   F   S   75

226 GCC ATC CTA CCA TTC CGA ATG GTC TCA GTC GCC ATG AGA GAA AAA  270
 76  A   I   L   P   F   R   M   V   S   V   A   M   R   E   K   90

271 TGG CCT TTT GGC TCA TTC CTA TGT AAG TTA GTT CAT GTT ATG ATA  315
 91  W   P   F   G   S   F   L   C   K   L   V   H   V   M   I  105

316 GAC ATC AAC CTG TTT GTC AGT GTC TAC CTG ATC ACC ATC ATT GCT  360
106  D   I   N   L   F   V   S   V   Y   L   I   T   I   I   A  120

361 CTG GAC CGC TGT ATT TGT GTC CTG CAT CCA GCC TGG GCC CAG AAC  405
121  L   D   R   C   I   C   V   L   H   P   A   W   A   Q   N  135

406 CAT CGC ACC ATG AGT CTG GCC AAG AGG GTG ATG ACG GGA CTC TGG  450
136  H   R   T   M   S   L   A   K   R   V   M   T   G   L   W  150

451 ATT TTC ACC ATA GTC CTT ACC TTA CCA AAT TTC ATC TTC TGG ACT  495
151  I   F   T   I   V   L   T   L   P   N   F   I   F   W   T  165

496 ACA ATA AGT ACT ACG AAT GGG GAC ACA TAC TGT ATT TTC AAC TTT  540
166  T   I   S   T   T   N   G   D   T   Y   C   I   F   N   F  180

541 GCA TTC TGG GGT GAC ACT GCT GTA GAG AGG TTG AAC GTG TTC ATT  585
181  A   F   W   G   D   T   A   V   E   R   L   N   V   F   I  195

586 ACC ATG GCC AAG GTC TTT CTG ATC CTC CAC TTC ATT ATT GGC TTC  630
196  T   M   A   K   V   F   L   I   L   H   F   I   I   G   F  210

631 AGC GTG CCT ATG TCC ATC ATC ACA GTC TGC TAT GGG ATC ATC GCT  675
211  S   V   P   M   S   I   I   T   V   C   Y   G   I   I   A  225

676 GCC AAA ATT CAC AGA AAC CAC ATG ATT AAA TCC AGC CGT CCC TTA  720
226  A   K   I   H   R   N   H   M   I   K   S   S   R   P   L  240

721 CGT GTC TTC GCT GCT GTG GTG GCT TCT TTC TTC ATC TGT TGG TTC  765
241  R   V   F   A   A   V   V   A   S   F   F   I   C   W   F  255

766 CCT TAT GAA CTA ATT GGC ATT CTA ATG GCA GTC TGG CTC AAA GAG  810
256  P   Y   E   L   I   G   I   L   M   A   V   W   L   K   E  270
```

FIGURE 1

```
 811 ATG TTG TTA AAT GGC AAA TAC AAA ATC ATT CTT GTC CTG ATT AAC  855
 271  M   L   L   N   G   K   Y   K   I   I   L   V   L   I   N  285

856 CCA ACA AGC TCC TTG GCC TTT TTT AAC AGC TGC CTC AAC CCA ATT  900
 286  P   T   S   S   L   A   F   F   N   S   C   L   N   P   I  300

901 CTC TAC GTC TTT ATG GGT CGT AAC TTC CAA GAA AGA CTG ATT CGC  945
 301  L   Y   V   F   M   G   R   N   F   Q   E   R   L   I   R  315

946 TCT TTG CCC ACT AGT TTG GAG AGG GCC CTG ACT GAG GTC CCT GAC  990
 316  S   L   P   T   S   L   E   R   A   L   T   E   V   P   D  330

991 TCA GCC CAG ACC AGC AAC ACA GAC ACC ACT TCT GCT TCA CCT CCT 1035
 331  S   A   Q   T   S   N   T   D   T   T   S   A   S   P   P  345

1036 GAG GAG ACG GAG TTA CAA GCA ATG TGA ggtcggggatattttggggctct 1062
 346  E   E   T   E   L   Q   A   M   *                          354 gtctctttctaccctgcgttctaga
                         XbaI
```

FIGURE 1 (CONTINUED)

Acetyl-MLGMIKNSLFGSVETWPWQVL

<SEQ ID N°1(DNA human FPRL2);DNA;->
ATGGAAACCAACTTCTCCATTCCTCTGAATGAAACTGAGGAGGTGCTCCCTGAGCCTGC
TGGCCACACCGTTCTGTGGATCTTCTCATTGCTAGTCCACGGAGTCACCTTTGTCTTCG
GGGTCCTGGGCAATGGGCTTGTGATCTGGGTGGCTGGATTCCGGATGACACGCACAGTC
AACACCATCTGTTACCTGAACCTGGCCCTAGCTGACTTCTCTTTCAGTGCCATCCTACC
ATTCCGAATGGTCTCAGTCGCCATGAGAGAAAAATGGCCTTTTGGCTCATTCCTATGTA
AGTTAGTTCATGTTATGATAGACATCAACCTGTTTGTCAGTGTCTACCTGATCACCATC
ATTGCTCTGGACCGCTGTATTTGTGTCCTGCATCCAGCCTGGGCCCAGAACCATCGCAC
CATGAGTCTGGCCAAGAGGGTGATGACGGGACTCTGGATTTTCACCATAGTCCTTACCT
TACCAAATTTCATCTTCTGGACTACAATAAGTACTACGAATGGGGACACATACTGTATT
TTCAACTTTGCATTCTGGGGTGACACTGCTGTAGAGAGGTTGAACGTGTTCATTACCAT
GGCCAAGGTCTTTCTGATCCTCCACTTCATTATTGGCTTCAGCGTGCCTATGTCCATCA
TCACAGTCTGCTATGGGATCATCGCTGCCAAAATTCACAGAAACCACATGATTAAATCC
AGCCGTCCCTTACGTGTCTTCGCTGCTGTGGTGGCTTCTTTCTTCATCTGTTGGTTCCC
TTATGAACTAATTGGCATTCTAATGGCAGTCTGGCTCAAAGAGATGTTGTTAAATGGCA
AATACAAAATCATTCTTGTCCTGATTAACCCAACAAGCTCCTTGGCCTTTTTTAACAGC
TGCCTCAACCCAATTCTCTACGTCTTTATGGGTCGTAACTTCCAAGAAAGACTGATTCG
CTCTTTGCCCACTAGTTTGGAGAGGGCCCTGACTGAGGTCCCTGACTCAGCCCAGACCA
GCAACACAGACACCACTTCTGCTTCACCTCCTGAGGAGACGGAGTTACAAGCAATGTGA <SEQ ID N°2: (human FPRL2);PRT;->
METNFSIPLNETEEVLPEPAGHTVLWIFSLLVHGVTFVFGVLGNGLVIWVAGFRMTRTV
NTICYLNLALADFSFSAILPFRMVSVAMREKWPFGSFLCKLVHVMIDINLFVSVYLITI
IALDRCICVLHPAWAQNHRTMSLAKRVMTGLWIFTIVLTLPNFIFWTTISTTNGDTYCI
FNFAFWGDTAVERLNVFITMAKVFLILHFIIGFSVPMSIITVCYGIIAAKIHRNHMIKS
SRPLRVFAAVVASFFICWFPYELIGILMAVWLKEMLLNGKYKIILVLINPTSSLAFFNS
CLNPILYVFMGRNFQERLIRSLPTSLERALTEVPDSAQTSNTDTTSASPPEETELQAM

FIGURE 8-1

<SEQ ID N°3: (DNA human FPR);DNA;->
ATGGAGACAAATTCCTCTCTCCCCACGAACATCTCTGGAGGGACACCTGCTGTATCTGC
TGGCTATCTCTTCCTGGATATCATCACTTATCTGGTATTTGCAGTCACCTTTGTCCTCG
GGGTCCTGGGCAACGGGCTTGTGATCTGGGTGGCTGGATTCCGGATGACACACACAGTC
ACCACCATCAGTTACCTGAACCTGGCCGTGGCTGACTTCTGTTTCACCTCCACTTTGCC
ATTCTTCATGGTCAGGAAGGCCATGGGAGGACATTGGCCTTTCGGCTGGTTCCTGTGCA
AATTCCTCTTTACCATAGTGGACATCAACTTGTTCGGAAGTGTCTTCCTGATCGCCCTC
ATTGCTCTGGACCGCTGTGTTTGCGTCCTGCATCCAGTCTGGACCCAGAACCACCGCAC
CGTGAGCCTGGCCAAGAAGGTGATCATTGGGCCCTGGGTGATGGCTCTGCTCCTCACAT
TGCCAGTTATCATTCGTGTGACTACAGTACCTGGTAAAACGGGGACAGTAGCCTGCACT
TTTAACTTTTCGCCCTGGACCAACGACCCTAAAGAGAGGATAAATGTGGCCGTTGCCAT
GTTGACGGTGAGAGGCATCATCCGGTTCATCATTGGCTTCAGCGCACCCATGTCCATCG
TTGCTGTCAGTTATGGGCTTATTGCCACCAAGATCCACAAGCAAGGCTTGATTAAGTCC
AGTCGTCCCTTACGGGTCCTCTCCTTTGTCGCAGCAGCCTTTTTTCTCTGCTGGTCCCC
ATATCAGGTGGTGGCCCTTATAGCCACAGTCAGAATCCGTGAGTTATTGCAAGGCATGT
ACAAAGAAATTGGTATTGCAGTGGATGTGACAAGTGCCCTGGCCTTCTTCAACAGCTGC
CTCAACCCCATGCTCTATGTCTTCATGGGCCAGGACTTCCGGGAGAGGCTGATCCACGC
CCTTCCCGCCAGTCTGGAGAGGGCCCTGACCGAGGACTCAACCCAAACCAGTGACACAG
CTACCAATTCTACTTTACCTTCTGCAGAGGTGGCGTTACAGGCAAAGTGA <SEQ ID N°4: (human FPR) ;PRT;->
METNSSLPTNISGGTPAVSAGYLFLDIITYLVFAVTFVLGVLGNGLVIWVAGFRMTHTV
TTISYLNLAVADFCFTSTLPFFMVRKAMGGHWPFGWFLCKFLFTIVDINLFGSVFLIAL
IALDRCVCVLHPVWTQNHRTVSLAKKVIIGPWVMALLLTLPVIIRVTTVPGKTGTVACT
FNFSPWTNDPKERINVAVAMLTVRGIIRFIIGFSAPMSIVAVSYGLIATKIHKQGLIKS
SRPLRVLSFVAAAFFLCWSPYQVVALIATVRIRELLQGMYKEIGIAVDVTSALAFFNSC
LNPMLYVFMGQDFRERLIHALPASLERALTEDSTQTSDTATNSTLPSAEVALQAK

FIGURE 8-2

<SEQ ID N°5: (DNA human FPRL1) ;DNA;->
ATGGAAACCAACTTCTCCACTCCTCTGAATGAATATGAAGAAGTGTCCTATGAGTCTGC
TGGCTACACTGTTCTGCGGATCCTCCCATTGGTGGTGCTTGGGGTCACCTTTGTCCTCG
GGGTCCTGGGCAATGGGCTTGTGATCTGGGTGGCTGGATTCCGGATGACACGCACAGTC
ACCACCATCTGTTACCTGAACCTGGCCCTGGCTGACTTTTCTTTCACGGCCACATTACC
ATTCCTCATTGTCTCCATGGCCATGGGAGAAAAATGGCCTTTTGGCTGGTTCCTGTGTA
AGTTAATTCACATCGTGGTGGACATCAACCTCTTTGGAAGTGTCTTCTTGATTGGTTTC
ATTGCACTGGACCGCTGCATTTGTGTCCTGCATCCAGTCTGGGCCCAGAACCACCGCAC
TGTGAGTCTGGCCATGAAGGTGATCGTCGGACCTTGGATTCTTGCTCTAGTCCTTACCT
TGCCAGTTTTCCTCTTTTTGACTACAGTAACTATTCCAAATGGGGACACATACTGTACT
TTCAACTTTGCATCCTGGGGTGGCACCCCTGAGGAGAGGCTGAAGGTGGCCATTACCAT
GCTGACAGCCAGAGGGATTATCCGGTTTGTCATTGGCTTTAGCTTGCCGATGTCCATTG
TTGCCATCTGCTATGGGCTCATTGCAGCCAAGATCCACAAAAAGGGCATGATTAAATCC
AGCCGTCCCTTACGGGTCCTCACTGCTGTGGTGGCTTCTTTCTTCATCTGTTGGTTTCC
CTTTCAACTGGTTGCCCTTCTGGGCACCGTCTGGCTCAAAGAGATGTTGTTCTATGGCA
AGTACAAAATCATTGACATCCTGGTTAACCCAACGAGCTCCCTGGCCTTCTTCAACAGC
TGCCTCAACCCCATGCTTTACGTCTTTGTGGGCCAAGACTTCCGAGAGAGACTGATCCA
CTCCCTGCCCACCAGTCTGGAGAGGGCCCTGTCTGAGGACTCAGCCCCAACTAATGACA
CGGCTGCCAATTCTGCTTCACCTCCTGCAGAGACTGAGTTACAGGCAATGTGA <SEQ ID N°6: (human FPRL1) ;PRT;->

METNFSTPLNEYEEVSYESAGYTVLRILPLVVLGVTFVLGVLGNGLVIWVAGFRMTRTV
TTICYLNLALADFSFTATLPFLIVSMAMGEKWPFGWFLCKLIHIVVDINLFGSVFLIGF
IALDRCICVLHPVWAQNHRTVSLAMKVIVGPWILALVLTLPVFLFLTTVTIPNGDTYCT
FNFASWGGTPEERLKVAITMLTARGIIRFVIGFSLPMSIVAICYGLIAAKIHKKGMIKS
SRPLRVLTAVVASFFICWFPFQLVALLGTVWLKEMLFYGKYKIIDILVNPTSSLAFFNS
CLNPMLYVFVGQDFRERLIHSLPTSLERALSEDSAPTNDTAANSASPPAETELQAM

FIGURE 8-3

<SEQ ID N°7:(DNA human HBP sequence) ;DNA;->

ATGTTGGGCATGATCAAGAACTCGCTGTTCGGAAGCGTAGAGACGTGGCCTTGGCAGGT
CCTAAGCAAAGGGGACAAGGAAGAAGTTGCCTATGAAGAAAGGGCCTGTGAAGGCGGCA
AATTTGCCACAGTAGAAGTGACAGATAAGCCTGTGGATGAGGCTCTACGGGAAGCAATG
CCCAAGGTCGCAAAGTATGCGGGGGGCACCAATGACAAGGGAATTGGGATGGGGATGAC
AGTCCCTATTTCCTTTGCTGTGTTCCCCAATGAAGATGGCTCTCTGCAGAAGAAATTAA
AAGTCTGGTTCCGGATTCCAAACCAATTTCAAAGCGACCCACCAGCTCCCAGTGACAAA
AGCGTTAAGATTGAGGAACGGGAAGGCATCACTGTCTATTCCATGCAGTTTGGTGGTTA
TGCCAAGGAAGCAGACTACGTAGCACAAGCCACCCGTCTGCGTGCTGCCCTGGAGGGCA
CAGCCACCTACCGGGGGGACATCTACTTCTGCACGGGTTATGACCCTCCCATGAAGCCC
TACGGACGGCGCAATGAGATCTGGCTGTTGAAGACATGA

<SEQ ID N°8:(human HBP sequence, 189 residues) ;PRT;->

MLGMIKNSLFGSVETWPWQVLSKGDKEEVAYEERACEGGKFATVEVTDKPVDEALREAM
PKVAKYAGGTNDKGIGMGMTVPISFAVFPNEDGSLQKKLKVWFRIPNQFQSDPPAPSDK
SVKIEEREGITVYSMQFGGYAKEADYVAQATRLRAALEGTATYRGDIYFCTGYDPPMKP
YGRRNEIWLLKT

<SEQ ID N°9: (DNA mouse HBP sequence) ;DNA;->

ATGTTGGGCATGATCAGGAACTCACTGTTCGGGAGCGTGGAAACGTGGCCTTGGCAGGT
TCTAAGCACCGGGGGCAAGGAAGATGTCTCCTATGAGGAAAGAGCCTGTGAAGGGGGCA
AGTTTGCTACTGTGGAAGTGACAGACAAGCCAGTGGATGAGGCTCTCCGGGAAGCGATG
CCCAAGATCATGAAGTATGTGGGTGGCACCAATGACAAAGGAGTCGGCATGGGTATGAC
AGTCCCTGTCTCTTTTGCCGTGTTTCCCAATGAAGATGGCTCCCTACAGAAGAAACTGA
AAGTCTGGTTCCGGATTCCGAACCAATTTCAAGGCAGCCCACCGGCCCCCAGTGATGAG
AGTGTGAAGATCGAGGAACGGGAGGGCATCACTGTCTATTCCACGCAATTTGGAGGCTA
TGCCAAGGAAGCAGACTATGTTGCTCATGCCACCCAGCTACGGACCACACTGGAGGGCA
CACCAGCGACCTACCAGGGTGATGTCTATTACTGTGCCGGATATGACCCTCCCATGAAG
CCCTATGGACGCCGTAACGAGGTCTGGCTTGTGAAGGCATGA

<SEQ ID N°10: (mouse HBP sequence, 190) ;PRT;->
MLGMIRNSLFGSVETWPWQVLSTGGKEDVSYEERACEGGKFATVEVTDKPVDEALREAM
PKIMKYVGGTNDKGVGMGMTVPVSFAVFPNEDGSLQKKLKVWFRIPNQFQGSPPAPSDE
SVKIEEREGITVYSTQFGGYAKEADYVAHATQLRTTLEGTPATYQGDVYYCAGYDPPMK
PYGRRNEVWLVKA

FIGURE 8-4

<SEQ ID N°11;PRT;->
Ac-FKKSFKL-NH2

<SEQ ID N°12;PRT;->
RRLIEDAEYAARG

<SEQ ID N°13;DNA;->
GGGGACTTTCC

<SEQ ID N°14;DNA;->
ACCGGAATTCACCATGGAAACCAACTTCTCC

<SEQ ID N°15;DNA;->
ATCATCTAGAACGCAGGGTAGAAAGAGACAG

<SEQ ID N°16;DNA;->
CGCACAGTCAACACCATCTG

<SEQ ID N°17;DNA;->
AGCTGTTAAAAAAGGCCAAG

<SEQ ID N°18 (a HBP polypeptide);PRT;->
Acetyl-MLGMIKNSLFGSVETWPWQVL

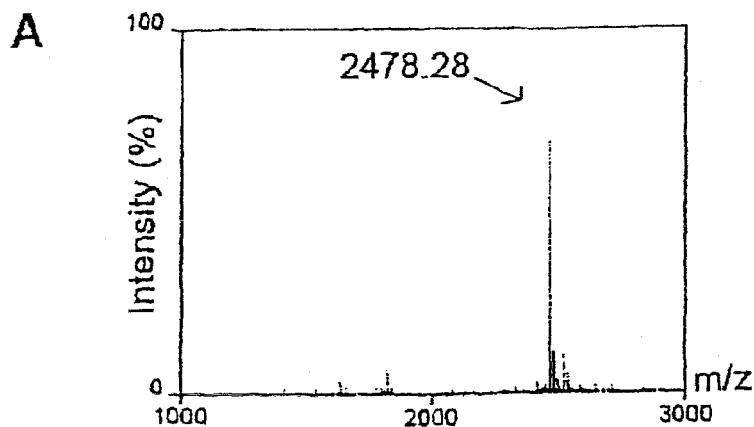

B

|  |  | Monoisotopic mass (dalton) | Sequence |
|---|---|---|---|
| Activity 1 | Tryptic fragments | 1978.03 | NSLFGSVETWPWQVLSK |
|  |  | 1821.92 | FATVEMTDKEVDEALR |
| Activity 2 | Intact mass | 2478.28 | Ac-MLGMIKNSLFGSVETWPWQVL |
|  | Tryptic fragment | 1762.94 | NSLFGSVETWPWQVL |

C

```
Human    MLGMIKNSLFGSVETWPWQVLSKGDKEEVAYEERACEGGKFATVEVT
Mouse    MLGMIRNSLFGSVETWPWQVLSTGGKEDVSYEERACEGGKFATVEVT
Pig      MLGMIKNSLFGSVETWPWQVLSKGDKQDISYEERACEGGKFATVEMT Human    DKPVDEALREAMPKVAKYAGGTNDKGIGMGMTVPISFAVFPNEDGS
Mouse    DKPVDEALREAMPKIMKYVGGTNDKGVGMGMTVPVSFAVFPNEDGS
Pig      DKPVDEALREAMPKVMKYVGGSNDKGIGMGMTVPISFAVFPSDGGS Human    LQKKLKVWFRIPNQFQSDPPAPSDKSVKIEEREGITVYSMQFGGYAKE
Mouse    LQKKLKVWFRIPNQFQGSPPAPSDESVKIEEREGITVYSTQFGGYAKE
Pig      LQKKLKVWFRIPNEFQSNPPVPSDDSIKIEERESITVYSLQFGGYAKE Human    ADYVAQATRLRAALEGT ATYRGDIYFCTGYDPPMKPYGRRNEIWLLKT
Mouse    ADYVAHATQLRTTLEGTPATYQGDVYYCAGYDPPMKPYGRRNEVWLVKA
Pig      ADYVARAAQLRTALEGI ATCRSDVYFCTGYDPPMKPYGRRNEVWLVKA
```

FIGURE 10

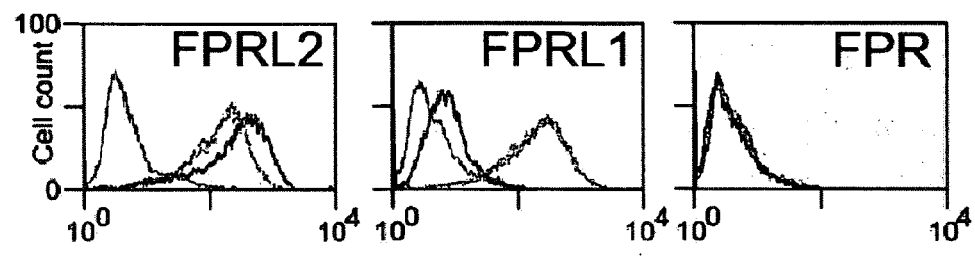
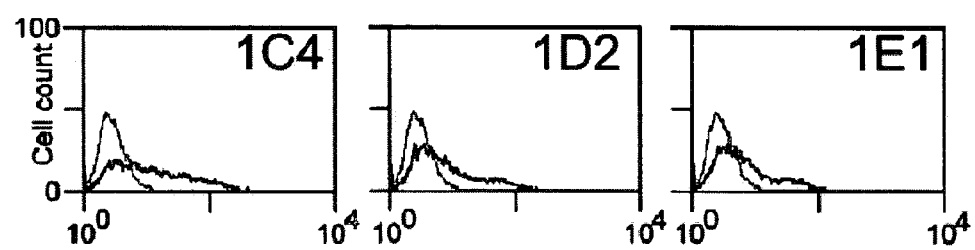
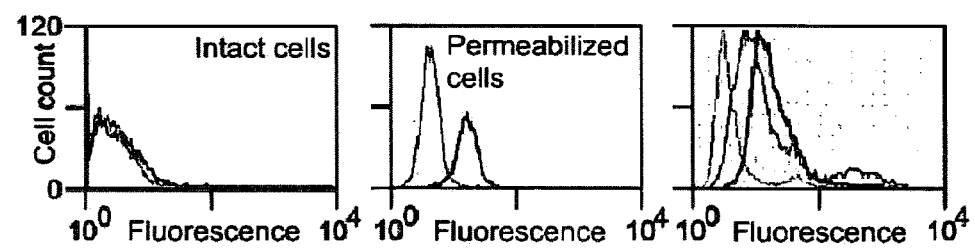
FIGURE 12

NUCLEIC ACIDS ENCODING A HEME BINDING PROTEIN POLYPEPTIDE

RELATED APPLICATION(S)

This is a divisional patent application of U.S. patent application Ser. No. 11/129,107, filed May 13, 2005 issued as U.S. Pat. No. 7,582,416 B2, which claims the benefit of European Patent Application 04447122.5, filed May 14, 2004 and European Patent Application 04447231.4, filed Oct. 18, 2004. The entire teachings of the above application(s) are incorporated herein by reference.

FIELD OF THE INVENTION

The present invention is related to the natural ligand for an orphan G protein coupled receptor FPRL2 and methods of use. It further relates to antibodies raised against FPRL2.

BACKGROUND

G-protein coupled receptors (GPCRs) are proteins responsible for transducing a signal within a cell. GPCRs have usually seven transmembrane domains. Upon binding of a ligand to an extra-cellular portion or fragment of a GPCR, a signal is transduced within the cell that results in a change in a biological or physiological property or behaviour of the cell. GPCRs, along with G-proteins and effectors (intracellular enzymes and channels modulated by G-proteins), are the components of a modular signalling system that connects the state of intra-cellular second messengers to extra-cellular inputs.

GPCR genes and gene products can modulate various physiological processes and are potential causative agents of disease. The GPCRs seem to be of critical importance to both the central nervous system and peripheral physiological processes.

The GPCR protein superfamily is represented by five families: Family I, receptors typified by rhodopsin and the beta2-adrenergic receptor and currently represented by over 200 unique members; Family II, the parathyroid hormone/calcitonin/secretin receptor family; Family III, the metabotropic glutamate receptor family, Family IV, the CAMP receptor family, important in the chemotaxis and development of *D. discoideum*; and Family V, the fungal mating pheromone receptor such as STE2.

G proteins represent a family of heterotrimeric proteins composed of α, β and γ subunits, that bind guanine nucleotides. These proteins are usually linked to cell surface receptors (receptors containing seven transmembrane domains) for signal transduction. Indeed, following ligand binding to the GPCR, a conformational change is transmitted to the G protein, which causes the α-subunit to exchange a bound GDP molecule for a GTP molecule and to dissociate from the βγ-subunits.

The GTP-bound form of the α, β and γ-subunits typically functions as an effector-modulating moiety, leading to the production of second messengers, such as cAMP (e.g. by activation of adenyl cyclase), diacylglycerol or inositol phosphates.

More than 20 different types of α-subunits are known in humans. These subunits associate with a small pool of β and γ subunits. Examples of mammalian G proteins include Gi, Go, Gq, Gs and Gt. G proteins are described extensively in Lodish et al., *Molecular Cell Biology* (Scientific American Books Inc., New York, N.Y., 1995; and also by Downes and Gautam, 1999, The G-Protein Subunit Gene Families.

*Genomics* 62:544-552), the contents of both of which are incorporated herein by reference.

Known and uncharacterized GPCRs currently constitute major targets for drug action and development. There are ongoing efforts to identify new G protein coupled receptors which can be used to screen for new agonists and antagonists having potential prophylactic and therapeutic properties.

More than 300 GPCRs have been cloned to date, excluding the family of olfactory receptors. Mechanistically, approximately 50-60% of all clinically relevant drugs act by modulating the functions of various GPCRs (Cudermann et al., *J. Mol. Med.*, 73:51-63, 1995).

Formyl peptide receptor-like 2 (FPRL2) (SEQ ID NO: 1, human polynucleotide sequence, SEQ ID NO: 2, human amino acid sequence) is a member of FPR Family. The members of this family belong to the GPCR family. Human FPR (SEQ ID NO: 3, human polynucleotide sequence, SEQ ID NO: 4, human amino acid sequence) was first member of the FRP family defined biochemically, in 1976, as a high affinity binding site on the surface of neutrophils for the prototypic N-formyl peptide formyl-methionine-leucyl-phenylalanine (fMLF). It was then cloned in 1990, by Boulay et al. from a differentiated HL-60 myeloid leukemia-cell cDNA library [Boulay, F. et al. (1990) Biochem. Biophys. Res. Commun. 168, 1103-1109; Boulay, F. et al. (1990) Biochemistry 29, 11123-11133]. In transfected cell lines, FPR binds fMLF with high affinity ($K_d$<1 nM) and is activated by picomolar to low nanomolar concentrations of fMLF in chemotaxis and calcium ion ($Ca^{2+}$) mobilization assays.

Two additional human genes, designated FPRL1 (FPR-like 1) (SEQ ID NO: 5, human polynucleotide sequence; SEQ ID NO: 6, human amino acid sequence) and FPRL2 (FPR-like 2), were subsequently isolated by low-stringency hybridization using FPR cDNA as a probe [Ye, R. D. et al. (1992) Biochem. Biophys. Res. Commun. 184, 582-589; Bao, L. et al. (1992) Genomics 13, 437-440] and shown to cluster with FPR on human chromosome 19q13.3 [Murphy, P. M. et al. (1992) J. Biol. Chem. 267, 7637-7643 ; Bao, L. et al. (1992) Genomics 13, 437-440]. FPRL1 is defined as a low-affinity fMLF receptor, based on its activation only by high concentrations of Fmlf (µM range) in vitro [Murphy, P. M. (1996) Chemoattractant Ligands and their Receptors (Horuk R, ed.), pp. 269-299, CRC Press, Inc., Boca Raton; Prossnitz, E. R. and Ye, R. D. (1997) Pharmacol. Ther. 74, 73-102]. However, it is unclear whether such concentrations of fMLF could be generated at sites of bacterial infection or tissue injury. Therefore, the role of FPRL1 as another bonafide functional fMLF receptor in vivo remains to be determined. FPRL2 does not bind or respond to N-formyl peptides [Durstin, M. et al. (1994) Biochem. Biophys. Res. Commun. 201, 174-179] but instead shares some non-formylated chemotactic peptides identified for FPRL1 [Christophe, T. et al. (2001) J. Biol. Chem. 276, 21585-21593; Betten, A. et al. (2001) J. Clin. Invest. 108, 1221-1228].

Although FPR and FPRL1 were initially detected in phagocytic leukocytes, other cell types also express these receptors but with undefined biological significance. Little information is available about the expression pattern of FPRL2, except that mRNA for this receptor is present in monocytes but not neutrophils [Durstin, M. et al. (1994) Biochem. Biophys. Res. Commun. 201, 174-179]. Functional FPRL2 is also expressed in mature dentritic cells (DCs) [Yang, D. et al. J. Leukoc. Biol. Vol. 72: 598-607 (2002)], which express reduced levels of FPR but do not appear to express FPRL1 [Yang, D. et al. (2001) J. Immunol. 166, 4092-4098 ; Braun, M. C. et al. (2001) Blood 97, 3531-3536].

The Heme Binding Protein (HBP) (Sequence ID NO 7: human polynucleotide sequence, Sequence ID NO 8: human amino acid sequence; Sequence ID NO 9: mouse polynucleotide sequence, Sequence ID NO 10: mouse amino acid sequence). The human and mouse HBP cDNAs are 567 and 570bp long respectively and encode a protein product of 189 and 190 amino acids respectively. This protein is located into the cytoplasm of the cell. HPB binds heme and porphyrins with micromolar Kd. HBP may function as a buffer for overproduced porphyrin as well as heme. Expression studies indicated that the mouse mRNA encoding HBP is expressed in liver, spleen and kidney cells (Blackmon et al; 2002 Arch. of Bichem. and Biophysics 407, p196-201).

SUMMARY OF THE INVENTION

One embodiment of the present invention is a method for detecting FPRL2 polypeptide activity in a sample comprising the steps of:
 a) incubating a sample comprising FPRL2 polypeptide with HBP polypeptide under conditions which permit binding of FPRL2 polypeptide and HBP polypeptide, and
 b) detecting a second messenger.

Another embodiment of the present invention is a method as described above further comprising the steps of:
 a) incubating a second sample comprising FPRL2 polypeptide in the absence of HBP polypeptide under conditions which permit binding of FPRL2 polypeptide and HBP polypeptide, and
 b) detecting a second messenger.

Another embodiment of the present invention is a method as described above wherein said sample comprises cells expressing FPRL2 polypeptide.

Another embodiment of the present invention is a method as described above wherein said sample comprises cell membranes bearing FPRL2 polypeptide.

Another embodiment of the present invention is a method as described above wherein said incubating is performed in or on virus-induced budding membranes containing a FPRL2 polypeptide polypeptide.

Another embodiment of the present invention is a method as described above, wherein step a) is further performed in the presence of Gα16 polypeptide.

Another embodiment of the present invention is a method of identifying an agent that binds to FPRL2 polypeptide, said method comprising:
 (a) contacting a FPRL2 polypeptide with HBP polypeptide in the presence or absence of a candidate binding agent under conditions permitting binding of said HBP polypeptide to said FPRL2 polypeptide; and
 (b) measuring binding of said FPRL2 polypeptide to said HBP polypeptide, wherein a decrease in binding in the presence of said candidate binding agent, relative to binding in the absence of said candidate binding agent, identifies said candidate binding agent as an agent that binds to FPRL2 polypeptide.

Another embodiment of the present invention is a method as described above, wherein said agent is present in a sample.

Another embodiment of the present invention is a method of identifying an agent that increases the signaling activity of FPRL2 polypeptide, said method comprising:
 (a) contacting a FPRL2 polypeptide with an agent;
 (b) measuring a signaling activity of said FPRL2 polypeptide in the presence of said agent; and
 (c) comparing said activity measured in the presence of said agent to said activity measured in a reaction in which said FPRL2 polypeptide is contacted with HBP polypeptide, wherein said agent is identified as an agonist that increases the signaling of said FPRL2 polypeptide when the amount of said activity measured in the presence of said agent is at least 10% of the amount induced by said HBP polypeptide.

Another embodiment of the present invention is a method as described above, wherein said agent is present in a sample.

Another embodiment of the present invention is a method of identifying an agent that decreases the signaling activity of FPRL2 polypeptide, said method comprising:
 (a) contacting a FPRL2 polypeptide with HBP polypeptide in the presence or absence of said agent;
 (b) measuring a signaling activity of said FPRL2 polypeptide;
 (c) comparing the amount of said activity measured in a reaction containing FPRL2 polypeptide and said HBP polypeptide without said agent to the amount of said activity measured in a reaction containing said FPRL2 polypeptide, said HBP polypeptide and said agent, wherein a decrease in said activity in the presence of said agent relative to the activity in the absence of said agent identifies said agent as an antagonist or inverse agonist for said FPRL2 polypeptide.

Another embodiment of the present invention is a method as described above, wherein said agent is present in a sample.

Another embodiment of the present invention is a method as described above wherein said FPRL2 polypeptide is expressed by cells on their surface.

Another embodiment of the present invention is a method as described above wherein said FPRL2 polypeptide is present in cell membranes.

Another embodiment of the present invention is a method as described above, wherein said FPRL2 polypeptide is present in or on virus-induced budding membranes.

Another embodiment of the present invention is a method as described above wherein said cells are selected from the group consisting of: COS7-cells, a CHO cell, a LM (TK-) cell, a NIH-3T3 cell, HEK-293 cell, K-562 cell and a 1321N1 astrocytoma cell and other cell lines.

Another embodiment of the present invention is a method as described above, further performed in the presence of Gα16 polypeptide.

Another embodiment of the present invention is a method as described above wherein said measuring or said detecting is performed using a method selected from label displacement, surface plasmon resonance, fluorescence resonance energy transfer, fluorescence quenching, and fluorescence polarization.

Another embodiment of the present invention is a method as described above wherein said agent is selected from the group consisting of a natural or synthetic peptide, a polypeptide, an antibody or antigen-binding fragment thereof, a lipid, a carbohydrate, a nucleic acid, and a small organic molecule.

Another embodiment of the present invention is a method as described above wherein said detecting or measuring a signalling activity or measuring the binding of said FPRL2 polypeptide comprises detecting a change in the level of a second messenger.

Another embodiment of the present invention is a method as described above wherein the step of detecting a signalling activity or said measuring a signalling activity or measuring the binding comprises measurement of guanine nucleotide binding or exchange, adenylate cyclase activity, cAMP, protein kinase C activity, phosphatidylinositol breakdown, diacylglycerol, inositol trisphosphate, intracellular calcium, arachinoid acid concentration, MAP kinase activity, tyrosine kinase activity, reporter gene expression.

Another embodiment of the present invention is a method as described above wherein said measuring a signalling activity comprises using an aequorin-based assay.

Another embodiment of the present invention is an agent obtainable using a screening method disclosed herein.

Another embodiment of the present invention is an antibody which specifically reacts with FPRL2 polypeptide and which increases or decreases:
   (a) the binding of HBP polypeptide to the FPRL2 polypeptide, or
   (b) the signalling activity of HBP polypeptide bound to the FPLRL2 polypeptide Another embodiment of the present invention is a method of in vitro diagnosing a disease or disorder characterized by dysregulation of FPRL2 polypeptide signalling, said method comprising:
   a) contacting a tissue sample comprising a FPRL2 polypeptide with HBP polypeptide;
   b) detecting binding of said HBP polypeptide to said tissue sample; and
   c) comparing the binding detected in step (b) with a standard, wherein a difference in binding relative to said standard is diagnostic of a disease or disorder characterized by dysregulation of FPRL2 polypeptide signalling.

Another embodiment of the present invention is a method of in vitro diagnosing a disease or disorder characterized by dysregulation of FPRL2 polypeptide signalling, said method comprising:
   a) contacting a tissue sample comprising a FPRL2 polypeptide with HBP polypeptide;
   b) detecting a signalling activity of FPRL2 polypeptide in said tissue sample; and
   c) comparing the signalling activity detected in step (b) with a standard, wherein a difference in signalling activity relative to said standard is diagnostic of a disease or disorder characterized by dysregulation of FPRL2 polypeptide signalling.

Another embodiment of the present invention is a method as described above wherein said comparing is performed on a microarray.

Another embodiment of the present invention is a kit for detecting binding to FPRL2 polypeptide, an agent binding to FPRL2 polypeptide or an agent decreasing or increasing the signalling activity of FPRL2 polypeptide, said kit comprising a FPRL2 polypeptide and HBP polypeptide, and packaging materials therefore, wherein said FPRL2 polypeptide and HBP polypeptide are packaged separately.

Another embodiment of the present invention is a kit as described above, wherein said FPRL2 polypeptide is present in a cell expressing FPRL2 polypeptide and wherein said kit further comprises an antibody specific for FPRL2 polypeptide or a FPRL2 polypeptide-specific nucleic probe packaged separately.

Another embodiment of the present invention is a kit as described above, wherein said cell is selected from the group consisting of: COS7-cells, a CHO cell, a LM (TK-) cell, a NIH-3T3 cell, HEK-293 cell, K-562 cell and a 1321N1 astrocytoma cell and other cell lines.

Another embodiment of the present invention is a kit as described above, wherein said FPRL2 polypeptide is present in an isolated cell membrane bearing FPRL2 polypeptide.

Another embodiment of the present invention is a kit as described above, said kit further comprising one or more components of a second messenger assay.

Another embodiment of the present invention is a kit as described above, said kit further comprising G$\alpha$16 polypeptide.

Another embodiment of the present invention is a kit for screening for agents that increase or decrease the signalling activity of FPRL2 polypeptide, said kit comprising
   (a) an isolated polynucleotide encoding a FPRL2 polypeptide, HBP polypeptide and means for detecting FPRL2 polypeptide signalling, and packaging materials therefore, or
   (b) a cell transformed with a polynucleotide encoding a FPRL2 polypeptide, HBP polypeptide and means for detecting FPRL2 polypeptide signalling, and packaging materials therefore.

Another embodiment of the present invention is a kit as described above, wherein the said agents are detected using an antibody specific for FPRL2 polypeptide or a FPRL2 polypeptide-specific nucleic acid probe.

Another embodiment of the present invention is a kit as described above for the diagnosis of a disease or disorder characterized by dysregulation of FPRL2 polypeptide signalling.

Another embodiment of the present invention is a kit as described above, wherein the said disease or disorder is detected using an antibody specific for FPRL2 polypeptide or a FPRL2 polypeptide-specific nucleic acid probe.

Another embodiment of the present invention is a kit as described above further comprising a standard of FPRL2 polypeptide activity as measured in a cell line expressing FPRL2 polypeptide in the presence of HBP polypeptide.

Another embodiment of the present invention is a use of HBP polypeptide, or an antibody as described above for the manufacture of a pharmaceutical composition for preventing, treating and/or alleviating diseases or disorders characterized by dysregulation of FPRL2 polypeptide signalling.

Another embodiment of the present invention is a use as described above, wherein said diseases or disorders characterized by dysregulation of FPRL2 polypeptide signalling are selected from the group consisting of cell migration, cancer, development of tumours and tumour metastasis, inflammatory and neoplastic processes, wound and bone healing and dysfunction of regulatory growth functions, obesity, anorexia, bulimia, acute heart failure, hypotension, hypertension, urinary retention, osteoporosis, angina pectoris, restenosis, atherosclerosis, thrombosis and other cardiovascular diseases, autoimmune and, diseases characterized by excessive smooth muscle cell proliferation, aneurysms, diseases characterized by loss of smooth muscle cells or reduced smooth muscle cell proliferation, stroke, ischemia, ulcers, allergies, prostatic hypertrophy, migraine, vomiting, psychotic and neurological disorders, including anxiety, schizophrenia, manic depression, depression, delirium, dementia and severe mental retardation, degenerative diseases, neurodegenerative diseases such as Alzheimer's disease or Parkinson's disease, and dyskinasias, such as Huntington's disease or Gilles de la Tourett's syndrome and other related diseases including thrombosis and other cardiovascular diseases, autoimmune and inflammatory diseases such as psoriasis, Eczeme, inflammatory and trophic diseases of skin, rheumatoid arthritis, scleroderma, lupus, polymyositis, dermatomysitis, Crohn's disease, inflammatory bowel disease (IBD), Irritable Bowel Syndrome, Ulcerative Colitis, Asthma, Chronic Obstructive Pulmonary Disease, Allergic Rhinitis, Fibromyalgia, Organ Transplant Rejection, Graft versus host disease, Multiple Sclerosis, Acute, Ischemic Stroke, Infectious diseases, Hepatitis A, Hepatitis B, Hepatitis C, Sepsis, Septic shock, Chronic bronchitis, infections such as bacterial, fungal, protozoan and viral infections, such as infections caused by HIV1 and HIV2, and pain, cancer, anorexia, bulimia, asthma, acute heart failure, hypertension, urinary retention, osteoporosis, angina pectoris, myocardial infarction, ulcers, allergies, benign prostatic hypertrophy, and Type 1 Diabetes, Type 2 Diabetes, Osteoarthritis, Diabetic Retinopathy, Diabetic Nephropathy and fertility dysfunctions, foetal developmental disorders Another embodiment of the present invention is a method for the production of a pharmaceutical composition comprising the steps of admixing an antibody as described above, with a pharmaceutical carrier.

Another embodiment of the present invention is a pharmaceutical composition comprising an antibody as described above.

Another embodiment of the present invention is a method, kit, use or antibody as described above wherein an HBP polypeptide corresponds to a sequence represented by SEQ ID NO: 18.

Another embodiment of the present invention is a method, kit, use or antibody as described above wherein an FPRL2 polypeptide corresponds to a sequence represented by SEQ ID NO: 2.

Another embodiment of the present invention is a HBP polypeptide corresponding to the sequence represented by SEQ ID NO: 18.

Another embodiment of the present invention is a polypeptide which has least 50% identity to the sequence represented by SEQ ID NO: 18.

Another embodiment of the present invention is a polypeptide which is a functional fragment of a HBP polypeptide corresponding to the sequence represented by SEQ ID NO: 18.

The present invention also relates to nucleic acids encoding said HBP polypeptides as listed above.

Another embodiment of the present invention is a functional antibody or antigen-binding fragment thereof which specifically reacts with formyl peptide receptor like-2 (FPRL2) polypeptide and which increases or decreases the signalling activity of the formyl peptide receptor like-2 (FPRL2) polypeptide.

Another embodiment of the present invention is an antibody which specifically reacts with formyl peptide receptor like-2 (FPRL2) polypeptide, and which increases or decreases the signalling activity of the formyl peptide receptor like-2 (FPRL2) polypeptide.

Another embodiment of the present invention is an antibody which specifically reacts with formyl peptide receptor like-2 (FPRL2) polypeptide, and which increases or decreases the signalling activity of the formyl peptide receptor like-2 (FPRL2) polypeptide, when the amount of said activity measured in the presence of the antibody is at least 10% of the amount induced by said HBP.

Another embodiment of the present invention is an antibody which specifically reacts with formyl peptide receptor like-2 (FPRL2) polypeptide, and is obtainable using a screening method as described herein.

Another embodiment of the present invention is an antibody as described herein wherein said antibody is an agonist of the formyl peptide receptor like-2 (FPRL2) polypeptide.

Another embodiment of the present invention is an antibody as described herein wherein said antibody is monoclonal.

Another embodiment of the present invention is an antibody as described herein which corresponds to Mab FPRL2 422F 2B9 1C11 produced by the hybridoma cell line named FPRL2 422F 2B9 deposited under BCCM Accession number: LMBP 6405CB, at BCCM/LMBP Plasmid collection, Department of Molecular Biology, Gent University, Technologiepark 927, B-9052, Gent-Zwijnaarde, Belgium, on Apr. 28, 2005.

Another embodiment of the present invention is an antibody as described herein which corresponds to Mab FPRL2 422F 2G3 1A10 produced by the hybridoma cell line named FPRL2 422F 2G3 deposited under BCCM Accession number: LMBP 6406CB, at BCCM/LMBP Plasmid collection, Department of Molecular Biology, Gent University, Technologiepark 927, B-9052, Gent-Zwijnaarde, Belgium, on Apr. 28, 2005.

Another embodiment of the present invention is an antibody as described herein wherein said antibody is polyclonal.

Another embodiment of the present invention is an antibody as described herein wherein said antibody is an antagonist of the formyl peptide receptor like-2 (FPRL2) polypeptide.

Another embodiment of the present invention is an antibody as described herein wherein said antibody is humanized.

Another embodiment of the present invention is a functional fragment of an antibody as described herein.

Another embodiment of the present invention is a functional fragment as described herein, which comprises the antigen binding fragment.

Another embodiment of the present invention is an homologous sequence of the amino acid sequence of an antibody or finctional fragment as described above, or of a nucleotide sequence encoding said antibody or functional fragment.

Another embodiment of the present invention is an antibody, functional fragment or homologous sequence as described herein for preventing, treating and/or alleviating diseases or disorders characterized by dysregulation of formyl peptide receptor like-2 (FPRL2) polypeptide signalling.

In another aspect of the invention, the invention provides method of treating an individual with a diseases or disorders characterized by dysregulation of FPRL2 polypeptide signaling comprising administering a therapeutically effective dose of a modulator of a FPRL2 polypeptide.

In one embodiment, the modulator of a FPRL2 polypeptide is an antibody, functional fragment or homologous sequence as described herein.

Another embodiment of the present invention is an antibody, functional fragment or homologous sequence as described herein, wherein said diseases or disorders characterized by dysregulation of formyl peptide receptor like-2 (FPRL2) polypeptide signalling are selected from the group consisting of cell migration, cancer, development of tumours and tumour metastasis, inflammatory and neoplastic processes, wound and bone healing and dysfunction of regulatory growth functions, obesity, anorexia, bulimia, acute heart failure, hypotension, hypertension, urinary retention, osteoporosis, angina pectoris, restenosis, atherosclerosis, thrombosis and other cardiovascular diseases, autoimmune and, diseases characterized by excessive smooth muscle cell proliferation, aneurysms, diseases characterized by loss of smooth muscle cells or reduced smooth muscle cell proliferation, stroke, ischemia, ulcers, allergies, prostatic hypertrophy, migraine, vomiting, psychotic and neurological disorders, including anxiety, schizophrenia, manic depression, depression, delirium, dementia and severe mental retardation, degenerative diseases, neurodegenerative diseases such as Alzheimer's disease or Parkinson's disease, and dyskinasias, such as Huntington's disease or Gilles de la Tourett's syndrome and other related diseases including thrombosis and other cardiovascular diseases, autoimmune and inflammatory diseases such as psoriasis, Eczeme, inflammatory and trophic diseases of skin, rheumatoid arthritis, scleroderma, lupus, polymyositis, dermatomysitis, Crohn's disease, inflammatory bowel disease (IBD), Irritable Bowel Syndrome, Ulcerative Colitis, Asthma, Chronic Obstructive Pulmonary Disease, Allergic Rhinitis, Fibromyalgia, Organ Transplant Rejection, Graft versus host disease, Multiple Sclerosis, Acute, Ischemic Stroke, Infectious diseases, Hepatitis A, Hepatitis B, Hepatitis C, Sepsis, Septic shock, Chronic bronchitis, infections such as bacterial, fungal, protozoan and viral infections, such as infections caused by HIV1 and HIV2, and pain, cancer, anorexia, bulimia, asthma, acute heart failure, hypertension, urinary retention, osteoporosis, angina pectoris, myocardial infarction, ulcers, allergies, benign prostatic hypertrophy, and Type 1 Diabetes, Type 2 Diabetes, Osteoarthritis, Diabetic Retinopathy, Diabetic Nephropathy and fertility dysfunctions, foetal developmental disorders.

BRIEF DESCRIPTION OF THE DRAWINGS

FIG. 1 represents nucleotide sequence (SEQ ID NO: 32) as cloned in pCDNA3 and deduced amino acid sequence (SEQ ID NO: 2) of the human FPRL2 receptor. The start and stop codons are indicated in bold and restriction sites for cloning (Eco RI and XbaI) are underlined.

FIG. 8 lists amino acid and nucleic acid sequences according to the invention (sequence listing).

Immunodetection of phosphorylated ERK1/2 in FPRL2-expressing CHO-K1 cells following stimulation by F2L for 10 min. J. Kinetics of ERK1/2 activation following stimulation by 100 nM F2L. Each experiment displayed in A to I was repeated at least three times.

FIG. 12. Expression profile of human FPRL2. A. Transcripts encoding human FPRL2 were amplified by RT-PCR in a set of human leukocyte populations. act.: activated. Mononucl.: mononuclear cells. iDC: immature dendritic cells. mDC: mature dendritic cells. B. Distribution of FPRL2 in a set of human tissues, by using quantitative RT-PCR (Taqman). The data were normalized for the expression of GAPDH used as control. C. Anti-FPRL2 monoclonal antibodies were characterized by FACS on CHO-K1 cells expressing FPR, FPRL1 and FPRL2. 1C4: bold solid line. 1D2: dotted line. 1E1: dashed line. Control labeling (IgG2a): thin solid line. The profiles of 1D2 and 1E1 are superimposed and cannot therefore be distinguished. D. The expression of FPRL2 was analyzed by FACS on immature DCs using the three monoclonal antibodies. Anti-FPRL2 Abs: bold solid line. Control labeling (IgG2a): thin solid line. E. Expression of FPRL2 on intact and permeabilized DCs using 1D2. 1D2: bold solid line. Control labeling (IgG2a): thin solid line. F. Expression of FPRL2 on immature (bold solid line) and mature (thin solid line) DCs using 1D2. Control labeling (IgG2a): dotted lines.

Figure 13:
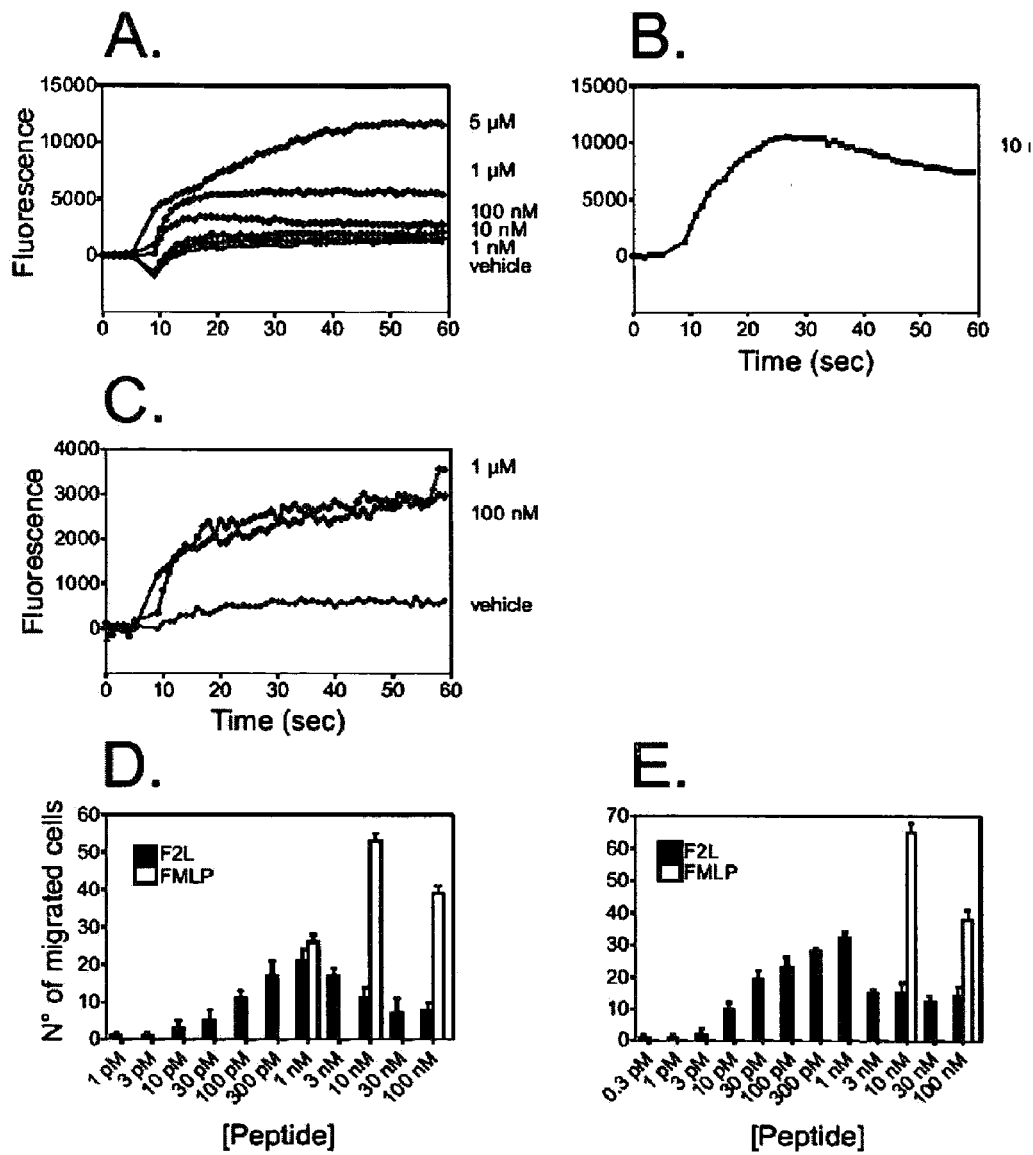

FIG. 13. Biological activity of F2L on primary immune cells. A. and B. Recording of $Ca^{2+}$ flux in monocyte-derived DCs, in response to various concentrations of F2L (A) and to 10 nM of FMLP (B). C. Recording of $Ca_{2+}$ flux in monocytes, in response to 100 nM and 1 µM of F2L. D. and E. Chemotaxis of monocyte-derived human immature DCs (D) and peripheral blood mononuclear cells (E) in response to F2L. The displayed responses are representative of four donors, out of five tested.

Figure 14:
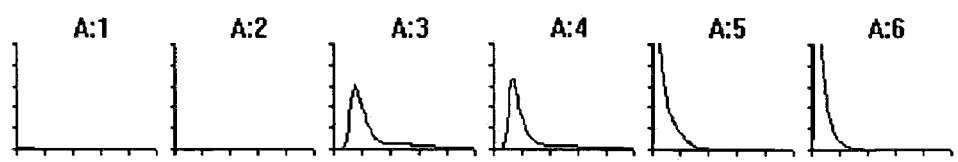

FIG. 14. Controls of aequorine assays on human FPRL2 expressing cells. (A1-A2: Aequorin medium, A3-A4: ATP 20 µM, A5-A6: Triton 0.1%) (scale: 150 000 Relative Light Units (RLU)). Each response graph corresponds to the indicated position on the FPRL2 96-well plate in Table 2.

Figure 15:
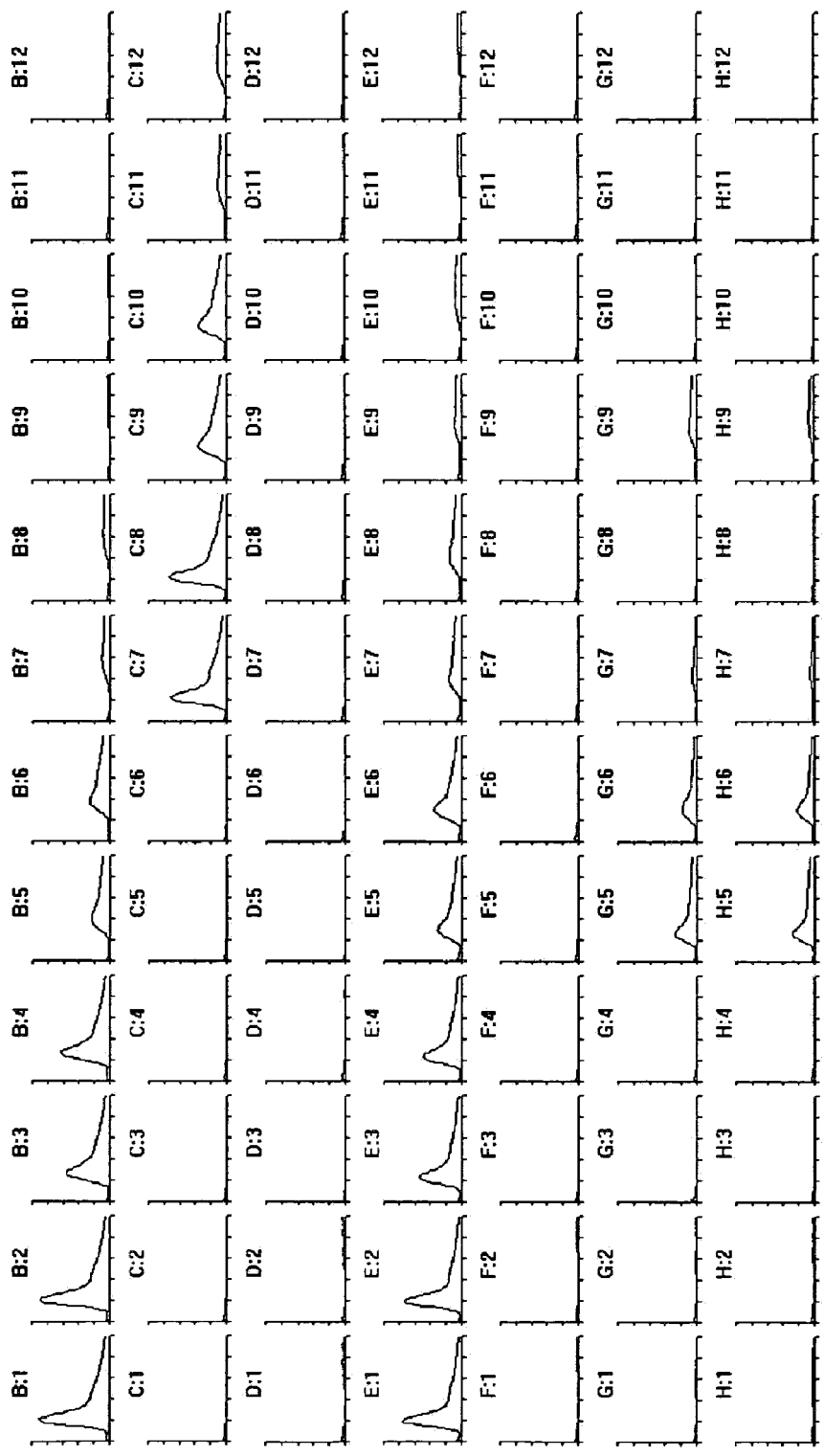

FIG. 15. Functional monoclonal antibodies and ligands in aequorin assays on human FPRL2 expressing cells. Scale: 50 000 RLU. Each response graph corresponds to the indicated position on the FPRL2 96-well plate in Table 2.

DETAILED DESCRIPTION

The invention is based on the discovery that HBP polypeptide is a natural ligand for the orphan G protein coupled receptor FPRL2 polypeptide and on methods of using the binding of this ligand to the receptor in drug screening methods. The known ligand and its interaction with the receptor FPRL2 polypeptide also provides for the diagnosis of conditions involving dysregulated receptor activity. The invention also relates to a kit comprising FPRL2 polypeptide and homologous sequences, its corresponding polynucleotide and/or recombinant cells expressing the polynucleotide, to identify agonist, antagonist, inverse agonist and modulator compounds of the receptor polypeptide and/or its corresponding polynucleotide. Such kits are useful for the diagnosis, prevention and/or a treatment of diseases and disorders related to FPRL2 polypeptide activity.

The invention also relates to novel agonist, antagonist, inverse agonist and modulator compounds of the receptor polypeptide and its corresponding polynucleotide, identified according to the method of the invention.

All references referred to below and above are incorporated herein by reference in their entirety.

The invention is based on the finding that a fragment of HBP (HBP polypeptide) is a natural ligand of the orphan receptor FPRL2 (SEQ ID NO: 2). This invention thus relates to the HBP polypeptide ligand/receptor pair, and to functional homologs of the receptor which also bind HBP polypeptide and cells transformed by a vector comprising the nucleotide sequence encoding the receptor (SEQ ID NO: 1) in combination with the HBP polypeptide ligand. The invention also relates to a composition consisting essentially of an isolated FPLR2 polypeptide and an isolated BP polypeptide, as well as to methods of identifying agents that modulate the activities of FPRL2 polypeptides. The methods are useful for the identification of agonist, inverse agonist or antagonist compounds useful for the development of new drugs. The interaction of FPRL2 with HBP polypeptide is also useful for the development of diagnostics for diseases related to FPRL2 activity.

The invention encompasses a method of identifying an agent that modulates the function of FPLR2, the method comprising : a) contacting a FPLR2 polypeptide with a HBP polypeptide in the presence and absence of a candidate modulator under conditions permitting the binding of the HBP polypeptide to the FPLR2 polypeptide; and b) measuring binding of the FPLR2 polypeptide to the HBP polypeptide wherein a decrease in binding in the presence of the candidate modulator, relative to binding in the absence of the candidate modulator, identifies the candidate modulator as an agent that modulates the function of FPLR2 polypeptide.

The invention further encompasses a method of detecting, in a sample, the presence of an agent that modulates the function of FPLR2, the method comprising: a) contacting a FPLR2 polypeptide with a HBP polypeptide in the presence and absence of the sample under conditions permitting the binding of the HBP polypeptide to the FPLR2 polypeptide; and b) measuring binding of the FPLR2 polypeptide to the HBP polypeptide wherein a decrease in binding in the presence of the sample, relative to binding in the absence of the sample, indicates the presence, in the sample of an agent that modulates the function of FPLR2.

In one embodiment of either of the preceding methods, the measuring is performed using a method selected from label displacement, surface plasmon resonance, fluorescence resonance energy transfer, fluorescence quenching, and fluorescence polarization.

The invention further encompasses a method of identifying an agent that modulates the function of FPLR2, the method comprising: a) contacting a FPLR2 polypeptide with a HBP polypeptide in the presence and absence of a candidate modulator; and b) measuring a signalling activity of the FPLR2 polypeptide, wherein a change in the activity in the presence of the candidate modulator relative to the activity in the absence of the candidate modulator identifies the candidate modulator as an agent that modulates the function of FPLR2 polypeptide.

The invention further encompasses a method of identifying an agent that modulates the function of FPLR2 polypeptide, the method comprising: a) contacting a FPLR2 polypeptide with a candidate modulator; b) measuring a signalling activity of the FPLR2 polypeptide in the presence of the candidate modulator; and c) comparing the activity measured in the presence of the candidate modulator to the activity measured in a sample in which the FPLR2 polypeptide is contacted with a HBP polypeptide at its $EC_{50}$, wherein the candidate modulator is identified as an agent that modulates the function of FPLR2 polypeptide when the amount of the activity measured in the presence of the candidate modulator is at least 20% of the amount induced by the HBP polypeptide present at its $EC_{50}$.

The invention further encompasses a method of detecting the presence, in a sample, of an agent that modulates the function of FPLR2 polypeptide, the method comprising: a) contacting a FPLR2 polypeptide with HBP polypeptide in the presence and absence of the sample; b) measuring a signalling activity of the FPLR2 polypeptide; and c) comparing the amount of the activity measured in a reaction containing FPLR2 polypeptide and HBP polypeptide without the sample to the amount of the activity measured in a reaction containing FPLR2 polypeptide, HBP polypeptide and the sample, wherein a change in the activity in the presence of the sample relative to the activity in the absence of the sample indicates the presence, in the sample, of an agent that modulates the function of FPLR2 polypeptide.

The invention further encompasses a method of detecting the presence, in a sample, of an agent that modulates the function of FPLR2 polypeptide, the method comprising: a) contacting a FPLR2 polypeptide with the sample; b) measuring a signalling activity of the FPLR2 polypeptide in the presence of the sample; and c) comparing the activity measured in the presence of the sample to the activity measured in a reaction in which the FPLR2 polypeptide is contacted with a HBP polypeptide present at its $EC_{50}$, wherein an agent that modulates the function of FPLR2 polypeptide is detected if the amount of the activity measured in the presence of the sample is at least 20% of the amount induced by the HBP polypeptide present at its $EC_{50}$.

In one embodiment of each of the preceding methods, the HBP polypeptide is detectably labeled. In a preferred embodiment, the HBP polypeptide is detectably labeled with a moiety selected from the group consisting of a radioisotope, a fluorophore, a quencher of fluorescence, an enzyme, and an affinity tag.

In an embodiment of each of the preceding methods, the contacting is performed in or on a cell expressing the FPLR2 polypeptide.

In an embodiment of each of the preceding methods the contacting is performed in or on synthetic liposomes.

In an embodiment of each of the preceding methods the contacting is performed in or on virus-induced budding membranes containing a FPLR2 polypeptide.

In an embodiment of each of the preceding methods the contacting is performed using a membrane fraction from cells expressing the FPLR2 polypeptide.

In an embodiment of each of the preceding methods the measuring is performed using a method selected from the group consisting of label displacement, surface plasmon resonance, fluorescence resonance energy transfer, fluorescence quenching, and fluorescence polarization.

In an embodiment of each of the preceding methods the agent is selected from the group consisting of a natural or synthetic peptide or polypeptide, an antibody or antigen-binding fragment thereof, a lipid, a carbohydrate, a nucleic acid, an antisense nucleotide, and a small organic molecule.

In one embodiment of the methods wherein a signalling activity is measured, the step of measuring a signalling activity of the FPLR2 polypeptide comprises detecting a change in the level of a second messenger.

In another embodiment of the methods wherein a signalling activity is measured, the step of measuring a signalling activity comprises measurement of guanine nucleotide binding or exchange, adenylate cyclase activity, cAMP, Protein Kinase C activity, phosphatidylinositol breakdown, diacylglycerol, inositol trisphosphate, intracellular calcium, arachinoid acid, MAP kinase activity, tyrosine kinase activity, or reporter gene expression.

In one embodiment, the step of measuring a signalling activity comprises using an aequorin-based assay.

The invention further comprises a method of modulating the activity of a FPLR2 polypeptide in a cell, the method comprising the step of delivering to the cell an agent that modulates the activity of a FPLR2 polypeptide, such that the activity of FPLR2 polypeptide is modulated.

The invention further encompasses a method of diagnosing a disease or disorder characterized by dysregulation of FPLR2 polypeptide signalling, the method comprising: a) contacting a tissue sample with an antibody specific for a FPLR2 polypeptide; b) detecting binding of the antibody to the tissue sample; and c) comparing the binding detected in step (b) with a standard, wherein a difference in binding relative to the standard is diagnostic of a disease or disorder characterized by dysregulation of FPLR2 polypeptide.

The invention further encompasses a method of diagnosing a disease or disorder characterized by dysregulation of FPLR2 polypeptide signalling, the method comprising: a) isolating nucleic acid from a tissue sample; b) amplifying a FPLR2 polynucleotide, using the nucleic acid as a template; and c) comparing the amount of amplified FPLR2 polynucleotide produced in step (b) with a standard, wherein a difference in the amount of amplified FPLR2 polynucleotide relative to the standard is diagnostic of a disease or disorder characterized by dysregulation of FPLR2 polypeptide.

The invention further encompasses a method of diagnosing a disease or disorder characterized by dysregulation of FPLR2 polypeptide signalling, the method comprising: a) isolating nucleic acid from a tissue sample; b) amplifying a FPLR2 polynucleotide, using the nucleic acid as a template; and c) comparing the sequence of the amplified FPLR2 polynucleotide produced in step (b) with a standard, wherein a difference in the sequence, relative to the standard is diagnostic of a disease or disorder characterized by dysregulation of FPLR2 polypeptide. In one embodiment, the step of amplifying comprises RT/PCR. In another embodiment, the standard is SEQ ID NO: 1. In another embodiment, the step of comparing the sequence comprises minisequencing. In another embodiment, the step of comparing the amount is performed using a microarray.

The invention further encompasses a composition comprising or consisting essentially of an isolated FPLR2 polypeptide and an isolated HBP polypeptide. An isolated FPLR2 polypeptide and an isolated HBP polypeptide together can form a complex that is useful for the identification of agents that modulate their interaction, the identification of agents that modulate the activity of FPLR2 polypeptides, and the identification of individuals suffering from a disease or disorder mediated by or involving FPLR2 polypeptide. Complexed or uncomplexed (i.e., bound or unbound) isolated FPLR2 polypeptide and isolated HBP polypeptide is thus the essential element or basis of the assays and methods of the invention. The composition "consisting essentially of" an isolated FPLR2 polypeptide and an isolated HBP polypeptide can comprise additional components, however, such additional components are not essential to the novel interaction upon which the invention is based. The composition "consisting essentially of" an isolated FPLR2 polypeptide and an isolated HBP polypeptide is distinct from and excludes naturally occurring complexes between FPLR2 polypeptides and HBP polypeptide, present e.g., in cells, tissues or in cell or tissue extracts. The composition of the invention is also distinct from and excludes complexes between FPLR2 polypeptides expressed from recombinant constructs and naturally-occurring HBP polypeptide.

Kits according to the invention are useful, for example, for screening for agents that modulate the activity of FPLR2 polypeptide, identifying the presence of an agent that modulates FPLR2 polypeptide in a sample, or for diagnosis of a disease or disorder characterized by dysregulation of FPLR2 polypeptide. Kits according to the invention will additionally comprise packaging materials necessary for such kits. Kits according to the invention can additionally comprise a standard. In one embodiment, the standard is a sample from an individual not affected by a disease or disorder characterized by dysregulation of FPLR2 polypeptide.

As used herein, the term "formyl peptide receptor-like 2 (FPRL2) polypeptide" refers to a polypeptide having at least 80% amino acid identity, preferably 85%, 90%, 95%, or higher, up to and including 100% identity, with SEQ ID NO: 2, and which has FPRL2 activity i.e., the FPRL2 polypeptide binds a HBP polypeptide or a functional fragment thereof. An FPRL2 polypeptide may also be a functional fragment of SEQ ID NO: 2 i.e. a portion of SEQ ID NO:2 which is still capable of binding to a HBP polypeptide or a functional fragment thereof. A functional fragment of SEQ ID NO: 2 may comprise at least 10, 20, 30, 40, 50, 60, 70, 80, 90, or 95% of the amino acids of the sequence represented by SEQ ID NO:2.

Optimally, a FPRL2 polypeptide also has FPRL2 signalling activity as defined herein.

As used herein, "FPRL2 polypeptide activity" refers to specific binding to or signalling by a HBP polypeptide as defined herein.

A homologous sequence (which may exist in other mammal species or specific groups of human populations), where homology indicates sequence identity, means a sequence which presents a high sequence identity (more than 80%, 85%, 90%, 95% or 98% sequence identity) with the complete human nucleotide of SEQ ID NO: 1 or the complete human amino acid sequence of SEQ ID NO: 2. A functional homolog is characterized by the ability to bind a HBP polypeptide as defined herein or by the ability to initiate or propagate a signal in response to ligand binding, or both.

Homologous sequences of a sequence according to the invention may include an amino acid or nucleotide sequence encoding a similar receptor which exists in other animal species (rat, mouse, cat, dog, etc.) or in specific human population groups, but which are involved in the same biochemical pathway.

Such homologous sequences may comprise additions, deletions or substitutions of one or more amino acids or nucleotides, which do not substantially alter the functional characteristics of the receptor according to the invention. That is, homologs will have at least 90% of the activity of wt full length human FPRL2 polypeptide and will bind HPB polypeptide specifically.

Such homologous sequences can also be nucleotide sequences of more than 50, 100, 200, 300, 400, 600, 800 or 1000 nucleotides which are able to hybridize to the complete human FPRL2 sequence under stringent hybridisation conditions (such as the ones described by SAMBROOK et al., Molecular Cloning, Laboratory Manuel, Cold Spring, Harbor Laboratory press, New York). An example of "stringent hybridization conditions" is as follows: hybridize in 50% formamide, 5×SSC, 50 mM sodium phosphate (pH 6.8), 0.1% sodium pyrophosphate, 5× Denhardt's solution, 50 µg/ml sonicated salmon sperm DNA, 0.1% SDS and 10% dextran sulfate at 42° C.; and wash at 42° C. (or higher, e.g., up to two degrees C. below the $T_m$ of the perfect complement of the probe sequence) in 0.2×SSC and 0.1% SDS.

As used herein, the term "formyl peptide receptor-like 2 (FPRL2) signalling activity" refers to the initiation or propagation of signalling by a FPRL2 polypeptide. FPRL2 signalling activity is monitored by measuring a detectable step in a signalling cascade by assaying one or more of the following: stimulation of GDP for GTP exchange on a G protein; alteration of adenylate cyclase activity; protein kinase C modulation; phosphatidylinositol breakdown (generating second messengers diacylglycerol, and inositol trisphosphate); intracellular calcium flux; activation of MAP kinases; modulation of tyrosine kinases; or modulation of gene or reporter gene activity. A detectable step in a signalling cascade is considered initiated or mediated if the measurable activity is altered by 10% or more above or below a baseline established in the substantial absence of a HBP polypeptide relative to any of the FPRL2 polypeptide activity assays described herein below. The measurable activity can be measured directly, as in, for example, measurement of cAMP or diacylglycerol levels. Alternatively, the measurable activity can be measured indirectly, as in, for example, a reporter gene assay.

The term "a heme binding protein (HBP) polypeptide" refers to a polypeptide having at least 50% or higher identity to SEQ ID NO: 18, and the defined polypeptide specifically binds to and activates a signaling activity of a FPRL2 polypeptide. Preferably, the polypeptide is at least 55%, or higher identity to SEQ ID NO: 18. Preferably, the polypeptide is at least 60%, or 70%, or 80%, 85%, 90%, 95%, or 98%or higher identity to SEQ ID NO: 18.

A HBP polypeptide may also be a functional fragment of SEQ ID NO:18 i.e. a portion of SEQ ID NO:18 which is still capable of binding to a FPRL2 polypeptide or a functional fragment thereof. A functional fragment of SEQ ID NO: 18 comprise at least 5, 6, 7, 8, 9, 10, 11, 12, 13, 14, 15, 16, 17, 18, 19, 20, or 21, or a number in the range between any two of the aforementioned numbers of amino acids of the sequence represented by SEQ ID NO:18.

The term "specifically binds" means that the HBP polypeptide has an $EC_{50}$, $IC_{50}$ or a $K_d$ of 100 nM or less. "HBP polypeptide" also refers to a fragment of a polypeptide meeting the preceding definition, wherein the fragment retains at least 50% of the binding activity and level of signaling activation of the full length polypeptide of SEQ ID NO: 18. A HBP polypeptide also includes a analog, variant or some short polypeptide from COOH-terminal end and/or NH2-terminal end of SEQ ID NO 18. A HBP polypeptide can also comprise chemical and/or amino acid additions, insertions, deletions or substitutions relative to SEQ ID NO: 18, as long as the resulting polypeptide retains at least 50% of the binding activity and level of signaling activation of the full length polypeptide represented by SEQ ID NO: 18. A HBP polypeptide, can comprise additional sequences, as in for example, a HBP fusion protein. Non-limiting examples of fusion partners include glutathione-S-transferase (GST), maltose binding protein, alkaline phosphatase, thioredoxin, green fluorescent protein (GFP), histidine tags (e.g., 6× or greater His (SEQ ID NO: 36)), or epitope tags (e.g., Myc tag, FLAG tag). An HBP polypeptide can be a polypeptide sequence represented by SEQ ID NO: 18, with or without an acetyl group at the N-terminus. An HBP polypeptide can be a polypeptide sequence represented by SEQ ID NO: 18, with or without a label such as biotin or any other dye (fluorescent dye) or with a radioisotope. Where a label is present, it may attach, for example, through an acetyl group at the N-terminus of the HBP polypeptide. One or more combinations of the above features are within the scope of the invention.

Homologous sequences of SEQ ID NO: 18 according to the invention may include an amino acid or nucleotide sequence encoding a similar sequence which exists in other animal species (rat, mouse, human, cat, dog, etc.) or in specific human population groups, but which are involved in the same biochemical pathway.

Such homologous sequences may comprise additions, deletions or substitutions of one or more amino acids or nucleotides, which do not substantially alter the functional characteristics of the peptide according to the invention. That is, homologs will have at least 90% of the activity of an amino acid sequence represented by SEQ ID NO:18 and will bind or activate FPRL2 specifically.

As used herein, the term "detectable step" refers to a step that can be measured, either directly, e.g., by measurement of a second messenger or detection of a modified (e.g., phosphorylated) protein, or indirectly, e.g., by monitoring a downstream effect of that step. For example, adenylate cyclase activation results in the generation of cAMP. The activity of adenylate cyclase can be measured directly, e.g., by an assay that monitors the production of cAMP in the assay, or indirectly, by measurement of actual levels of cAMP.

Preferably, a recombinant cell according to the invention is a recombinant cell transformed by a plasmid, cosmid or viral vector, preferably a baculovirus, an adenovirus, or a semliki forest virus, and the cell is preferably selected from the group consisting of bacterial cells, yeast cells, insect cells or mammal cells.

According to a preferred embodiment of the present invention, the cell is selected from the group consisting of COS-7 cells, a CHO cell, a LM (TK-) cell, a NIH-3T3 cell, HEK-293 cell, K-562 cell or a 1321N1 astrocytoma cell. Other transfectable cell lines are also useful, however. Preferably, the vector comprises regulatory elements operatively linked to the polynucleotide sequence encoding the receptor according to the invention, so as to permit expression thereof.

Another aspect of the present invention is related to the use of a specific active portion of the sequences. As used herein, an "active portion" refers to a portion of a sequence that is of sufficient size to exhibit normal or near normal pharmacology (e.g., receptor activity (as defined herein), the response to an activator or inhibitor, or ligand binding are at least 90% of the level of activity, response, or binding exhibited by a wild type receptor). "A portion" as it refers to a sequence encoding a receptor, refers to less than 100% of the sequence (i.e., 99, 90, 80, 70, 60, 50% etc ... ). The active portion could be a receptor which comprises a partial deletion of the complete nucleotide or amino acid sequence and which still maintains the active site(s) and protein domain(s) necessary for the binding of and interaction with a specific ligand, preferably HBP polypeptide.

In another embodiment of any of the preceding methods, the contacting is performed in or on synthetic liposomes (Mirzabekov et al., 2000) or virus-induced budding membranes containing a FPRL2 polypeptide. (see Patent application WO0102551, Virus-like particles, their Preparation and their Use preferably in Pharmaceutical Screening and Functional Genomics (2001) incorporated herein by reference).

As used herein, "ligand" refers to a moiety that is capable of associating or binding to a receptor. According to the method of the invention, a ligand and a receptor have a binding constant that is sufficiently strong to allow detection of binding by an assay method that is appropriate for detection of a ligand binding to a receptor (e.g. a second messenger assay to detect an increase or decrease in the production of a second messenger in response to ligand binding to the receptor, a binding assay to measure protein-ligand binding or an immunoassay to measure antibody-antigen interactions). A ligand according to the invention includes the actual molecule that binds a receptor or a ligand may be any nucleotide, antibody, antigen, enzyme, small organic molecule, peptide, polypeptide or nucleic acid capable of binding to the receptor. A ligand is preferably a HBP polypeptide, a peptide or a nucleic acid sequence. According to the method of the invention, a ligand and receptor specifically bind to each other (e.g. via covalent or hydrogen bonding or via an interaction between, for example, a protein and a ligand, an antibody and an antigen or protein subunits).

Another aspect of the present invention is related to a method for the screening, detection and recovery of candidate modulators of a receptor of the invention comprising the steps of: contacting a cell expressing FPRL2 polypeptide with HBP polypeptide under conditions which permit binding of HBP polypeptide to FPRL2 polypeptide, in the presence of the candidate modulator, performing a second messenger assay, and comparing the results of the second messenger assay obtained in the presence or absence of the candidate modulator.

Another aspect of the present invention is related to a method for the screening, detection and possible recovery of candidate modulators of a receptor of the invention comprising the steps of: contacting a cell membrane expressing FPRL2 polypeptide with HBP polypeptide under conditions which permit binding of HBP polypeptide to FPRL2 polypeptide, performing a second messenger assay, and comparing the results of the second messenger assay obtained in the presence or absence of the candidate modulator.

In another embodiment, the step of measuring a signalling activity of the FPRL2 polypeptide comprises detecting a change in the level of a second messenger.

A further aspect of the present invention is related to the unknown agonist and/or antagonist compounds identified and/or recovered by the method of the invention, as well as to a diagnostic kit comprising the (unknown) compounds or a pharmaceutical composition (including a vaccine) comprising an adequate pharmaceutical carrier and a sufficient amount of the (unknown) compound.

An antagonist compound according to the invention means a molecule or a group of molecules able to bind to the receptor according to the invention and block the binding of natural compounds (HBP polypeptide).

The invention further encompasses a method of diagnosing a disease or disorder characterized by dysregulation of FPRL2 polypeptide signalling, the method comprising: a) contacting a tissue sample with an antibody specific for a FPRL2 polypeptide and an antibody specific for a FPRL2 ligand; b) detecting binding of the antibodies to the tissue sample; and c) comparing the binding detected in step (b) with a standard, wherein a difference in binding of either antibody or both, relative to the standard, is diagnostic of a disease or disorder characterized by dysregulation of FPRL2 polypeptide.

The invention further encompasses a method of diagnosing a disease or disorder characterized by dysregulation of FPRL2 polypeptide signalling, the method comprising: a) isolating a tissue sample; b) measuring the concentration of HBP polypeptide; and c) comparing the amount of LIGAND measured in step (b) with a standard, wherein a difference in the amount of HBP polypeptide relative to the standard is diagnostic of a disease or disorder characterized by dysregulation of FPRL2 polypeptide.

A further aspect of the present invention is related to a non-human mammal comprising a homozygous null mutation (homozygous "knock-out") of the polynucleotide sequence encoding the FPRL2 polypeptide receptor according to the invention, or a transgenic non-human mammal that over expresses a FPRL2 polypeptide above the natural level of expression.

As used herein. "above the natural level of expression" refers to a level that is at least 2-fold, preferably 5-fold, more preferably 10-fold and most preferably 100-fold or more (i.e., 150-fold, 200-fold, 250-fold, 500-fold, 1000-fold, 10,000-fold etc.) as compared to the level of expression of the endogenous receptor in its normal native context. A transgenic non-human mammal according to the invention will express the transgene in at least one tissue or cell type but can express the FPRL2 polypeptide transgene in all tissues and cells. A transgenic non-human mammal can be obtained by a method well known by a person skilled in the art, for instance, as described in document WO 98/20112 using the classical technique based upon the transfection of embryonic stem cells, preferably according to the method described by Carmeliet et al. (Nature, Vol. 380, p. 435-439, 1996).

"Gene targeting" is a type of homologous recombination that occurs when a fragment of genomic DNA is introduced into a mammalian cell and that fragment locates and recombines with endogenous homologous sequences as exemplified in U.S. Pat. No. 5,464,764, and U.S. Pat. No. 5,777,195, the contents of which are hereby incorporated by reference herein in their entireties. As used herein the term "transgenic animal" refers to a non-human animal in which one or more, and preferably essentially all, of the cells of the animal contain a transgene introduced by way of human intervention, such as by transgenic techniques known in the art. The transgene can be introduced into the cell, directly or indirectly by introduction into a precursor of the cell, by way of deliberate genetic manipulation, such as by microinjection or by infection with a recombinant virus.

Preferably, the transgenic non-human mammal overexpressing the polynucleotide encoding the FPRL2 polypeptide receptor according to the invention comprises the polynucleotide incorporated in a DNA construct with an inducible promoter allowing the overexpression of the receptor and possibly also tissue and cell-specific regulatory elements.

In one embodiment, the kits according to the invention comprise reagents for measuring the binding of a HBP polypeptide to a FPRL2 polypeptide. In another embodiment, the kit comprises reagents for measuring a signalling activity of a FPRL2 polypeptide.

In one embodiment, a screening or diagnostic kit according to the invention includes a FPRL2 receptor polypeptide or a cellular membrane preparation comprising a FPRL2 polypeptide and one or more HBP polypeptide in separate containers. Such kits can additionally comprise all the necessary means and media for performing a detection of specific binding (for example of HBP polypeptide) to the FPRL2 polypeptide receptor according to the invention. Binding or signalling activity can be correlated with a method of monitoring one or more of the symptoms of the diseases described hereafter.

The diagnostic kits can thus further comprise elements necessary for a specific diagnostic measurement, or, for example, the measurements of bound compounds using high throughput screening techniques known to the person skilled in the art, e.g., the techniques described in WO 00/02045. Such kits can be used, e.g. to monitor dosage and effectiveness of FPRL2 polypeptide modulating agents used for treatment. The high throughput screening diagnostic dosage and monitoring can be performed by using various solid supports, such as microtiter plates or biochips selected by the person skilled in the art.

In a pharmaceutical composition according to the invention, the adequate pharmaceutical carrier is a carrier of solid, liquid or gaseous form, which can be selected by the person skilled in the art according to the type of administration and the possible side effects of the compound administered to modulate FPRL2 polypeptide activity. The pharmaceutical carrier useful according to the invention does not include tissue culture medium or other media comprising serum. The ratio between the pharmaceutical carrier and the specific compound can be selected by the person skilled in the art according to the patient treated, the administration and the possible side effects of the compound, as well as the type of disease of disorder treated or sought to be prevented.

The pharmaceutical composition finds advantageous applications in the field of treatment and/or prevention of various diseases or disorders, preferably selected from the group consisting of cell migration, cancer, development of tumours and tumour metastasis, inflammatory and neoplastic processes, wound and bone healing and dysfunction of regulatory growth functions, obesity, anorexia, bulimia, acute heart failure, hypotension, hypertension, urinary retention, osteoporosis, angina pectoris, restenosis, atherosclerosis, thrombosis and other cardiovascular diseases, autoimmune and, diseases characterized by excessive smooth muscle cell proliferation, aneurysms, diseases characterized by loss of smooth muscle cells or reduced smooth muscle cell proliferation, stroke, ischemia, ulcers, allergies, prostatic hypertrophy, migraine, vomiting, psychotic and neurological disorders, including anxiety, schizophrenia, manic depression, depression, delirium, dementia and severe mental retardation, degenerative diseases, neurodegenerative diseases such as Alzheimer's disease or Parkinson's disease, and dyskinasias, such as Huntington's disease or Gilles de la Tourett's syndrome and other related diseases including thrombosis and other cardiovascular diseases, autoimmune and inflammatory diseases such as psoriasis, Eczeme, inflammatory and trophic diseases of skin, rheumatoid arthritis, scleroderma, lupus, polymyositis, dermatomysitis, Crohn's disease, inflammatory bowel disease (IBD), Irritable Bowel Syndrome, Ulcerative Colitis, Asthma, Chronic Obstructive Pulmonary Disease, Allergic Rhinitis, Fibromyalgia, Organ Transplant Rejection, Graft versus host disease, Multiple Sclerosis, Acute, Ischemic Stroke, Infectious diseases, Hepatitis A, Hepatitis B, Hepatitis C, Sepsis, Septic shock, Chronic bronchitis, infections such as bacterial, fungal, protozoan and viral infections, such as infections caused by HIV1 and HIV2, and pain, cancer, anorexia, bulimia, asthma, acute heart failure, hypertension, urinary retention, osteoporosis, angina pectoris, myocardial infarction, ulcers, allergies, benign prostatic hypertrophy, and Type 1 Diabetes, Type 2 Diabetes, Osteoarthritis, Diabetic Retinopathy, Diabetic Nephropathy and fertility dysfunctions, foetal developmental disorders Among the mentioned diseases the preferred applications are related to therapeutic agents targeting 7TM receptors that can play a function in preventing, improving or correcting dysfunctions or diseases, including, but not limited to cell migration, cancer, development of tumours and tumour metastasis, inflammatory and neoplastic processes, wound and bone healing and dysfunction of regulatory growth functions, obesity, anorexia, bulimia, acute heart failure, hypotension, hypertension, urinary retention, osteoporosis, angina pectoris, restenosis, atherosclerosis, thrombosis and other cardiovascular diseases, autoimmune and, diseases characterized by excessive smooth muscle cell proliferation, aneurysms, diseases characterized by loss of smooth muscle cells or reduced smooth muscle cell proliferation, stroke, ischemia, ulcers, allergies, prostatic hypertrophy, migraine, vomiting, psychotic and neurological disorders, including anxiety, schizophrenia, manic depression, depression, delirium, dementia and severe mental retardation, degenerative diseases, neurodegenerative diseases such as Alzheimer's disease or Parkinson's disease, and dyskinasias, such as Huntington's disease or Gilles de la Tourett's syndrome and other related diseases including thrombosis and other cardiovascular diseases, autoimmune and inflammatory diseases such as psoriasis, Eczeme, inflammatory and trophic diseases of skin, rheumatoid arthritis, scleroderma, lupus, polymyositis, dermatomysitis, Crohn's disease, inflammatory bowel disease (IBD), Irritable Bowel Syndrome, Ulcerative Colitis, Asthma, Chronic Obstructive Pulmonary Disease, Allergic Rhinitis, Fibromyalgia, Organ Transplant Rejection, Graft versus host disease, Multiple Sclerosis, Acute, Ischemic Stroke, Infectious diseases, Hepatitis A, Hepatitis B, Hepatitis C, Sepsis, Septic shock, Chronic bronchitis, infections such as bacterial, fungal, protozoan and viral infections, such as infections caused by HIV1 and HIV2, and pain, cancer, anorexia, bulimia, asthma, acute heart failure, hypertension, urinary retention, osteoporosis, angina pectoris, myocardial infarction, ulcers, allergies, benign prostatic hypertrophy, and Type 1 Diabetes, Type 2 Diabetes, Osteoarthritis, Diabetic Retinopathy, Diabetic Nephropathy and fertility dysfunctions, foetal developmental disorders.

The invention further encompasses an agent which modulates FPRL2 polypeptide activity identified by the method or detected in a sample as mentioned above.

The invention further encompasses the use of said agent for the modulation of FPRL2 polypeptide activity.

The invention further encompasses the use of said agent for the manufacture of a medicament for the treatment of FPRL2 polypeptide-related diseases or for the manufacture of a kit for the modulation of FPRL2 polypeptide activity.

The invention further encompasses a pharmaceutical composition comprising an adequate pharmaceutical carrier or diluent and a sufficient amount of said agent.

The invention further encompasses a pharmaceutical composition according to according to the above-mentioned, further comprising a vesicle or an adjuvant able to modulate the immune response of a patient to which it is administered.

The invention further encompasses the use of the above-mentioned pharmaceutical composition for the manufacture of a medicament for the treatment of FPRL2 polypeptide-related diseases or for the manufacture of a kit for the modulation of FPRL2 polypeptide.

The invention also relates to the use of a HBP polypeptide for the modulation of FPRL2 polypeptide activity in vivo and/or in vitro.

The invention also relates to the use of a HBP polypeptide in the validation of a non-human mammal comprising a partial or total deletion of the polynucleotide encoding FPRL2 polypeptide.

The invention also relates to the use of a HBP polypeptide in the validation of a non-human mammal overexpressing the polynucleotide encoding FPRL2 polypeptide.

As used herein, an "antagonist" is a ligand which competitively binds to a receptor at the same site as an agonist, but does not activate an intracellular response initiated by an active form of the receptor. An antagonist thereby inhibits the intracellular response induced by an agonist, for example HBP polypeptide, by at least 10%, preferably 15-25%, more preferably 25-50% and most preferably, 50-100%, as compared to the intracellular response in the presence of an agonist and in the absence of an antagonist.

As used herein, an "agonist" refers to a ligand that activates an intracellular response when it binds to a receptor at concentrations equal to or lower than HBP polypeptide concentrations which induce an intracellular response. An agonist according to the invention can increase the intracellular response mediated by a receptor by at least 2-fold, preferably 5-fold, more preferably 10-fold and most preferably 100-fold or more (i.e., 150-fold, 200-fold, 30 250-fold, 500-fold, 1000-fold, 10,000-fold etc . . . ), as compared to the intracellular response in the absence of agonist. An agonist according to the invention may promotes internalization of a cell surface receptor such that the cell surface expression of a receptor is increased by at least 2-fold, preferably 5-fold, more preferably 10-fold and most preferably, 100-fold or more (i.e., 150-fold, 200-fold, 250-fold, 500-fold, 1000-fold, 10,000-fold etc . . . ), as compared to the number of cell surface receptors present on the surface of a cell in the absence of an agonist. In another embodiment of the invention, an agonist stablizes a cell surface receptor and increases the cell surface expression of a receptor by at least 2-fold, preferably 5-fold, more preferably 10-fold and most preferably, 100-fold or more (i.e., 200-fold, 250-fold, 500-fold, 1000-fold, 10,000-fold etc . . . ), as compared to the number of cell surface receptors present on the surface of a cell in the absence of agonist.

As used herein, an "inverse agonist" refers to a ligand which decreases a constitutive activity of a cell surface receptor when it binds to a receptor. An inverse agonist according to the invention can decrease the constitutive intracellular response mediated by a receptor by at least 2-fold, preferably 5-fold, more preferably 10-fold and most preferably 100-fold or more (i.e., 150-fold, 200-fold, 250-fold, 500-fold, 1000-fold, 10,000-fold etc . . . ), as compared to the intracellular response in the absence of inverse agonist.

An "inhibitor" compound according to the invention is a molecule directed against the receptor or against the natural ligand for the receptor that decreases the binding of the ligand to the receptor by at least 10%, preferably 15-25%, more preferably 25-50% and most preferably, 50-100%, in the presence of HBP polypeptide, as compared to the binding in the presence of HBP polypeptide and in the absence of inhibitor. An "inhibitor" compound of the invention can decrease the intracellular response induced by an agonist, for example HBP polypeptide, by at least 10%, preferably 15-25%, more preferably 25-50% and most preferably, 50-100%. An "inhibitor" also refers to a nucleotide sequence encoding an inhibitor compound of the invention. An inhibitor, useful according to the present invention, includes, but is not limited to an antibody which specifically binds to at least a portion of FPRL2 polypeptide which is required for signal transduction through FPRL2 polypeptide (such as the ligand binding site), or chemical compounds which are capable of blocking or reducing (e.g., by at least 10%) the signal transduction pathway which is coupled to the FPRL2 polypeptide receptor. Such inhibitors include, but are not limited to sub-lethal doses of pertussis toxin, N-ethylnaleimide (NEM; Sigma), dibutyryl cAMP (Boehringer Mannheim, Corp.), and H-89 (N-[2-((p-bromocinnamyl)amino)ethyl]-5-isoquinolinesulfona-mide-HCL; Calbiochem).

As used herein, "natural ligand" refers to a naturally occurring ligand, found in nature, which binds to a receptor in a manner that is at least equivalent to HBP polypeptide. A "natural ligand" does not refer to an engineered ligand that is not found in nature and that is engineered to bind to a receptor, where it did not formerly do so in a manner different, either in degree or kind, from that which it was engineered to do. Such an engineered ligand is no longer naturally-occurring but is "non-natural" and is derived from a naturally occurring molecule.

As used herein, a "modulator" refers to a compound that increases or decreases the cell surface expression of a receptor of the invention, increases or decreases the binding of a ligand to a receptor of the invention, or any compound that increases or decreases the intracellular response initiated by an active form of the receptor of the invention, either in the presence or absence or an agonist, and in the presence of a ligand for the receptor, for example HBP polypeptide. A modulator includes an agonist, antagonist, inhibitor or inverse agonist, as defined herein. A modulator can be for example, a polypeptide, a peptide, an antibody or antigen-binding fragment thereof, a lipid, a carbohydrate, a nucleic acid, and a small organic molecule. Candidate modulators can be natural or synthetic compounds, including, for example, synthetic small molecules, compounds contained in extracts of animal, plant, bacterial or fungal cells, as well as conditioned medium from such cells.

As used herein, "increase" and "decrease" refer to a change in ligand binding to the FPRL2 polypeptide receptor and/or cell signalling through FPRL2 polypeptide of at least 10%. An "increase" or "decrease" in binding or signalling is preferably measured in response to contacting FPRL2 polypeptide with a ligand in the presence of a candidate modulator, wherein the change in binding or signalling is relative to the binding or signalling in the absence of the candidate modulator.

As used herein, the term "small molecule" refers to a compound having molecular mass of less than 3000 Daltons, preferably less than 2000 or 1500, still more preferably less than 1000, and most preferably less than 600 Daltons. A "small organic molecule" is a small molecule that comprises carbon.

As used herein, the terms "change", "difference", "decrease", or "increase" as applied to e.g., binding or signalling activity or amount of a substance refer to an at least 10% increase or decrease in binding, signalling activity, or for example, level of mRNA, polypeptide or ligand relative to a standard in a given assay.

As used herein, the term "dysregulation" refers to the signalling activity of FPRL2 polypeptide in a sample wherein:

a) a 10% or greater increase or decrease in the amount of one or more of FPRL2 polypeptide, ligand or mRNA level is measured relative to a standard, as defined herein, in a given assay or;

b) at least a single base pair change in the FPRL2 polypeptide coding sequence is detected relative to SEQ ID NO: 1, and results in an alteration of FPRL2 polypeptide ligand binding or signalling activity as defined in paragraphs a), c) or d) or;

c) a 10% or greater increase or decrease in the amount of FPRL2 polypeptide ligand binding activity is measured relative to a standard, as defined herein, in a given assay or;

d) a 10% or greater increase or decrease in a second messenger, as defined herein, is measured relative to the standard, as defined herein, in a given assay.

As used herein, the term "conditions permitting the binding of HBP polypeptide to a FPRL2 polypeptide" refers to conditions of, for example, temperature, salt concentration, pH and protein concentration under which FPRL2, binds FPRL2 polypeptide. Exact binding conditions will vary depending upon the nature of the assay, for example, whether the assay uses viable cells or only a membrane fraction of cells. However, because FPRL2 polypeptide is a cell surface protein favored conditions will generally include physiological salt (90 mM) and pH (about 7.0 to 8.0). Temperatures for binding can vary from 15° C. to 37° C., but will preferably be between room temperature and about 30° C. The concentration of HBP polypeptide in a binding reaction will also vary, but will preferably be about 10 pM to 10 nM (e.g., in a reaction with radiolabelled tracer HBP polypeptide).

As used herein, the term "sample" refers to the source of molecules being tested for the presence of an agent or modulator compound that modulates binding to or signalling activity of a FPRL2 polypeptide. A sample can be an environmental sample, a natural extract of animal, plant yeast or bacterial cells or tissues, a clinical sample, a synthetic sample, or a conditioned medium from recombinant cells or a fermentation process. The term "tissue sample" refers to a tissue that is tested for the presence, abundance, quality or an activity of a FPRL2 polypeptide, a nucleic acid encoding a FPRL2 polypeptide, a FPRL2 ligand or an agent or compound that modifies the ligand binding or activity of a FPRL2 polypeptide.

As used herein, a "tissue" is an aggregate of cells that perform a particular function in an organism. The term "tissue" as used herein refers to cellular material from a particular physiological region. The cells in a particular tissue can comprise several different cell types. A non-limiting example of this would be brain tissue that further comprises neurons and glial cells, as well as capillary endothelial cells and blood cells, all contained in a given tissue section or sample. In addition to solid tissues, the term "tissue" is also intended to encompass non-solid tissues, such as blood.

As used herein, the term "membrane fraction" refers to a preparation of cellular lipid membranes comprising a FPRL2 polypeptide. As the term is used herein, a "membrane fraction" is distinct from a cellular homogenate, in that at least a portion (i.e., at least 10%, and preferably more) of non-membrane-associated cellular constituents has been removed. The term "membrane associated" refers to those cellular constituents that are either integrated into a lipid membrane or are physically associated with a component that is integrated into a lipid membrane.

As used herein, the "second messenger assay" preferably comprises the measurement of guanine nucleotide binding or exchange, adenylate cyclase, intra-cellular cAMP, intracellular inositol phosphate, intra-cellular diacylglycerol concentration, arachidonic acid concentration, MAP kinase(s) or tyrosine kinase(s), protein kinase C activity, or reporter gene expression or an aequorin-based assay according to methods known in the art and defined herein.

As used herein, the term "second messenger" refers to a molecule, generated or caused to vary in concentration by the activation of a G-Protein Coupled Receptor, that participates in the transduction of a signal from that GPCR. Non-limiting examples of second messengers include cAMP, diacylglycerol, inositol trisphosphate, arachidonic acid release, and intracellular calcium. The term "change in the level of a second messenger" refers to an increase or decrease of at least 10% in the detected level of a given second messenger relative to the amount detected in an assay performed in the absence of a candidate modulator.

As used herein, the term "aequorin-based assay" refers to an assay for GPCR activity that measures intracellular calcium flux induced by activated GPCRs, wherein intracellular calcium flux is measured by the luminescence of aequorin expressed in the cell.

As used herein, the term "binding" refers to the physical association of a ligand (e.g., a ligand such as HBP polypeptide, or an antibody) with a receptor (e.g., FPRL2). As the term is used herein, binding is "specific" if it occurs with an $EC_{50}$ or a $K_d$ of 1 mM less, generally in the range of 100 nM to 10 pM For example, binding is specific if the $EC_{50}$ or $K_d$ is 100 nM, 50 nM, 10 nM, 1 nM, 950 pM, 900 pM, 850 pM, 800 pM, 750 pM, 700 pM, 650 pM, 600 pM, 550 pM, 500 pM, 450 pM, 350 pM, 300 pM, 250 pM, 200 pM, 150 pM, 100 pM, 75 pM, 50 pM, 25 pM, 10 pM or less.

As used herein, the term "$EC_{50}$," refers to that concentration of a compound at which a given activity, including binding of HBP polypeptide or other ligand and a functional activity of a receptor polypeptide, is 50% of the maximum for that receptor activity measurable using the same assay in the absence of compound. Stated differently, the "$EC_{50}$" is the concentration of compound that gives 50% activation, when 100% activation is set at the amount of activity that does not increase with the addition of more agonist. It should be noted that the "$EC_{50}$" of an analog of HBP polypeptide will vary according to the identity of the analogue used in the assay; for example, HBP polypeptide analogues can have $EC_{50}$ values higher than, lower than or the same as HBP polypeptide. Therefore, where a HBP polypeptide analogue differs from HBP polypeptide, one of skill in the art can determine the $EC_{50}$ for that analogue according to conventional methods. The $EC_{50}$ of a given HBP polypeptide analogue is measured by performing an assay for the activity of a fixed amount of FPRL2 polypeptide polypeptide in the presence of doses of HBP polypeptide analogues that increase at least until the FPRL2 polypeptide response is saturated or maximal, and then plotting the measured FPRL2 polypeptide activity versus the concentration of HBP polypeptide analogues.

As used herein, the term "saturation" refers to the concentration of HBP polypeptide or other ligand at which further increases in ligand concentration fail to increase the binding of ligand or FPRL2 polypeptide-specific signalling activity.

As used herein, the term "$IC_{50}$" is the concentration of an antagonist or inverse agonist that reduces the maximal activation of a FPRL2 polypeptide receptor by 50%.

As used herein, the term "LD50" refers to the dose of a particular agent necessary to kill 50% of the subjects to which it is administered.

As used herein, the term "decrease in binding" refers to a decrease of at least 10% in the amount of ligand binding detected in a given assay with a known or suspected modulator of FPRL2 polypeptide relative to binding detected in an assay lacking that known or suspected modulator.

As used herein, the term "delivering," when used in reference to a drug or agent, means the addition of the drug or agent to an assay mixture, or to a cell in culture. The term also refers to the administration of the drug or agent to an animal. Such administration can be, for example, by injection (in a suitable carrier, e.g., sterile saline or water) or by inhalation, or by an oral, transdermal, rectal, vaginal, or other common route of drug administration.

As used herein, the term "standard" refers to a sample taken from an individual who is not affected by a disease or disorder characterized by dysregulation of FPRL2 polypeptide activity. The "standard" is used as a reference for the comparison of FPRL2 mRNA or polypeptide levels and quality (i.e., mutant vs. wild type), as well as for the comparison of FPRL2 polypeptide activities. A "standard" also encompasses a reference sequence, e.g., SEQ ID NO: 1 or SEQ ID NO: 2, with which sequences of nucleic acids or their encoded polypeptides are compared.

As used herein, the term "amplifying," when applied to a nucleic acid sequence, refers to a process whereby one or more copies of a nucleic acid sequence is generated from a template nucleic acid. A preferred method of "amplifying" is PCR or RT/PCR.

As used herein, the term "G-Protein coupled receptor," or "GPCR" refers to a membrane-associated polypeptide with 7 alpha helical transmembrane domains. Functional GPCR's associate with a ligand or agonist and also associate with and activate G-proteins. FPRL2 polypeptide is a GPCR.

As used herein, the term "antibody" is the conventional immunoglobulin molecule, as well as fragments thereof which are also specifically reactive with one of the subject polypeptides. Antibodies can be fragmented using conventional techniques and the fragments screened for utility in the same manner as described herein below for whole antibodies. For example, F(ab)$_2$ fragments can be generated by treating antibody with pepsin. The resulting F(ab)$_2$ fragment can be treated to reduce disulfide bridges to produce Fab fragments. The antibody of the present invention is further intended to include bispecific, single-chain, and chimeric and humanised molecules having affinity for a polypeptide conferred by at least one CDR region of the antibody. In preferred embodiments, the antibody further comprises a label attached thereto and able to be detected, (e.g., the label can be a radioisotope, fluorescent compound, chemiluminescent compound, enzyme, or enzyme co-factor). The antibodies, monoclonal or polyclonal and its hypervariable portion thereof (F(ab), F(ab') 2, etc.) as well as the hybridoma cell producing the antibodies are a further aspect of the present invention which find a specific industrial application in the field of diagnostics and monitoring of specific diseases, preferably the ones hereafter described.

Inhibitors and modulators according to the invention include but are not limited to monoclonal or polygonal antibodies or hypervariable portions of the antibodies.

The term "humanized immunoglobulin" as used herein refers to an immunoglobulin comprising portions of immunoglobulins of a different origin, wherein at least one portion is of human origin. Accordingly, the present invention relates to a humanized immunoglobulin which binds human FPRL2, said immunoglobulin comprising an antigen-binding region of nonhuman origin (e.g., rodent) and at least a portion of an immunoglobulin of human origin (e.g., a human framework region, a human constant region or portion thereof). For example, the humanized antibody can comprise portions derived from an immunoglobulin of nonhuman origin with the requisite specificity, such as a mouse, and from immunoglobulin sequences of human origin (e.g., a chimeric immunoglobulin), joined together chemically by conventional techniques (e.g., synthetic) or prepared as contiguous polypeptide using genetic engineering techniques (e.g., DNA encoding the protein portions of the chimeric antibody can be expresses to produce a contiguous polypeptide chain). Another example of a humanized immunoglobulin of the present invention is an immunoglobulin containing one or more immunoglobulin chains comprising a CDR of nonhuman origin (e.g., one or more CDRs derived from an antibody of nonhuman origin) and a framework region derived from a light and/or heavy chain of human origin (e.g., CDR-grafted antibodies with or without framework changes).

Such humanized immunoglobulins can be produced using synthetic and/or recombinant nucleic acids to prepare genes (e.g., cDNA) encoding the desired humanized chain. For example, nucleic acid (e.g., DNA) sequences coding for humanized variable regions can be constructed using PCR mutagenesis methods to alter DNA sequences encoding a human or humanized chain, such as a DNA template form a previously humanized variable region (see e.g., Kamman, M., et al., Nucleic Acids Res., 17: 5404 (1989); Sato, K., et al., Cancer Research, 53: 851-856 (1993); Daugherty, B. L. et al., Nucleic Acids Res., 19(9): 2471-2476 (1991); and Lewis, A. P. and J. S Crowe, Gene, 101: 297-302 (1991)). Using these or other suitable methods, variants can also be readily produced. In one embodiment, cloned variable regions can be mutagenized, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993; Knappik et al., WO 97/08320, published Mar. 6, 1997)).

As used herein, the term "transgenic animal" refers to any animal, preferably a non-human mammal, bird, fish or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical crossbreeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of the subject polypeptide, e.g. either agonistic or antagonistic forms. However, transgenic animals in which the recombinant gene is silent are also contemplated, as for example, the FLP or CRE recombinase dependent constructs described below. Moreover, "transgenic animal" also includes those recombinant animals in which gene disruption of one or more genes is caused by human intervention, including both recombination and antisense techniques.

Sequences

The invention relates to the nucleotide (SEQ ID NO: 1) and amino acid (SEQ ID NO: 2) sequences encoding FPRL2 polypeptide (presented in FIG. 1). The invention also relates to sequences that are homologous to the nucleotide and amino acid sequences encoding FPRL2 polypeptide.

Calculation of Sequence Homology

Sequence identity with respect to any of the sequences presented herein can be determined by a simple "eyeball" comparison (i.e. a strict comparison) of any one or more of the sequences with another sequence to see if that other sequence has, for example, at least 80% sequence identity to the sequence(s).

Relative sequence identity can also be determined by commercially available computer programs that can calculate % identity between two or more sequences using any suitable algorithm for determining identity, using for example default parameters. A typical example of such a computer program is CLUSTAL. Other computer program methods to determine identity and similarity between two sequences include but are not limited to the GCG program package (Devereux et al 1984 Nucleic Acids Research 12: 387) and FASTA (Atschul et al 1990 J Molec Biol 403-410).

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example, when using the GcG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software that can perform sequence comparisons include, but are not limited to, the BLAST package (Ausubel et al., 1995, *Short Protocols in Molecular Biology*, 3rd Edition, John Wiley & Sons), FASTA (Atschul et al., 1990, J. Mol. Biol., 403-410) and the GENEWORKS suite of comparison tools. Both BLAST and FASTA are available for offline and online searching (Ausubel et al., 1999 supra, pages 7-58 to 7-60).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied. It is preferred to use the public default values for the GCG package, or in the case of other software, the default matrix, such as BLOSUM62.

Advantageously, the BLAST algorithm is employed, with parameters set to default values. The BLAST algorithm is described in detail at http://www.ncbi.nih.gov/BLAST/blast_help.html, which is incorporated herein by reference. The search parameters are defined as follows, and can be advantageously set to the defined default parameters.

Advantageously, "substantial identity" when assessed by BLAST equates to sequences which match with an EXPECT value of at least about 7, preferably at least about 9 and most preferably 10 or more. The default threshold for EXPECT in BLAST searching is usually 10.

BLAST (Basic Local Alignment Search Tool) is the heuristic search algorithm employed by the programs blastp, blastn, blastx, tblastn, and tblastx; these programs ascribe significance to their findings using the statistical methods of Karlin and Altschul (Karlin and Altschul 1990, *Proc. Natl. Acad. Sci. USA* 87:2264-68; Karlin and Altschul, 1993, *Proc. Natl. Acad. Sci. USA* 90:5873-7; see http://www.ncbi.nih.gov/BLAST/blast_help.html) with a few enhancements. The BLAST programs are tailored for sequence similarity searching, for example to identify homologues to a query sequence. For a discussion of basic issues in similarity searching of sequence databases, see Altschul et al (1994) Nature Genetics 6:119-129.

The five BLAST programs available at http://www.ncbi.nlm.nih.gov perform the following tasks: blastp—compares an amino acid query sequence against a protein sequence database; blastn—compares a nucleotide query sequence against a nucleotide sequence database; blastx—compares the six-frame conceptual translation products of a nucleotide query sequence (both strands) against a protein sequence database; tblastn—compares a protein query sequence against a nucleotide sequence database dynamically translated in all six reading frames (both strands); tblastx—compares the six-frame translations of a nucleotide query sequence against the six-frame translations of a nucleotide sequence database.

BLAST uses the following search parameters:

HISTOGRAM—Display a histogram of scores for each search; default is yes. (See parameter H in the BLAST Manual).

DESCRIPTIONS—Restricts the number of short descriptions of matching sequences reported to the number specified; default limit is 100 descriptions. (See parameter V in the manual page).

EXPECT—The statistical significance threshold for reporting matches against database sequences; the default value is 10, such that 10 matches are expected to be found merely by chance, according to the stochastic model of Karlin and Altschul (1990). If the statistical significance ascribed to a match is greater than the EXPECT threshold, the match will not be reported. Lower EXPECT thresholds are more stringent, leading to fewer chance matches being reported. Fractional values are acceptable. (See parameter E in the BLAST Manual).

CUTOFF—Cutoff score for reporting high-scoring segment pairs. The default value is calculated from the EXPECT value (see above). HSPs are reported for a database sequence only if the statistical significance ascribed to them is at least as high as would be ascribed to a lone HSP having a score equal to the CUTOFF value. Higher CUTOFF values are more stringent, leading to fewer chance matches being reported. (See parameter S in the BLAST Manual). Typically, significance thresholds can be more intuitively managed using EXPECT.

ALIGNMENTS—Restricts database sequences to the number specified for which high-scoring segment pairs (HSPs) are reported; the default limit is 50. If more database sequences than this happen to satisfy the statistical significance threshold for reporting (see EXPECT and CUTOFF below), only the matches ascribed the greatest statistical significance are reported. (See parameter B in the BLAST Manual).

MATRIX—Specify an alternate scoring matrix for BLASTP, BLASTX, TBLASTN and TBLASTX. The default matrix is BLOSUM62 (Henikoff & Henikoff, 1992). The valid alternative choices include: PAM40, PAM120, PAM250 and IDENTITY. No alternate scoring matrices are available for BLASTN; specifying the MATRIX directive in BLASTN requests returns an error response.

STRAND—Restrict a TBLASTN search to just the top or bottom strand of the database sequences; or restrict a BLASTN, BLASTX or TBLASTX search to just reading frames on the top or bottom strand of the query sequence.

FILTER—Mask off segments of the query sequence that have low compositional complexity, as determined by the SEG program of Wootton & Federhen (1993) Computers and Chemistry 17:149-163, or segments consisting of short-periodicity internal repeats, as determined by the XNU program of Claverie & States (1993) Computers and Chemistry 17:191-201, or, for BLASTN, by the DUST program of Tatusov and Lipman (see http://www.ncbi.nlm.nih.gov). Filtering can eliminate statistically significant but biologically uninteresting reports from the blast output (e.g., hits against common acidic-, basic- or proline-rich regions), leaving the more biologically interesting regions of the query sequence available for specific matching against database sequences.

Low complexity sequence found by a filter program is substituted using the letter "N" in nucleotide sequence (e.g., "NNNNNNNNNNNNN") and the letter "X" in protein sequences (e.g., "XXXXXXXXX").

Filtering is only applied to the query sequence (or its translation products), not to database sequences. Default filtering is DUST for BLASTN, SEG for other programs.

It is not unusual for nothing at all to be masked by SEG, XNU, or both, when applied to sequences in SWISS-PROT, so filtering should not be expected to always yield an effect. Furthermore, in some cases, sequences are masked in their entirety, indicating that the statistical significance of any matches reported against the unfiltered query sequence should be suspect.

NCBI-gi—Causes NCBI gi identifiers to be shown in the output, in addition to the accession and/or locus name.

Most preferably, sequence comparisons are conducted using the simple BLAST search algorithm provided at http://www.ncbi.nlm.nih.gov/BLAST. In some embodiments of the present invention, no gap penalties are used when determining sequence identity.

Cells

A cell that is useful according to the invention is preferably selected from the group consisting of bacterial cells, yeast cells, insect cells or mammalian cells.

A cell that is useful according to the invention can be any cell into which a nucleic acid sequence encoding a receptor according to the invention can be introduced such that the receptor is expressed at natural levels or above natural levels, as defined herein. Preferably a receptor of the invention that is expressed in a cell exhibits normal or near normal pharmacology, as defined herein. Most preferably a receptor of the invention that is expressed in a cell comprises the nucleotide represented by SEQ ID NO: 1 or amino acid sequence represented by by SEQ ID NO: 2 or a nucleotide or amino acid sequence that is at least 70% identical to the amino acid sequence represented by SEQ ID NO: 2. Preferably, a receptor of the invention that is expressed in a cell will bind HBP polypeptide.

According to a preferred embodiment of the present invention, a cell is selected from the group consisting of COS7-cells, a CHO cell, a LM (TK-) cell, a NIH-3T3 cell, HEK-293 cell, K-562 cell or a 1321N1 astrocytoma cell but also other transfectable cell lines.

Assays

I. Assays for the Identification of Agents that Modulate the Activity of FPRL2 Polypeptide Agents that modulate the activity of FPRL2 polypeptide can be identified in a number of ways that take advantage of the newly discovered interaction of the receptor with HBP polypeptide. For example, the ability to reconstitute FPRL2 polypeptide/HBP polypeptide binding either in vitro, on cultured cells or in vivo provides a target for the identification of agents that disrupt that binding. Assays based on disruption of binding can identify agents, such as small organic molecules, from libraries or collections of such molecules. Alternatively, such assays can identify agents in samples or extracts from natural sources, e.g., plant, fungal or bacterial extracts or even in human tissue samples (e.g., tumor tissue). In one aspect, the extracts can be made from cells expressing a library of variant nucleic acids, peptides or polypeptides. Modulators of FPRL2 polypeptide/HBP polypeptide binding can then be screened using a binding assay or a functional assay that measures downstream signalling through the receptor.

Another approach that uses the FPRL2 polypeptide/HBP polypeptide interaction more directly to identify agents that modulate FPRL2 polypeptide function measures changes in FPRL2 polypeptide downstream signalling induced by candidate agents or candidate modulators. These functional assays can be performed in isolated cell membrane fractions or on cells expressing the receptor on their surfaces.

The finding that HBP polypeptide is a ligand of the FPRL2 polypeptide receptor permits screening assays to identify agonists, antagonists and inverse agonists of receptor activity. The screening assays have two general approaches, detailed below. For the purposes of this section HBP polypeptide (SED ID NO: 18) is used as an exemplary ligand. It should be understood, however, that any HBP polypeptide as defined herein can be used in the assays described.

1) Ligand binding assays, in which cells expressing FPRL2 polypeptide, membrane extracts from such cells, or immobilized lipid membranes comprising FPRL2 polypeptide are exposed to labelled and candidate compound. Following incubation, the reaction mixture is measured for specific binding of the labelled to the FPRL2 polypeptide receptor. Compounds that interfere with binding or displace labelled can be agonists, antagonists or inverse agonists of FPRL2 polypeptide activity. Subsequent functional analysis can then be performed on positive compounds to determine in which of these categories they belong.

2) Functional assays, in which a signalling activity of FPRL2 polypeptide is measured.

a) For agonist screening, cells expressing FPRL2 polypeptide or membranes prepared from them are incubated with a candidate compound, and a signalling activity of FPRL2 polypeptide is measured. The activity induced by compounds that modulate receptor activity is compared to that induced by the natural ligand, an HBP polypeptide. An agonist or partial agonist will have a maximal biological activity corresponding to at least 10% of the maximal activity of HBP polypeptide when the agonist or partial agonist is present at 1 mM or less, and preferably will have a potency which is at least as potent as HBP polypeptide.

b) For antagonist or inverse agonist screening, cells expressing FPRL2 polypeptide or membranes isolated from them are assayed for signalling activity in the presence of HBP polypeptide with or without a candidate compound. Antagonists will reduce the level of HBP polypeptide-stimulated receptor activity by at least 10%, relative to reactions lacking the antagonist in the presence of HBP polypeptide. Inverse agonists will reduce the constitutive activity of the receptor by at least 10%, relative to reactions lacking the inverse agonist.

c) For inverse agonist screening, cells expressing constitutive FPRL2 polypeptide activity or membranes isolated from them are used in a functional assay that measures an activity of the receptor in the presence of a candidate compound. Inverse agonists are those compounds that reduce the constitutive activity of the receptor by at least 10%. Overexpression of FPRL2 polypeptide may lead to constitutive activation. FPRL2 polypeptide can be overexpressed by placing it under the control of a strong constitutive promoter, e.g., the CMV early promoter. Alternatively, certain mutations of conserved GPCR amino acids or amino acid domains tend to lead to constitutive activity. See for example: Kjelsberg et al., 1992, J. Biol. Chem. 267:1430; McWhinney et al., 2000. J. Biol. Chem. 275:2087; Ren et al., 1993, J. Biol. Chem. 268:16483; Samama et al., 1993, J.Biol.Chem 268:4625; Parma et al., 1993, Nature 365:649; Parma et al., 1998, J. Pharmacol. Exp.Ther. 286:85; and Parent et al., 1996, J. Biol. Chem. 271:7949.

Ligand Binding and Displacement Assays:

As noted in (1) above, one can use FPRL2 polypeptides expressed on a cell, or isolated membranes containing receptor polypeptides, along with HBP polypeptide in order to screen for compounds that inhibit the binding of HBP polypeptide to FPRL2 polypeptide. For the purposes of this section, HBP polypeptide (SEQ ID NO: 18) is used as an exemplary ligand. It should be understood however that any HBP polypeptide as defined herein can be used in the assays described.

For displacement experiments, cells expressing a FPRL2 polypeptide (generally 25,000 cells per assay or 1 to 100 µg of membrane extracts) are incubated in binding buffer with labelled HBP polypeptide in the presence or absence of increasing concentrations of a candidate modulator. To validate and calibrate the assay, control competition reactions using increasing concentrations of unlabeled HBP polypeptide can be performed. After incubation, cells are washed extensively, and bound, labelled HBP polypeptide is measured as appropriate for the given label (e.g., scintillation counting, fluorescence, etc.). A decrease of at least 10% in the amount of labelled HBP polypeptide bound in the presence of candidate modulator indicates displacement of binding by the candidate modulator. Candidate modulators are considered to bind specifically in this or other assays described herein if they displace 50% of labelled HBP polypeptide (sub-saturating HBP polypeptide dose) at a concentration of 1 mM or less.

Alternatively, binding or displacement of binding can be monitored by surface plasmon resonance (SPR). Surface plasmon resonance assays can be used as a quantitative method to measure binding between two molecules by the change in mass near an immobilized sensor caused by the binding or loss of binding of HBP polypeptide from the aqueous phase to a FPRL2 polypeptide immobilized in a membrane on the sensor. This change in mass is measured as resonance units versus time after injection or removal of the HBP polypeptide or candidate modulator and is measured using a Biacore Biosensor (Biacore AB). FPRL2 polypeptide can be immobilized on a sensor chip (for example, research grade CM5 chip; Biacore AB) in a thin film lipid membrane according to methods described by Salamon et al. (Salamon et al., 1996, Biophys J. 71: 283-294; Salamon et al., 2001, Biophys. J. 80: 1557-1567; Salamon et al., 1999, Trends Biochem. Sci. 24: 213-219, each of which is incorporated herein by reference.). Sarrio et al. demonstrated that SPR can be used to detect ligand binding to the GPCR A(1) adenosine receptor immobilized in a lipid layer on the chip (Sarrio et al., 2000, Mol. Cell. Biol. 20: 5164-5174, incorporated herein by reference). Conditions for HBP polypeptide binding to FPRL2 polypeptide in an SPR assay can be fine-tuned by one of skill in the art using the conditions reported by Sarrio et al. as a starting point.

SPR can assay for modulators of binding in at least two ways. First, HBP polypeptide can be pre-bound to immobilized FPRL2 polypeptide polypeptide, followed by injection of candidate modulator at a concentration ranging from 0.1 nM to 1 µM. Displacement of the bound HPB polypeptide can be quantitated, permitting detection of modulator binding. Alternatively, the membrane-bound FPRL2 polypeptide can be pre-incubated with candidate modulator and challenged with HBP polypeptide. A difference in HBP polypeptide binding to the FPRL2 polypeptide exposed to modulator relative to that on a chip not pre-exposed to modulator will demonstrate binding or displacement of HBP polypeptide in the presence of modulator. In either assay, a decrease of 10% or more in the amount of HBP polypeptide bound in the presence of candidate modulator, relative to the amount of a HBP polypeptide bound in the absence of candidate modulator indicates that the candidate modulator inhibits the interaction of FPRL2 polypeptide and HBP polypeptide.

Another method of detecting inhibition of binding of HBP polypeptide to FPRL2 polypeptide uses fluorescence resonance energy transfer (FRET). FRET is a quantum mechanical phenomenon that occurs between a fluorescence donor (D) and a fluorescence acceptor (A) in close proximity to each other (usually <100 A of separation) if the emission spectrum of D overlaps with the excitation spectrum of A. The molecules to be tested, e.g. HBP polypeptide and a FPRL2 polypeptide, are labelled with a complementary pair of donor and acceptor fluorophores. While bound closely together by the FPRL2 polypeptide: HBP polypeptide interaction, the fluorescence emitted upon excitation of the donor fluorophore will have a different wavelength than that emitted in response to that excitation wavelength when the HBP polypeptide and FPRL2 polypeptide are not bound, providing for quantitation of bound versus unbound molecules by measurement of emission intensity at each wavelength. Donor fluorophores with which to label the FPRL2 polypeptide are well known in the art. Of particular interest are variants of the A. victoria GFP known as Cyan FP (CFP, Donor (D)) and Yellow FP (YFP, Acceptor(A)). As an example, the YFP variant can be made as a fusion protein with FPRL2 polypeptide. Vectors for the expression of GFP variants as fusions (Clontech) as well as flurophore-labeled HBP polypeptide compounds (Molecular Probes) are known in the art. The addition of a candidate modulator to the mixture of labelled HBP polypeptide and YFP-FPRL2 protein will result in an inhibition of energy transfer evidenced by, for example, a decrease in YFP fluorescence relative to a sample without the candidate modulator. In an assay using FRET for the detection of FPRL2 polypeptide: HBP polypeptide interaction, a 10% or greater decrease in the intensity of fluorescent emission at the acceptor wavelength in samples containing a candidate modulator, relative to samples without the candidate modulator, indicates that the candidate modulator inhibits the FPRL2 polypeptide: HBP polypeptide interaction.

A variation on FRET uses fluorescence quenching to monitor molecular interactions. One molecule in the interacting pair can be labelled with a fluorophore, and the other with a molecule that quenches the fluorescence of the fluorophore when brought into close apposition with it. A change in fluorescence upon excitation is indicative of a change in the association of the molecules tagged with the fluorophore: quencher pair. Generally, an increase in fluorescence of the labelled FPRL2 polypeptide is indicative that the HBP polypeptide molecule bearing the quencher has been displaced. For quenching assays, a 10% or greater increase in the intensity of fluorescent emission in samples containing a candidate modulator, relative to samples without the candidate modulator, indicates that the candidate modulator inhibits FPRL2 polypeptide: HBP polypeptide interaction.

In addition to the surface plasmon resonance and FRET methods, fluorescence polarization measurement is useful to quantitate binding. The fluorescence polarization value for a fluorescently-tagged molecule depends on the rotational correlation time or tumbling rate. Complexes, such as those formed by FPRL2 polypeptide associating with a fluorescently labelled HBP polypeptide, have higher polarization values than uncomplexed, labelled HBP polypeptide. The inclusion of a candidate inhibitor of the FPRL2 polypeptide: HBP polypeptide interaction results in a decrease in fluorescence polarization, relative to a mixture without the candidate inhibitor, if the candidate inhibitor disrupts or inhibits the interaction of FPRL2 polypeptide with HBP polypeptide. Fluorescence polarization is well suited for the identification of small molecules that disrupt the formation of receptor: ligand complexes. A decrease of 10% or more in fluorescence polarization in samples containing a candidate modulator, relative to fluorescence polarization in a sample lacking the candidate modulator, indicates that the candidate modulator inhibits FPRL2 polypeptide: HBP polypeptide interaction.

Another alternative for monitoring FPRL2 polypeptide: HBP polypeptide interactions uses a biosensor assay. ICS biosensors have been described in the art (Australian Membrane Biotechnology Research Institute; www.ambri.com.au/; Cornell B, Braach-Maksvytis V, King L, Osman P, Raguse B, Wieczorek L, and Pace R. "A biosensor that uses ion-channel switches" Nature 1997, 387, 580). In this technology, the association of FPRL2 polypeptide and its ligand is coupled to the closing of gramacidin-facilitated ion channels in suspended membrane bilayers and thus to a measurable change in the admittance (similar to impedance) of the biosensor. This approach is linear over six orders of magnitude of admittance change and is ideally suited for large scale, high throughput screening of small molecule combinatorial libraries. A 10% or greater change (increase or decrease) in admittance in a sample containing a candidate modulator, relative to the admittance of a sample lacking the candidate modulator, indicates that the candidate modulator inhibits the interaction of FPRL2 polypeptide and HBP polypeptide. It is important to note that in assays testing the interaction of FPRL2 polypeptide with HBP polypeptide, it is possible that a modulator of the interaction need not necessarily interact directly with the domain(s) of the proteins that physically interact with HBP polypeptide. It is also possible that a modulator will interact at a location removed from the site of interaction and cause, for example, a conformational change in the FPRL2 polypeptide. Modulators (inhibitors or agonists) that act in this manner are nonetheless of interest as agents to modulate the activity of FPRL2 polypeptide.

It should be understood that any of the binding assays described herein can be performed with a non-HBP polypeptide ligand (for example, agonist, antagonist, etc.) of FPRL2 polypeptide, e.g., a small molecule identified as described herein or HBP polypeptide analogues including but not limited to any of the HBP polypeptide analogues, a natural or synthetic peptide, a polypeptide, an antibody or antigen-binding fragment thereof, a lipid, a carbohydrate, and a small organic molecule.

Any of the binding assays described can be used to determine the presence of an agent in a sample, e.g., a tissue sample, that binds to the FPRL2 polypeptide receptor molecule, or that affects the binding of HBP polypeptide to the receptor. To do so, FPRL2 polypeptide is reacted with HBP polypeptide or another ligand in the presence or absence of the sample, and HBP polypeptide or ligand binding is measured as appropriate for the binding assay being used. A decrease of 10% or more in the binding of HBP polypeptide or other ligand indicates that the sample contains an agent that modulates HBP polypeptide or ligand binding to the receptor polypeptide.

Functional Assays of Receptor Activity i. GTPase/GTP Binding Assays:

For GPCRs such as FPRL2 polypeptide, a measure of receptor activity is the binding of GTP by cell membranes containing receptors. In the method described by Traynor and Nahorski, 1995, Mol. Pharmacol. 47: 848-854, incorporated herein by reference, one essentially measures G-protein coupling to membranes by detecting the binding of labelled GTP. For GTP binding assays, membranes isolated from cells expressing the receptor are incubated in a buffer containing 20 mM HEPES, pH 7.4, 100 mM NaCl, and 10 mM MgCl2, 80 pM $^{35}$S-GTPγS and 3 μM GDP. The assay mixture is incubated for 60 minutes at 30° C., after which unbound labelled GTP is removed by filtration onto GF/B filters. Bound, labelled GTP is measured by liquid or solid (SPA, see below) scintillation counting. In order to assay for modulation of HBP polypeptide-induced FPRL2 polypeptide activity, membranes prepared from cells expressing a FPRL2 polypeptide are mixed with HBP polypeptide, and the GTP binding assay is performed in the presence and absence of a candidate modulator of FPRL2 polypeptide activity. A decrease of 10% or more in labelled GTP binding as measured by scintillation counting in an assay of this kind containing a candidate modulator, relative to an assay without the modulator, indicates that the candidate modulator inhibits FPRL2 polypeptide activity. A similar GTP-binding assay can be performed without HBP polypeptide to identify compounds that act as agonists. In this case, HBP polypeptide-stimulated GTP binding is used as a standard. A compound is considered an agonist if it induces at least 50, 40, 30, or preferably 20% of the level of GTP binding induced by HBP polypeptide when the compound is present at 1 µM or less, and preferably will induce a level the same as or higher than that induced by HBP polypeptide.

Scintillation Proximity Assay (SPA) is an homogeneous screening technology applied to receptor binding assays by immobilizing receptors directly onto SPA beads via a suitable coupling method. Once immobilized, the receptor is close enough to the bead so that, should a suitably radiolabelled ligand bind to the receptor, it will be in close enough proximity to stimulate the bead to emit light. Any unbound radioligand is too distant from the bead to transfer energy and goes undetected. The bead, therefore, only detects the population of ligand molecules which are receptor bound. The discrimination of binding by proximity means that no separation of bound and free ligand is required, as in traditional methods. The method is generally applicable to [$^3$H], [$^{125}$I], [$^{35}$S] ligands. Approaches involving antibodies and biotinylation can be used for soluble receptors GTPase activity is measured by incubating the membranes containing a FPRL2 polypeptide with $\gamma^{32}$P-GTP. Active GTPase will release the label as inorganic phosphate, which is detected by separation of free inorganic phosphate in a 5% suspension of activated charcoal in 20 mM $H_3PO_4$, followed by scintillation counting. Controls include assays using membranes isolated from cells not expressing FPRL2 polypeptide (mock-transfected), in order to exclude possible non-specific effects of the candidate compound.

In order to assay for the effect of a candidate modulator on FPRL2 polypeptide-regulated GTPase activity, membrane samples are incubated with HBP polypeptide, with or without the modulator, followed by the GTPase assay. A change (increase or decrease) of 10% or more in the level of GTP binding or GTPase activity relative to samples without modulator is indicative of FPRL2 polypeptide modulation by a candidate modulator.

ii. Downstream Pathway Activation Assays:

a. Calcium Flux—The Aeguorin-based Assay.

The aequorin assay takes advantage of the responsiveness of mitochondrial apoaequorin to intracellular calcium release induced by the activation of GPCRs (Stables et al., 1997, Anal. Biochem. 252:115-126; Detheux et al., 2000, J. Exp. Med., 192 1501-1508; both of which are incorporated herein by reference). Briefly, FPRL2 polypeptide-expressing clones are transfected to coexpress mitochondrial apoaequorin and G$\alpha$16. Cells are incubated with 5 µM Coelenterazine H (Molecular Probes) for 4 hours at room temperature, washed in DMEM-F12 culture medium and resuspended at a concentration of $0.5 \times 10^6$ cells/ml. Cells are then mixed with test agonist molecules and light emission by the aequorin is recorded with a luminometer for 30 sec. Results are expressed as Relative Light Units (RLU). Controls include assays using membranes isolated from cells not expressing FPRL2 polypeptide (mock transfected), in order to exclude possible non-specific effects of the candidate compound.

Aequorin activity or intracellular calcium levels are "changed" if light intensity increases or decreases by 10% or more in a sample of cells, expressing a FPRL2 polypeptide and treated with a candidate modulator, relative to a sample of cells expressing the FPRL2 polypeptide but not treated with the candidate modulator or relative to a sample of cells not expressing the FPRL2 polypeptide (mock-transfected cells) but treated with the candidate modulator.

When performed in the absence of HBP polypeptide, the assay can be used to identify an agonist of FPRL2 polypeptide activity. When the assay is performed in the presence of HBP polypeptide, it can be used to assay for an antagonist.

b. Adenylate Cyclase Assay:

Assays for adenylate cyclase activity are described by Kenimer & Nirenberg, 1981, Mol. Pharmacol.20: 585-591, incorporated herein by reference. That assay is a modification of the assay taught by Solomon et al., 1974, Anal. Biochem. 58: 541-548, also incorporated herein by reference. Briefly, 100 µl reactions contain 50 mM Tris-Hcl (pH 7.5), 5 mM $MgCl_2$, 20 mM creatine phosphate (disodium salt), 10 units (71 µg of protein) of creatine phosphokinase, 1 mM $\alpha$-$^{32}$P-ATP (tetrasodium salt, 2 µCi), 0.5 mM cyclic AMP, G-$^3$H-labeled cyclic AMP (approximately 10,000 cpm), 0.5 mM Ro20-1724, 0.25% ethanol, and 50-200 µg of protein homogenate to be tested (i.e., homogenate from cells expressing or not expressing a FPRL2 polypeptide, treated or not treated with HBP polypeptide with or without a candidate modulator). Reaction mixtures are generally incubated at 37° C. for 60 minutes. Following incubation, reaction mixtures are deproteinized by the addition of 0.9 ml of cold 6% trichloroacetic acid. Tubes are centrifuged at 1800×g for 20 minutes and each supernatant solution is added to a Dowex AG50W-X4 column. The cAMP fraction from the column is eluted with 4 ml of 0.1 mM imidazole-HCl (pH 7.5) into a counting vial. Assays should be performed in triplicate. Control reactions should also be performed using protein homogenate from cells that do not express a FPRL2 polypeptide.

According to the invention, adenylate cyclase activity is "changed" if it increases or decreases by 10% or more in a sample taken from cells treated with a candidate modulator of FPRL2 polypeptide activity, relative to a similar sample of cells not treated with the candidate modulator or relative to a sample of cells not expressing the FPRL2 polypeptide (mock-transfected cells) but treated with the candidate modulator.

c. cAMP Assay:

Intracellular or extracellular cAMP is measured using a cAMP radioimmunoassay (RIA) or cAMP binding protein according to methods widely known in the art. For example, Horton & Baxendale, 1995, Methods Mol. Biol. 41: 91-105, which is incorporated herein by reference, describes an RIA for cAMP.

A number of kits for the measurement of cAMP are commercially available, such as the High Efficiency Fluorescence Polarization-based homogeneous assay marketed by LJL Biosystems and NEN Life Science Products. Control reactions should be performed using extracts of mock-transfected cells to exclude possible non-specific effects of some candidate modulators.

The level of cAMP is "changed" if the level of cAMP detected in cells, expressing a FPRL2 polypeptide and treated with a candidate modulator of FPRL2 polypeptide activity (or in extracts of such cells), using the RIA-based assay of Horton & Baxendale, 1995, supra, increases or decreases by at least 10% relative to the cAMP level in similar cells not treated with the candidate modulator.

d. Phospholipid Breakdown, DAG Production and Inositol Trisphosphate Levels:

Receptors that activate the breakdown of phospholipids can be monitored for changes due to the activity of known or suspected modulators of FPRL2 polypeptide by monitoring phospholipid breakdown, and the resulting production of second messengers DAG and/or inositol trisphosphate (IP3). Methods of detecting each of these are described in *Phospholipid Signalling Protocols* edited by Ian M. Bird. Totowa, N.J., Humana Press, 1998, which is incorporated herein by reference. See also Rudolph et al., 1999, J. Biol. Chem. 274: 11824-11831, incorporated herein by reference, which also describes an assay for phosphatidylinositol breakdown. Assays should be performed using cells or extracts of cells expressing FPRL2 polypeptide, treated or not treated with HBP polypeptide with or without a candidate modulator. Control reactions should be performed using mock-transfected cells, or extracts from them in order to exclude possible non-specific effects of some candidate modulators.

According to the invention, phosphatidylinositol breakdown, and diacylglycerol and/or inositol trisphosphate levels are "changed" if they increase or decrease by at least 10% in a sample from cells expressing a FPRL2 polypeptide and treated with a candidate modulator, relative to the level observed in a sample from cells expressing a FPRL2 polypeptide that is not treated with the candidate modulator.

e. PKC Activation Assays:

Growth factor receptor tyrosine kinases can signal via a pathway involving activation of Protein Kinase C (PKC), which is a family of phospholipid- and calcium-activated protein kinases. PKC activation ultimately results in the transcription of an array of proto-oncogene transcription factor-encoding genes, including c-fos, c-myc and c-jun, proteases, protease inhibitors, including collagenase type I and plasminogen activator inhibitor, and adhesion molecules, including intracellular adhesion molecule I (ICAM I). Assays designed to detect increases in gene products induced by PKC can be used to monitor PKC activation and thereby receptor activity. In addition, the activity of receptors that signal via PKC can be monitored through the use of reporter gene constructs driven by the control sequences of genes activated by PKC activation. This type of reporter gene-based assay is discussed in more detail below.

For a more direct measure of PKC activity, the method of Kikkawa et al., 1982, J. Biol. Chem. 257: 13341, incorporated herein by reference, can be used. This assay measures phosphorylation of a PKC substrate peptide, which is subsequently separated by binding to phosphocellulose paper. This PKC assay system can be used to measure activity of purified kinase, or the activity in crude cellular extracts. Protein kinase C sample can be diluted in 20 mM HEPES/2 mM DTT immediately prior to assay.

The substrate for the assay is the peptide Ac-FKKSFKL-NH2 (SEQ ID NO: 11), derived from the myristoylated alanine-rich protein kinase C substrate protein (MARCKS). The $K_m$ of the enzyme for this peptide is approximately 50 µM. Other basic, protein kinase C-selective peptides known in the art can also be used, at a concentration of at least 2 -3 times their $K_m$. Cofactors required for the assay include calcium, magnesium, ATP, phosphatidylserine and diacylglycerol. Depending upon the intent of the user, the assay can be performed to determine the amount of PKC present (activating conditions) or the amount of active PKC present (non-activating conditions). For most purposes according to the invention, non-activating conditions will be used, such that the PKC, that is active in the sample when it is isolated, is measured, rather than measuring the PKC that can be activated. For non-activating conditions, calcium is omitted from the assay in favor of EGTA.

The assay is performed in a mixture containing 20 mM HEPES, pH 7.4, 1-2 mM DTT, 5 mM MgCl$_2$, 100 µM ATP, ~1 µCi γ-$^{32}$P-ATP, 100 µg/ml peptide substrate (~100 µM), 140 µM/3.8 µM phosphatidylserine/diacylglycerol membranes, and 100 µM calcium (or 500 µM EGTA). 48 µl of sample, diluted in 20 mM HEPES, pH 7.4, 2 mM DTT is used in a final reaction volume of 80 µl. Reactions are performed at 30° C. for 5-10 minutes, followed by addition of 25 µl of 100 mM ATP, 100 mM EDTA, pH 8.0, which stops the reactions.

After the reaction is stopped, a portion (85 µl) of each reaction is spotted onto a Whatman P81 cellulose phosphate filter, followed by washes: four times 500 ml in 0.4% phosphoric acid, (5-10 min per wash); and a final wash in 500 ml 95% EtOH, for 2-5 min. Bound radioactivity is measured by scintillation counting. Specific activity (cpm/nmol) of the labelled ATP is determined by spotting a sample of the reaction onto P81 paper and counting without washing. Units of PKC activity, defined as nmol phosphate transferred per min, are calculated as follows:

The activity, in UNITS (nmol/min) is: =

$$\frac{(\text{cpm on paper}) \times (105 \text{ µl total} / 85 \text{ µl spotted})}{(\text{assay time, min})(\text{specific activity of ATP cpm/nmol})}.$$

An alternative assay can be performed using a Protein Kinase C Assay Kit sold by PanVera (Cat. #P2747).

Assays are performed on extracts from cells expressing a FPRL2 polypeptide, treated or not treated with HBP polypeptide with or without a candidate modulator. Control reactions should be performed using mock-transfected cells, or extracts from them in order to exclude possible non-specific effects of some candidate modulators.

According to the invention, PKC activity is "changed" by a candidate modulator when the units of PKC measured by either assay described above increase or decrease by at least 10%, in extracts from cells expressing FPRL2 polypeptide and treated with a candidate modulator, relative to a reaction performed on a similar sample from cells not treated with a candidate modulator.

f. Kinase Assays:

MAP kinase activity can be assayed using any of several kits available commercially, for example, the p38 MAP Kinase assay kit sold by New England Biolabs (Cat #9820) or the Flash Plate™ MAP Kinase assays sold by Perkin-Elmer Life Sciences.

MAP Kinase activity is "changed" if the level of activity is increased or decreased by 10% or more in a sample from cells, expressing a FPRL2 polypeptide, treated with a candidate modulator relative to MAP kinase activity in a sample from similar cells not treated with the candidate modulator.

Direct assays for tyrosine kinase activity using known synthetic or natural tyrosine kinase substrates and labelled phosphate are well known, as are similar assays for other types of kinases (e.g., Ser/Thr kinases). Kinase assays can be performed with both purified kinases and crude extracts prepared from cells expressing a FPRL2 polypeptide, treated with or without HBP polypeptide, with or without a candidate modulator. Control reactions should be performed using mock-transfected cells, or extracts from them in order to exclude possible non-specific effects of some candidate modulators. Substrates can be either full-length protein or synthetic peptides representing the substrate. Pinna & Ruzzene (1996, Biochem. Biophys. Acta 1314: 191-225, incorporated herein by reference) list a number of phosphorylation substrate sites useful for detecting kinase activities. A number of kinase substrate peptides are commercially available. One that is particularly useful is the "Src-related peptide," RRLIEDAEYAARG (SEQ ID NO: 12; available from Sigma #A7433), which is a substrate for many receptor and nonreceptor tyrosine kinases. Because the assay described below requires binding of peptide substrates to filters, the peptide substrates should have a net positive charge to facilitate binding. Generally, peptide substrates should have at least 2 basic residues and a free amino terminus. Reactions generally use a peptide concentration of 0.7-1.5 mM.

Assays are generally carried out in a 25 µl volume comprising 5 µl of 5× kinase buffer (5 mg/mL BSA, 150 mM Tris-Cl (pH 7.5), 100 mM $MgCl_2$; depending upon the exact kinase assayed for, $MnCl_2$ can be used in place of or in addition to the $MgCl_2$), 5 µl of 1.0 mM ATP (0.2 mM final concentration), γ-32P-ATP (100-500 cpm/pmol), 3 µl of 10 mM peptide substrate (1.2 mM final concentration), cell extract containing kinase to be tested (cell extracts used for kinase assays should contain a phosphatase inhibitor (e.g. 0.1-1 mM sodium orthovanadate)), and $H_2O$ to 25 µl. Reactions are performed at 30° C., and are initiated by the addition of the cell extract.

Kinase reactions are performed for 30 seconds to about 30 minutes, followed by the addition of 45 µl of ice-cold 10% trichloroacetic acid (TCA). Samples are spun for 2 minutes in a microcentrifuge, and 35 µl of the supernatant is spotted onto Whatman P81 cellulose phosphate filter circles. The filters are washed three times with 500 ml cold 0.5% phosphoric acid, followed by one wash with 200 ml of acetone at room temperature for 5 minutes. Filters are dried and incorporated $^{32}P$ is measured by scintillation counting. The specific activity of ATP in the kinase reaction (e.g., in cpm/pmol) is determined by spotting a small sample (2-5 µl) of the reaction onto a P81 filter circle and counting directly, without washing. Counts per minute obtained in the kinase reaction (minus blank) are then divided by the specific activity to determine the moles of phosphate transferred in the reaction.

Tyrosine kinase activity is "changed" if the level of kinase activity is increased or decreased by 10% or more in a sample from cells, expressing a FPRL2 polypeptide, treated with a candidate modulator relative to kinase activity in a sample from similar cells not treated with the candidate modulator.

g. Transcriptional Reporters for Downstream Pathway Activation:

The intracellular signal initiated by binding of an agonist to a receptor, e.g., FPRL2 polypeptide, sets in motion a cascade of intracellular events, the ultimate consequence of which is a rapid and detectable change in the transcription or translation of one or more genes. The activity of the receptor can therefore be monitored by detecting the expression of a reporter gene driven by control sequences responsive to FPRL2 activation.

As used herein "promoter" refers to the transcriptional control elements necessary for receptor-mediated regulation of gene expression, including not only the basal promoter, but also any enhancers or transcription-factor binding sites necessary for receptor-regulated expression. By selecting promoters that are responsive to the intracellular signals resulting from agonist binding, and operatively linking the selected promoters to reporter genes whose transcription, translation or ultimate activity is readily detectable and measurable, the transcription based reporter assay provides a rapid indication of whether a given receptor is activated.

Reporter genes such as luciferase, CAT, GFP, β-lactamase or β-galactosidase are well known in the art, as are assays for the detection of their products.

Genes particularly well suited for monitoring receptor activity are the "immediate early" genes, which are rapidly induced, generally within minutes of contact between the receptor and the effector protein or ligand. The induction of immediate early gene transcription does not require the synthesis of new regulatory proteins. In addition to rapid responsiveness to ligand binding, characteristics of preferred genes useful for making reporter constructs include: low or undetectable expression in quiescent cells; induction that is transient and independent of new protein synthesis; subsequent shut-off of transcription requires new protein synthesis; and mRNAs transcribed from these genes have a short half-life. It is preferred, but not necessary that a transcriptional control element have all of these properties for it to be useful.

An example of a gene that is responsive to a number of different stimuli is the c-fos proto-oncogene. The c-fos gene is activated in a protein-synthesis-independent manner by growth factors, hormones, differentiation-specific agents, stress, and other known inducers of cell surface proteins. The induction of c-fos expression is extremely rapid, often occurring within minutes of receptor stimulation. This characteristic makes the c-fos regulatory regions particularly attractive for use as a reporter of receptor activation.

The c-fos regulatory elements include (see, Verma et al., 1987, Cell 51: 513-514): a TATA box that is required for transcription initiation; two upstream elements for basal transcription, and an enhancer, which includes an element with dyad symmetry and which is required for induction by TPA, serum, EGF, and PMA.

The 20 bp c-fos transcriptional enhancer element located between −317 and −298 bp upstream from the c-fos MRNA cap site, is essential for serum induction in serum starved NIH 3T3 cells. One of the two upstream elements is located at −63 to −57 and it resembles the consensus sequence for cAMP regulation.

The transcription factor CREB (cyclic AMP responsive element binding protein) is, as the name implies, responsive to levels of intracellular cAMP. Therefore, the activation of a receptor that signals via modulation of cAMP levels can be monitored by detecting either the binding of the transcription factor, or the expression of a reporter gene linked to a CREB-binding element (termed the CRE, or cAMP response element). The DNA sequence of the CRE is TGACGTCA. Reporter constructs responsive to CREB binding activity are described in U.S. Pat. No. 5,919,649.

Other promoters and transcriptional control elements, in addition to the c-fos elements and CREB-responsive constructs, include the vasoactive intestinal peptide (VIP) gene promoter (cAMP responsive; Fink et al., 1988, Proc. Natl. Acad. Sci. 85:6662-6666); the somatostatin gene promoter (cAMP responsive; Montminy et al., 1986, Proc. Natl. Acad. Sci. 8.3:6682-6686); the proenkephalin promoter (responsive to cAMP, nicotinic agonists, and phorbol esters; Comb et al., 1986, Nature 323:353-356); the phosphoenolpyruvate carboxy-kinase (PEPCK) gene promoter (cAMP responsive; Short et al., 1986, J. Biol. Chem. 261:9721-9726).

Additional examples of transcriptional control elements that are responsive to changes in GPCR activity include, but are not limited to those responsive to the AP-1 transcription factor and those responsive to NF-κB activity. The consensus AP-1 binding site is the palindrome TGA(C/G)TCA (Lee et al., 1987, Nature 325: 368-372; Lee et al., 1987, Cell 49: 741-752). The AP-1 site is also responsible for mediating induction by tumor promoters such as the phorbol ester 12-O-tetradecanoylphorbol-beta-acetate (TPA), and are therefore sometimes also referred to as a TRE, for TPA-response element. AP-1 activates numerous genes that are involved in the early response of cells to growth stimuli. Examples of AP-1-responsive genes include, but are not limited to the genes for Fos and Jun (which proteins themselves make up AP-1 activity), Fos-related antigens (Fra) 1 and 2, IκBα, ornithine decarboxylase, and annexins I and II.

The NF-κB binding element has the consensus sequence GGGGACTTTCC (SEQ ID NO: 13). A large number of genes have been identified as NF-κB responsive, and their control elements can be linked to a reporter gene to monitor GPCR activity. A small sample of the genes responsive to NF-κB includes those encoding IL-1β (Hiscott et al., 1993, Mol. Cell. Biol. 13: 6231-6240), TNF-α (Shakhov et al., 1990, J. Exp. Med. 171: 35-47), CCR5 (Liu et al., 1998, AIDS Res. Hum. Retroviruses 14: 1509-1519), P-selection (Pan & McEver, 1995, J. Biol. Chem. 270: 23077-23083), Fas ligand (Matsui et al., 1998, J. Immunol. 161: 3469-3473), GM-CSF (Schreck & Baeuerle, 1990, Mol. Cell. Biol. 10: 1281-1286) and IκBα (Haskill et al., 1991, Cell 65:1281-1289). Each of these references is incorporated herein by reference. Vectors encoding NF-κB-responsive reporters are also known in the art or can be readily made by one of skill in the art using, for example, synthetic NF-κB elements and a minimal promoter, or using the NF-κB-responsive sequences of a gene known to be subject to NF-κB regulation. Further, NF-κB responsive reporter constructs are commercially available from, for example, CLONTECH.

A given promoter construct should be tested by exposing FPRL2 polypeptide-expressing cells, transfected with the construct, to HBP polypeptide. An increase of at least two-fold in the expression of reporter in response to HBP polypeptide indicates that the reporter is an indicator of FPRL2 polypeptide activity.

In order to assay FPRL2 polypeptide activity with a transcriptional reporter construct, cells that stably express a FPRL2 polypeptide are stably transfected with the reporter construct. To screen for agonists, the cells are left untreated, exposed to candidate modulators, or exposed to HBP polypeptide, and expression of the reporter is measured. The HBP polypeptide-treated cultures serve as a standard for the level of transcription induced by a known agonist. An increase of at least 50% in reporter expression in the presence of a candidate modulator indicates that the candidate is a modulator of FPRL2 polypeptide activity. An agonist will induce at least as much, and preferably the same amount or greater reporter expression than HBP polypeptide alone. This approach can also be used to screen for inverse agonists where cells express a FPRL2 polypeptide at levels such that there is an elevated basal activity of the reporter in the absence of HBP polypeptide or another agonist. A decrease in reporter activity of 10% or more in the presence of a candidate modulator, relative to its absence, indicates that the compound is an inverse agonist.

To screen for antagonists, the cells expressing FPRL2 polypeptide and carrying the reporter construct are exposed to HBP polypeptide (or another agonist) in the presence and absence of candidate modulator. A decrease of 10% or more in reporter expression in the presence of candidate modulator, relative to the absence of the candidate modulator, indicates that the candidate is a modulator of FPRL2 polypeptide activity.

Controls for transcription assays include cells not expressing FPRL2 polypeptide but carrying the reporter construct, as well as cells with a promoterless reporter construct. Compounds that are identified as modulators of FPRL2 polypeptide-regulated transcription should also be analyzed to determine whether they affect transcription driven by other regulatory sequences and by other receptors, in order to determine the specificity and spectrum of their activity.

The transcriptional reporter assay, and most cell-based assays, are well suited for screening expression libraries for proteins for those that modulate FPRL2 polypeptide activity. The libraries can be, for example, cDNA libraries from natural sources, e.g., plants, animals, bacteria, etc., or they can be libraries expressing randomly or systematically mutated variants of one or more polypeptides. Genomic libraries in viral vectors can also be used to express the mRNA content of one cell or tissue in the different libraries used for screening of FPRL2 polypeptide.

h) Inositol Phosphates (IP) Measurement

Cells of the invention, for example, CHO-K1 cells, are labelled for 24 hours with 10 μCi/ml [$^3$H] inositol in inositol free DMEM containing 5% FCS, antibiotics, amphotericin, sodium pyruvate and 400 μg/ml G418. Cells are incubated for 2 h in Krebs-Ringer Hepes (KRH) buffer of the following composition (124 mM NaCl, 5 mM KCl, 1.25 mM $MgSO_4$, 1.45 mM $CaCl_2$, 1.25 mM $KH_2PO_4$, 25 mM Hepes (pH:7.4) and 8 mM glucose). The cells are then challenged with HBP polypeptide for 30 min. The incubation is stopped by the addition of an ice cold 3% perchloric acid solution. IP are extracted and separated on Dowex columns as previously described (25).

FPRL2 Polypeptide Assay

The invention provides for an assay for detecting the activity of a receptor of the invention in a sample. For example, FPRL2 polypeptide activity can be measured in a sample comprising a cell or a cell membrane that expresses FPRL2 polypeptide. As above, HBP polypeptide (SEQ IN NO:18) is used as an example in this section. It should be understood that any HBP polypeptide as defined herein can be used in these assays. The assay is performed by incubating the sample in the presence or absence of HBP polypeptide and carrying out a second messenger assay, as described above. The results of the second messenger assay performed in the presence or absence of HBP polypeptide are compared to determine if the FPRL2 polypeptide receptor is active. An increase of 10% or more in the detected level of a given second messenger, as defined herein, in the presence of HBP polypeptide relative to the amount detected in an assay performed in the absence of HBP polypeptide is indicative of FPRL2 polypeptide activity.

Any of the assays of receptor activity, including but not limited to the GTP-binding, GTPase, adenylate cyclase, cAMP, phospholipid-breakdown, diacylglycerol, inositol trisphosphate, arachidonic acid release (see below), PKC, kinase and transcriptional reporter assays, can be used to determine the presence of an agent in a sample, e.g., a tissue sample, that affects the activity of the FPRL2 polypeptide receptor molecule. To do so, FPRL2 polypeptide is assayed for activity in the presence and absence of the sample or an extract of the sample. An increase in FPRL2 polypeptide activity in the presence of the sample or extract relative to the absence of the sample indicates that the sample contains an agonist of the receptor activity. A decrease in receptor activity in the presence of HBP polypeptide or another agonist and the sample, relative to receptor activity in the presence of HBP polypeptide alone, indicates that the sample contains an antagonist of FPRL2 polypeptide activity. If desired, samples can then be fractionated and further tested to isolate or purify the agonist or antagonist. The amount of increase or decrease in measured activity necessary for a sample to be said to contain a modulator depends upon the type of assay used. Generally, a 10% or greater change (increase or decrease) relative to an assay performed in the absence of a sample indicates the presence of a modulator in the sample. One exception is the transcriptional reporter assay, in which at least a two-fold increase or 10% decrease in signal is necessary for a sample to be said to contain a modulator. It is preferred that an agonist stimulates at least 50%, and preferably 75% or 100% or more, e.g., 2-fold, 5-fold, 10-fold or greater receptor activation than with HBP polypeptide alone.

Other functional assays include, for example, microphysiometer or biosensor assays (see Hafner, 2000, Biosens. Bioelectron. 15: 149-158, incorporated herein by reference). The intracellular level of arachidonic acid can also be determined as described in Gijon et al., 2000, J. Biol. Chem., 275:20146-20156.

II. Diagnostic Assays Based Upon the Interaction of FPRL2 Polypeptide and HBP Polypeptide:

Signalling through GPCRs is instrumental in the pathology of a large number of diseases and disorders. FPRL2 polypeptide, which is expressed in cells of the lymphocyte lineages, spleen, small intestine, lung, heart, can have a role in immune processes, cancer and associated disorders or diseases.

The expression pattern of FPRL2 polypeptide and the knowledge with respect to disorders generally mediated by GPCRs suggests that FPRL2 polypeptide can be involved in disturbances of cell migration, cancer, development of tumours and tumour metastasis, inflammatory and neoplastic processes, wound and bone healing and dysfunction of regulatory growth functions, obesity, anorexia, bulimia, acute heart failure, hypotension, hypertension, urinary retention, osteoporosis, angina pectoris, restenosis, atherosclerosis, thrombosis and other cardiovascular diseases, autoimmune and, diseases characterized by excessive smooth muscle cell proliferation, aneurysms, diseases characterized by loss of smooth muscle cells or reduced smooth muscle cell proliferation, stroke, ischemia, ulcers, allergies, prostatic hypertrophy, migraine, vorniting, psychotic and neurological disorders, including anxiety, schizophrenia, manic depression, depression, delirium, dementia and severe mental retardation, degenerative diseases, neurodegenerative diseases such as Alzheimer's disease or Parkinson's disease, and dyskinasias, such as Huntington's disease or Gilles de la Tourett's syndrome and other related diseases including thrombosis and other cardiovascular diseases, autoimmune and inflammatory diseases such as psoriasis, Eczeme, inflammatory and trophic diseases of skin, rheumatoid arthritis, scleroderma, lupus, polymyositis, dermatomyositis, Crohn's disease, inflammatory bowel disease (IBD), Irritable Bowel Syndrome, Ulcerative Colitis, Asthma, Chronic Obstructive Pulmonary Disease, Allergic Rhinitis, Fibromyalgia, Organ Transplant Rejection, Graft versus host disease, Multiple Sclerosis, Acute, Ischemic Stroke, Infectious diseases, Hepatitis A, Hepatitis B, Hepatitis C, Sepsis, Septic shock, Chronic bronchitis, infections such as bacterial, fungal, protozoan and viral infections, such as infections caused by HIV1 and HIV2, and pain, cancer, anorexia, bulimia, asthma, acute heart failure, hypertension, urinary retention, osteoporosis, angina pectoris, myocardial infarction, ulcers, allergies, benign prostatic hypertrophy, and Type 1 Diabetes, Type 2 Diabetes, Osteoarthritis, Diabetic Retinopathy, Diabetic Nephropathy and fertility dysfunctions, foetal developmental disorders The interaction of FPRL2 polypeptide with HBP polypeptide can be used as the basis of assays for the diagnosis or monitoring of diseases, disorders or processes involving FPRL2 polypeptide signalling. Diagnostic assays for FPRL2 polypeptide-related diseases or disorders can have several different forms. First, diagnostic assays can measure the amount of FPRL2 polypeptides, mRNA or ligand in a sample of tissue. Assays that measure the amount of mRNA encoding FPRL2 polypeptide also fit into this category. Second, assays can evaluate the qualities of the receptor or the ligand. For example, assays that determine whether an individual expresses a mutant or variant form of FPRL2 polypeptide can be used diagnostically. Third, assays that measure one or more activities of FPRL2 polypeptide can be used diagnostically.

A. Assays That Measure the Amount of FPRL2 Polypeptide

FPRL2 polypeptide levels can be measured and compared to standards in order to determine whether an abnormal level of the receptor or its ligand is present in a sample, either of which indicate probable dysregulation of FPRL2 polypeptide signalling. Polypeptide levels are measured, for example, by immunohistochemistry using antibodies specific for the polypeptide. A sample isolated from an individual suspected of suffering from a disease or disorder characterized by FPRL2 polypeptide activity is contacted with an antibody for a FPRL2 polypeptide, and binding of the antibody is measured as known in the art (e.g., by measurement of the activity of an enzyme conjugated to a secondary antibody).

Another approach to the measurement of FPRL2 polypeptide levels uses flow cytometry analysis of cells from an affected tissue. Methods of flow cytometry, including the fluorescent labeling of antibodies specific for FPRL2 polypeptide, are well known in the art. Other approaches include radioimmunoassay or ELISA. Methods for each of these are also well known in the art.

The amount of binding detected is compared to the binding in a sample of similar tissue from a healthy individual, or from a site on the affected individual that is not so affected. An increase of 10% or more relative to the standard is diagnostic for a disease or disorder characterized by FPRL2 polypeptide dysregulation.

FPRL2 polypeptide expression can also be measured by determining the amount of mRNA encoding the polypeptides in a sample of tissue. Levels of mRNA can be measured by quantitative or semi-quantitative PCR. Methods of "quantitative" amplification are well known to those of skill in the art, and primer sequences for the amplification of FPRL2 nucleic acid are disclosed herein. A common method of quantitative PCR involves simultaneously co-amplifying a known quantity of a control sequence using the same primers. This provides an internal standard that can be used to calibrate the PCR reaction. Detailed protocols for quantitative PCR are provided in *PCR Protocols, A Guide to Methods and Applications*, Innis et al., Academic Press, Inc. N.Y., (1990), which is incorporated herein by reference. An increase of 10% or more in the amount of mRNA encoding FPRL2 polypeptide in a sample, relative to the amount expressed in a sample of like tissue from a healthy individual or in a sample of tissue from an unaffected location in an affected individual is diagnostic for a disease or disorder characterized by dysregulation of FPRL2 polypeptide signalling.

B. Qualitative Assays

Assays that evaluate whether or not a FPRL2 polypeptide or the mRNA encoding it are wild-type or not can be used diagnostically. In order to diagnose a disease or disorder characterized by FPRL2 polypeptide dysregulation in this manner, RNA isolated from a sample is used as a template for PCR amplification of FPRL2 polypeptide. The amplified sequences are then either directly sequenced using standard methods, or are first cloned into a vector, followed by sequencing. A difference in the sequence that changes one or more encoded amino acids relative to the sequence of wild-type FPRL2 polypeptide can be diagnostic of a disease or disorder characterized by dysregulation of FPRL2 polypeptide signalling. It can be useful, when a change in coding sequence is identified in a sample, to express the variant receptor or ligand and compare its activity to that of wild type FPRL2 polypeptide. Among other benefits, this approach can provide novel mutants, including constitutively active and null mutants.

In addition to standard sequencing methods, amplified sequences can be assayed for the presence of specific mutations using, for example, hybridization of molecular beacons that discriminate between wild type and variant sequences. Hybridization assays that discriminate on the basis of changes as small as one nucleotide are well known in the art. Alternatively, any of a number of "minisequencing" assays can be performed, including, those described, for example, in U.S. Pat. Nos. 5,888,819, 6,004,744 and 6,013,431 (incorporated herein by reference). These assays and others known in the art can determine the presence, in a given sample, of a nucleic acid with a known polymorphism.

If desired, array or microarray-based methods can be used to analyze the expression or the presence of mutation, in FPRL2 polypeptide sequences. Array-based methods for minisequencing and for quantitation of nucleic acid expression are well known in the art.

C. Functional Assays.

Diagnosis of a disease or disorder characterized by the dysregulation of FPRL2 polypeptide signalling can also be performed using functional assays. To do so, cell membranes or cell extracts prepared from a tissue sample are used in an assay of FPRL2 polypeptide activity as described herein (e.g., ligand binding assays, the GTP-binding assay, GTPase assay, adenylate cyclase assay, cAMP assay, arachidonic acid level, phospholipid breakdown, diacyl glycerol or inositol trisphosphate assays, PKC activation assay, or kinase assay). The activity detected is compared to that in a standard sample taken from a healthy individual or from an unaffected site on the affected individual. As an alternative, a sample or extract of a sample can be applied to cells expressing FPRL2 polypeptide, followed by measurement of FPRL2 polypeptide signalling activity relative to a standard sample. A difference of 10% or more in the activity measured in any of these assays, relative to the activity of the standard, is diagnostic for a disease or disorder characterized by dysregulation of FPRL2 polypeptide signalling.

Modulation of FPRL2 Polypeptide Activity in a Cell According to the Invention

The discovery of HBP polypeptide as a ligand of FPRL2 polypeptide provides methods of modulating the activity of a FPRL2 polypeptide polypeptide in a cell. FPRL2 polypeptide activity is modulated in a cell by delivering to that cell an agent that modulates the function of a FPRL2 polypeptide polypeptide. This modulation can be performed in cultured cells as part of an assay for the identification of additional modulating agents, or, for example, in an animal, including a human. Agents include HBP polypeptide and other ligands as defined herein, as well as additional modulators identified using the screening methods described herein including but not limited to any of the HBP polypeptide analogues.

An agent can be delivered to a cell by adding it to culture medium. The amount to deliver will vary with the identity of the agent and with the purpose for which it is delivered. For example, in a culture assay to identify antagonists of FPRL2 polypeptide activity, one will preferably add an amount of agent, e.g., HBP polypeptide that half-maximally activates the receptors (e.g., approximately $EC_{50}$), preferably without exceeding the dose required for receptor saturation. This dose can be determined by titrating the amount of HBP polypeptide to determine the point at which further addition of HBP polypeptide has no additional effect on FPRL2 polypeptide activity.

When a modulator of FPRL2 polypeptide activity is administered to an animal for the treatment of a disease or disorder, the amount administered can be adjusted by one of skill in the art on the basis of the desired outcome. Successful treatment is achieved when one or more measurable aspects of the pathology (e.g., tumor cell growth, accumulation of inflammatory cells) is changed by at least 10% relative to the value for that aspect prior to treatment.

Candidate Modulators Useful According to the Invention

The invention provides for a compound that is a modulator of a receptor of the invention.

Preferably a candidate modulator is a HBP polypeptide (SEQ ID NO:18), a HBP polypeptide as defined herein above, a ligand as defined herein above or an agent identified according to the invention.

The candidate compound can be a synthetic compound, or a mixture of compounds, or may be a natural product (e.g. a plant extract or culture supernatant). A candidate compound according to the invention includes but is not limited to a small molecule that can be synthesized, a natural extract, peptides, polypeptides, carbohydrates, lipids, an antibody or antigen-binding fragment thereof, nucleic acids, and a small organic molecules.

Candidate modulator compounds from large libraries of synthetic or natural compounds can be screened. Numerous means are currently used for random and directed synthesis of saccharide, peptide, and nucleic acid based compounds. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Combinatorial libraries are available and can be prepared. Alternatively, libraries of natural compounds in the form of bacterial, fungal, plant and animal extracts are available from e.g., Pan Laboratories (Bothell, Wash.) or MycoSearch (NC), or are readily producible by methods well known in the art. Additionally, natural and synthetically produced libraries and compounds are readily modified through conventional chemical, physical, and biochemical means.

Useful compounds may be found within numerous chemical classes. Useful compounds may be organic compounds, or small organic compounds. Small organic compounds have a molecular weight of more than 50 yet less than about 2,500 daltons, preferably less than about 750, more preferably less than about 350 daltons. Exemplary classes include heterocycles, peptides, saccharides, steroids, and the like. The compounds may be modified to enhance efficacy, stability, pharmaceutical compatibility, and the like. Structural identification of an agent may be used to identify, generate, or screen additional agents. For example, where peptide agents are identified, they may be modified in a variety of ways to enhance their stability, such as using an unnatural amino acid, such as a D-amino acid, particularly D-alanine, by functionalizing the amino or carboxylic terminus, e.g. for the amino group, acylation or alkylation, and for the carboxyl group, esterification or amidification, or the like.

For primary screening, a useful concentration of a candidate compound according to the invention is from about 10 nM to about 100 µM or more (i.e. 1 mM, 10 mM, 100 mM, or even 1M), but can also be 1 nM and higher, 1 pM and higher, or 1 fM and higher. The primary screening concentration will be used as an upper limit, along with nine additional concentrations, wherein the additional concentrations are determined by reducing the primary screening concentration at half-log intervals (e.g. for 9 more concentrations) for secondary screens or for generating concentration curves.

Antibodies Useful According to the Invention

The invention provides for antibodies to FPRL2 polypeptide. Antibodies can be made using standard protocols known in the art (See, for example, Antibodies: A Laboratory Manual ed. by Harlow and Lane (Cold Spring Harbor Press: 1988)). A mammal, such as a mouse, hamster, or rabbit can be immunized with an immunogenic form of the peptide (e.g., FPRL2 polypeptide or an antigenic fragment which is capable of eliciting an antibody response, or a fusion protein as described herein above). Immunogens for raising antibodies are prepared by mixing the polypeptides (e.g., isolated recombinant polypeptides or synthetic peptides) with adjuvants. Alternatively, FPRL2 polypeptides or peptides are made as fusion proteins to larger immunogenic proteins. Polypeptides can also be covalently linked to other larger immunogenic proteins, such as keyhole limpet hemocyanin. Alternatively, plasmid or viral vectors encoding FPRL2 polypeptide, or a fragment of these proteins, can be used to express the polypeptides and generate an immune response in an animal as described in Costagliola et al., 2000, J. Clin. Invest. 105:803-811, which is incorporated herein by reference. In order to raise antibodies, immunogens are typically administered intradermally, subcutaneously, or intramuscularly to experimental animals such as rabbits, sheep, and mice. In addition to the antibodies discussed above, genetically engineered antibody derivatives can be made, such as single chain antibodies.

The progress of immunization can be monitored by detection of antibody titers in plasma or serum. Standard ELISA, flow cytometry or other immunoassays can also be used with the immunogen as antigen to assess the levels of antibodies. Antibody preparations can be simply serum from an immunized animal, or if desired, polyclonal antibodies can be isolated from the serum by, for example, affinity chromatography using immobilized immunogen.

To produce monoclonal antibodies, antibody-producing splenocytes can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with FPRL2 polypeptide, and monoclonal antibodies isolated from the media of a culture comprising such hybridoma cells.

In addition, a functional fragment of an antibody, including fragment of chimeric, humanized, primatized or single chain antibody, can also be produced. Functional fragments of the foregoing antibodies retain at least one binding function and/or modulation function of the full-length antibody from which they are derived. Preferred functional fragments retain an antigen-binding function of a corresponding full-length antibody (e.g., retain the ability to bind a human FPRL2). Particularly preferred functional fragments retain the ability to inhibit or activate one or more functions characteristic of a FPRL2, such as a binding activity, a signaling activity, and/or stimulation of a cellular response. For example, in one embodiment, a functional fragment can inhibit or activate the interaction of FPRL2 with one or more of its ligands, and/or can inhibit or activate one or more receptor-mediated functions.

For example, antibody fragments capable of binding to a human FPRL2 receptor or portion thereof, including, but not limited to, scFv, Fv, Fab, Fab' and F(ab')$^2$ fragments are encompassed by the invention. Such fragments can be producted by enzymatic cleavage or by recombinant techniques, for example. For instance, papain or pepsin cleavage can generate Fab or F(ab')$^2$ fragments, respectively. Antibodies can also be produced in a variety of truncated forms using antibody genes in which one or more stop codons has been introduced upstream of the natural stop site. For example, a chimeric gene encoding a F(ab')$^2$ heavy chain portion can be designed to include DNA sequences encoding the CH1 domain and hinge region of the heavy chain.

The sequence of an antibody obtainable according to a screening method (e.g. FPRL2 422F 2B9 1C11, FPRL2 422F 2G3 1A10) can be an homologous sequence (which may exist in other mammal species or specific groups of human populations), where homology indicates sequence identity, means a sequence which presents a high sequence identity (more than 80%, 85%, 90%, 95% or 98% sequence identity) with the complete nucleotide or amino acid sequence of an antibody or fragment thereof. A functional homolog is characterized by the ability to bind FPRL2 as defined herein or by the ability to inhibit or stimulate a signal in response in FPRL2, or both.

Homologous sequences of an antibody sequence according to the invention may include an amino acid or nucleotide sequence encoding a similar sequence which exists in other animal species (rat, human, cat, dog, etc.) or in specific human population groups, but which are involved in the same biochemical pathway.

Such homologous sequences may comprise additions, deletions or substitutions of one or more amino acids or nucleotides, which do not substantially alter the functional characteristics of the antibody or fragment thereof according to the invention. That is, homologs will have at least 90% of the activity of an amino acid sequence of an antibody or fragment thereof and will bind, stimulate or inhibit FPRL2 specifically.

Such homologous sequences can also be nucleotide sequences of more than 50, 100, 200, 300, 400, 600, 800 or 1000 nucleotides which are able to hybridize to the amino acid sequence of any antibody or fragment thereof under stringent hybridisation conditions (such as the ones described by SAMBROOK et al., Molecular Cloning, Laboratory Manuel, Cold Spring, Harbor Laboratory press, New York). An example of "stringent hybridization conditions" is as follows: hybridize in 50% formamide, 5×SSC, 50 mM sodium phosphate (pH 6.8), 0.1% sodium pyrophosphate, 5× Denhardt's solution, 50 µg/ml sonicated salmon sperm DNA, 0.1% SDS and 10% dextran sulfate at 42° C.; and wash at 42° C. (or higher, e.g., up to two degrees C. below the $T_m$ of the perfect complement of the probe sequence) in 0.2×SSC and 0.1% SDS.

High Throughput Screening Kit

A high throughput screening kit according to the invention comprises all the necessary means and media for performing the detection of a modulator compound including an agonist, antagonist, inverse agonist or inhibitor to the receptor of the invention in the presence or absence of HBP polypeptide, preferably at a concentration in the range of 1 nM to 1 µM. The kit comprises materials to perform the following successive steps. Recombinant cells of the invention, comprising and expressing the nucleotide sequence encoding the FPRL2 polypeptide receptor, are grown on a solid support, such as a microtiter plate, more preferably a 96 well microtiter plate, according to methods well known to the person skilled in the art, especially as described in WO 00/02045. Modulator compounds according to the invention, at concentrations from about 1 nM to 1 µM or more, are added to the culture media of defined wells in the presence or absence of an appropriate concentration of HBP polypeptide (preferably in the range of 1 nM to 1 µM).

Kits according to the invention can also comprise materials necessary for second messenger assays amenable to high throughput screening analysis, including but not limited to the measurement of intracellular levels of cAMP, intracellular inositol phosphate, intracellular diacylglycerol concentrations, arachinoid acid concentration or MAP kinase or tyrosine kinase activity (as decribed above). For example, the FPRL2 polypeptide activity, as measured in a cyclic AMP assay, is quantified by a radioimmunoassay as previously described (26). Results are compared to the baseline level of FPRL2 polypeptide activity obtained from recombinant cells according to the invention in the presence of HBP polypeptide but in the absence of added modulator compound. Wells showing at least 2 fold, preferably 5 fold, more preferably 10 fold and most preferably a 100 fold or more increase or decrease in FPRL2 polypeptide activity as compared to the level of activity in the absence of modulator, are selected for further analysis.

Other Kits Useful According to the Invention

The invention provides for kits useful for screening for modulators of FPRL2 polypeptide activity, as well as kits useful for diagnosis of diseases or disorders characterized by dysregulation of FPRL2 polypeptide signalling. Kits useful according to the invention can include an isolated FPRL2 polypeptide (including a membrane-or cell-associated FPRL2 polypeptide, e.g., on isolated membranes, cells expressing FPRL2 polypeptide, or on an SPR chip). A kit can also comprise an antibody specific for FPRL2 polypeptide. Alternatively, or in addition, a kit can contain cells transformed to express FPRL2 polypeptide. In a further embodiment, a kit according to the invention can contain a polynucleotide encoding a FPRL2 polypeptide. In a still further embodiment, a kit according to the invention may comprise the specific primers useful for amplification of FPRL2 polypeptide as described below. All kits according to the invention will comprise the stated items or combinations of items and packaging materials therefor. Kits will also include instructions for use.

Transgenic Animals

Transgenic mice provide a useful tool for genetic and developmental biology studies and for the determination of the function of a novel sequence. According to the method of conventional transgenesis, additional copies of normal or modified genes are injected into the male pronucleus of the zygote and become integrated into the genomic DNA of the recipient mouse. The transgene is transmitted in a Mendelian manner in established transgenic strains. Constructs useful for creating transgenic animals comprise genes under the control of either their normal promoters or an inducible promoter, reporter genes under the control of promoters to be analyzed with respect to their patterns of tissue expression and regulation, and constructs containing dominant mutations, mutant promoters, and artificial fusion genes to be studied with regard to their specific developmental outcome. Typically, DNA fragments on the order of 10 kilobases or less are used to construct a transgenic animal (Reeves, 1998, New. Anat., 253:19). Transgenic animals can be created with a construct comprising a candidate gene containing one or more polymorphisms according to the invention. Alternatively, a transgenic animal expressing a candidate gene containing a single polymorphism can be crossed to a second transgenic animal expressing a candidate gene containing a different polymorphism and the combined effects of the two polymorphisms can be studied in the offspring animals.

Other Transgenic Animals

The invention provides for transgenic animals that include but are not limited to transgenic mice, rabbits, rats, pigs, sheep, horses, cows, goats, etc. A protocol for the production of a transgenic pig can be found in White and Yannoutsos, Current Topics in Complement Research: $64^{th}$ Forum in Immunology, pp. 88-94; U.S. Pat. No. 5,523,226; U.S. Pat. No. 5,573,933: PCT Application WO93/25071; and PCT Application WO95/04744. A protocol for the production of a transgenic mouse can be found in U.S. Pat. No. 5,530,177. A protocol for the production of a transgenic rat can be found in Bader and Ganten, Clinical and Experimental Pharmacology and Physiology, Supp. 3:S81-S87, 1996. A protocol for the production of a transgenic cow can be found in Transgenic Animal Technology, A Handbook, 1994, ed., Carl A. Pinkert, Academic Press, Inc. A protocol for the production of a transgenic rabbit can be found in Hammer et al., Nature 315:680-683, 1985 and Taylor and Fan, Frontiers in Bioscience 2:d298-308, 1997.

Knock Out Animals i. Standard

Knock out animals are produced by the method of creating gene deletions with homologous recombination. This technique is based on the development of embryonic stem (ES) cells that are derived from embryos, are maintained in culture and have the capacity to participate in the development of every tissue in the mouse when introduced into a host blastocyst. A knock out animal is produced by directing homologous recombination to a specific target gene in the ES cells, thereby producing a null allele of the gene. The potential phenotypic consequences of this null allele (either in heterozygous or homozygous offspring) can be analyzed (Reeves, supra).

ii. In Vivo Tissue Specific Knock Out in Mice Using Cre-lox.

The method of targeted homologous recombination has been improved by the development of a system for site-specific recombination based on the bacteriophage P1 site specific recombinase Cre. The Cre-loxP site-specific DNA recombinase from bacteriophage P1 is used in transgenic mouse assays in order to create gene knockouts restricted to defined tissues or developmental stages. Regionally restricted genetic deletion, as opposed to global gene knockout, has the advantage that a phenotype can be attributed to a particular cell/tissue (Marth, 1996, *Clin. Invest.* 97: 1999). In the Cre-loxP system one transgenic mouse strain is engineered such that loxP sites flank one or more exons of the gene of interest. Homozygotes for this so called 'floxed gene' are crossed with a second transgenic mouse that expresses the Cre gene under control of a cell/tissue type transcriptional promoter. Cre protein then excises DNA between loxP recognition sequences and effectively removes target gene function (Sauer, 1998, *Methods,* 14:381). There are now many in vivo examples of this method, including the inducible inactivation of mammary tissue specific genes (Wagner et al., 1997, *Nucleic Acids Res.,* 25:4323).

iii. Bac Rescue of Knock Out Phenotype

In order to verify that a particular genetic polymorphism/mutation is responsible for altered protein function in vivo one can "rescue" the altered protein function by introducing a wild-type copy of the gene in question. In vivo complementation with bacterial artificial chromosome (BAC) clones expressed in transgenic mice can be used for these purposes. This method has been used for the identification of the mouse circadian Clock gene (Antoch et al., 1997, *Cell* 89: 655).

Materials

Trypsin was from Flow Laboratories (Bioggio, Switzerland). Culture media, G418, fetal bovine serum (FBS), restriction enzymes, Pfu DNA Polymerase was purchased from Stratagene and Taq DNA polymerases were purchased from Eurogentec. (Liege, Belgium). The radioactive product myo-D-[2-$^3$H]inositol (17.7 Ci/mmol) was from Amersham (Ghent, Belgium). Dowex AG1X8 (formate form) was from Bio-Rad Laboratories (Richmond, Calif). ATP was obtained from Sigma Chemical Co. (St. Louis, Mo.). Forskolin was purchased from Calbiochem (Bierges, Belgium). Rolipram was a gift from the Laboratories Jacques Logeais (Trappes, France). PCDNA3 is an expression vector obtained from Invitorgen.

Dosage and Mode of Administration

By way of example, a patient can be treated as follows by the administration of a modulator of FPRL2 polypeptide (for example, an agonist, antagonist or inhibitor of FPRL2 polypeptide, of the invention). A modulator of FPRL2 polypeptide of the invention can be administered to the patient, preferably in a biologically compatible solution or a pharmaceutically acceptable delivery vehicle, by ingestion, injection, inhalation or any number of other methods. The dosages administered will vary from patient to patient; a "therapeutically effective dose" can be determined, for example, by the level of enhancement of function (e.g., as determined in a second messenger assay described herein). Monitoring HBP polypeptide binding will also enable one skilled in the art to select and adjust the dosages administered. The dosage of a modulator of FPRL2 polypeptide of the invention may be repeated daily, weekly, monthly, yearly, or as considered appropriate by the treating physician.

In one embodiment, a patient can be treated to modulate the signalling activity of a FPRL2 polypeptide receptor by administering to a patient a sublethal dose of an agent which inhibits or promotes the signalling activity of FPRL2 polypeptide. A sublethal dose according to the invention, refers to a dose of an agent for inhibiting or stimulating a FPRL2 polypeptide signalling activity which is at or below the LD50 for the particular agent. In one embodiment, the dose of an agent which inhibits the signalling activity of FPRL2 polypeptide is between 1 fM and 1 M, preferably between 1 pM and 1 mM, and more preferably between 1 nM and 1 µM. In one embodiment, an agent useful for the modulation of FPRL2 polypeptide signalling may be an antibody which specifically binds to the ligand binding site of FPRL2 polypeptide. An amount of anti-FPRL2 polypeptide antibody needed to achieve a dosage useful for the modulation of FPRL2 polypeptide signalling will depend upon the level of expression of FPRL2 polypeptide, localization of receptor expression, and general state of the patient's own immune system, but generally range from 0.0005 to 5.0 mg of anti-FPRL2 polypeptide antibody or binding protein thereof per kilogram of body weight, with doses of 0.05 to 2.0 mg/kg/dose being more commonly used.

Pharmaceutical Compositions

The invention provides for compositions comprising a FPRL2 polypeptide modulator according to the invention admixed with a physiologically compatible carrier. As used herein, "physiologically compatible carrier" refers to a physiologically acceptable diluent such as water, phosphate buffered saline, or saline, and further may include an adjuvant. Adjuvants such as incomplete Freund's adjuvant, aluminium phosphate, aluminium hydroxide, or alum are materials well known in the art.

The invention also provides for pharmaceutical compositions. In addition to the active ingredients, these pharmaceutical compositions may contain suitable pharmaceutically acceptable carrier preparations which can be used pharmaceutically.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethyl-cellulose, or sodium carboxymethyl cellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hank's solution, Ringer' solution, or physiologically buffered saline. Aqueous injection suspensions may contain substances which increase the viscosity of the suspension, such as sodium carboxym ethyl cellulose, sorbitol, or dextran. Additionally, suspensions of the active solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For nasal administration, penetrants appropriate to the particular barrier to be permeated are used in the formulation. Such penetrants are generally known in the art.

The pharmaceutical compositions of the present invention may be manufactured in a manner known in the art, e.g. by means of conventional mixing, dissolving, granulating, dragee-making, levitating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc . . . . Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition with information including amount, frequency and method of administration.

EXAMPLES

Example 1

Cloning of Human FPRL2 Receptor

Human FPRL2 was cloned as follows: Oligonucleotides were synthesized, corresponding to the sequence of FPRL2. Oligonucleotide AS-204 had the forward sequence: 5'-ACCGGAATTCACCATGGAAACCAACTTCTCC-3' (SEQ ID NO: 14), and hybridized on the translation initiation codon of FPRL2. Oligonucleotide AS-416 had the sequence: 5'-ATCATCTAGAACGCAGGGTAGAAAGAGACAG-3' (SEQ ID NO: 15), and was complementary to a sequence located downstream of the translation stop codon of FPRL2. A PCR was performed, using human genomic DNA as template, and using oligonucleotides AS-204 and AS-416 as primers, with the following conditions:
PCR enzyme: Pfu DNA Polymerase (Stratagene).

Buffer supplied by the Stratagene with the enzyme, and added with 2.5% (v/v) of DMSO Cycles were as follow:

|     | Temperature (° C.) | Time (min) |
| --- | --- | --- |
| 1x  | 94 | 5' |
| 3x  | 94 | 1' |
|     | 48 | 1' |
|     | 72 | 2' |
| 30x | 94 | 1' |
|     | 60 | 1' |
|     | 72 | 2' |
| 1x  | 72 | 10' |

A PCR product of the expected size (1.1 kb) was obtained. This product was cloned in the EcoRI and XbaI sites of an expression vector (PCDNA3), using the EcoRI site introduced by the AS-204 oligonucleotide, and the XbaI site introduced by the AS-416 oligonucleotide and sequenced on both strand (FIG. 1).

Example 2

Tissue Distribution of FPRL2

Tissue distribution of human FPRL2-Reverse transcription-polymerase chain reaction (RT-PCR) experiments were carried out using a panel of poly(A)+RNA (spinal cord, thymus, pancreas, uterus, placenta, stomach, lung, spleen, testis, brain, heart, kidney, skeletal muscle, fetal liver, fetal brain, adrenal gland, bone marrow) and total RNA (pituitary, small intestine, liver, ovary, fetal aorta, adipose, monocytes, lymph node, T lymphocytes, B lymphocytes, PBMC, PMN, PBL).

Figure 2:
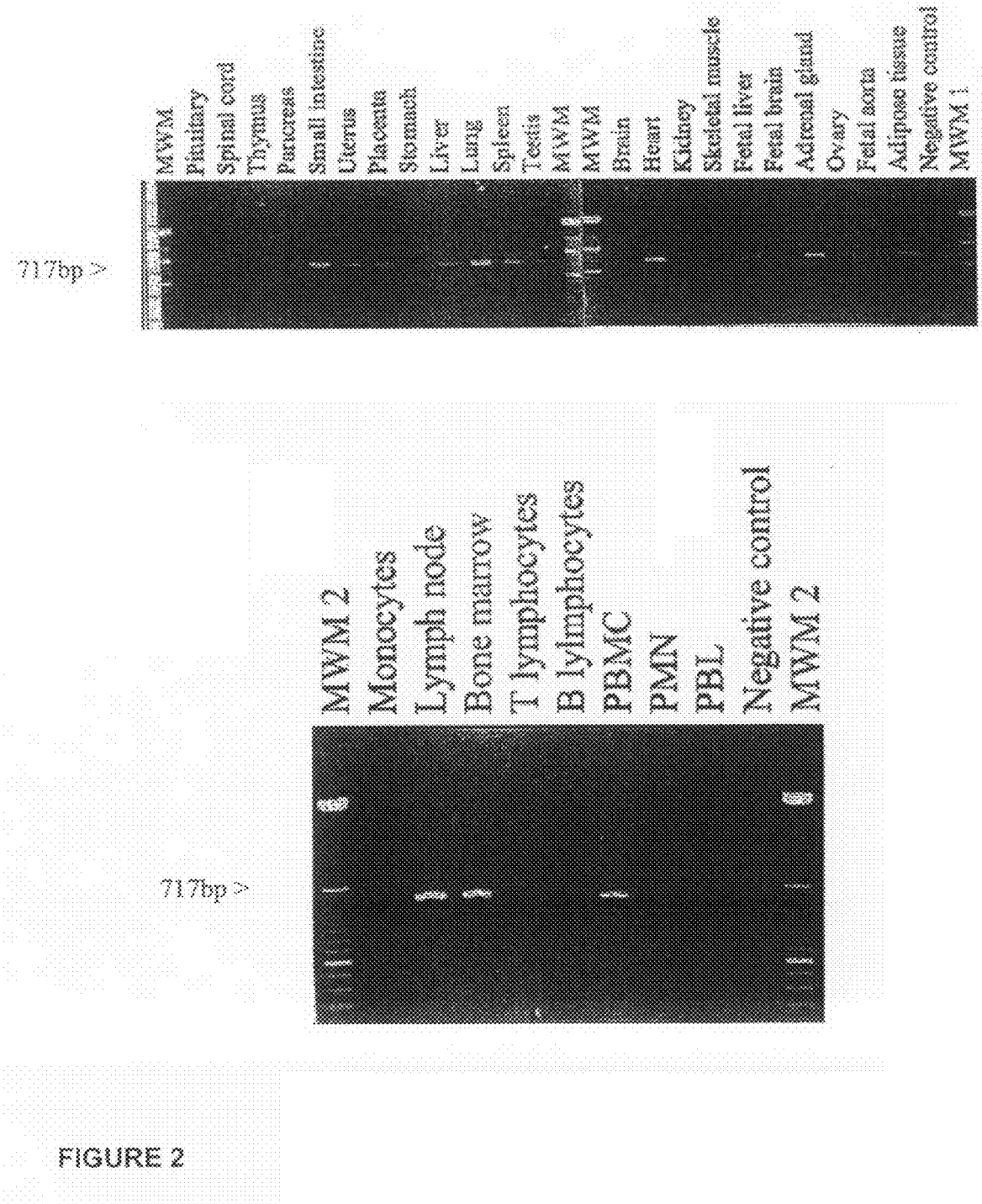
FIG. 2 shows the tissue distribution of the human FPRL2 receptor.

The FPRL2 primers were 5'-CGCACAGTCAACACCATCTG-3' (forward) (SEQ ID NO: 16) and 5'-AGCTGTTAAAAAAGGCCAAG-3' (reverse) (SEQ ID NO: 17), with an expected product size of 717 bp (FIG. 2). Approximately 50 ng of Poly(A)+RNA or 500 ng of total RNA was reverse transcribed with Superscript II (Invitrogen) and used for PCR. PCR was performed using the Taq polymerase under the following conditions: denaturation at 94° C. for 5 min, 30 cycles at 94° C. for 1 min, 56° C. for 1 min 30 s, and 72° C. for 45 s. Aliquots (10 µl) of the PCRs were analyzed by 1% agarose gel electrophoresis.

Example 3

Purification of the Natural Ligand of FPRL2 and Identification of a Fragment of HBP 1. Homogenate The purification was performed from 350 g of porcine spleen. The fresh organ was shopped and frozen in liquid nitrogen. Frozen organ was then brought to 4° C. in a solution of 20% acetonitrile (ACN) in water, in a ¼ organ/liquid proportion. The mixture was mixed, then reduced to an homogenate with an Ultraturax.

After homogeneization, the mixture was centrifuged at 10000 g for 30 minutes at 4° C.

The supernatant was frozen in liquid nitrogen and stored at −80° C.

2. First Step

Aliquots of 200 ml, corresponding to 50 g of organ, were diluted 4 times in water 0.1% trifluoroacetic acid (TFA) to reach a concentration of 5% ACN. 800 ml were then loaded on a Poros column 4.6×150 mm at 5 ml/min. The column was submitted to a gradient of ACN (supplemented with 0.1% TFA) from 5 to 70% at 6%/minute. Fractions of 1.25 ml were collected and tested for functional activity in an aequorin assay. Two regions of activity were detected on the HPLC profile and the corresponding fractions were conserved.

3. Second Step

The fractions corresponding to the two regions of activity were pooled. The pool was diluted 4 times in water 0.1% TFA and loaded on a C18 column 4.6×250 mm at 1 ml/min. The column was submitted to gradient of ACN in the presence of 0.1% TFA at a rate of 1%/min between 30 and 50%. Fractions of 1 ml were collected and tested for functional activity. Two regions of activity were detected. From this step on, the two regions were treated separately.

4. Third Step

The fractions corresponding to the second region (higher percentage of acetonitrile) from 2 runs C18 were pooled and concentrated in a speedvac to a final volume of 50 µl. This was then diluted 3 times in a mixture water/30% ACN/0.1% TFA. This final volume was loaded on a size-exclusion column Superdex peptide PE 7.5×300 mm (Pharmacia Biotech) equilibrated with the dilution buffer. The run was conducted at 0.5 ml/min and fractions of 0.25 ml were collected and tested for functional. activity.

5. Fourth Step

Figure 3:
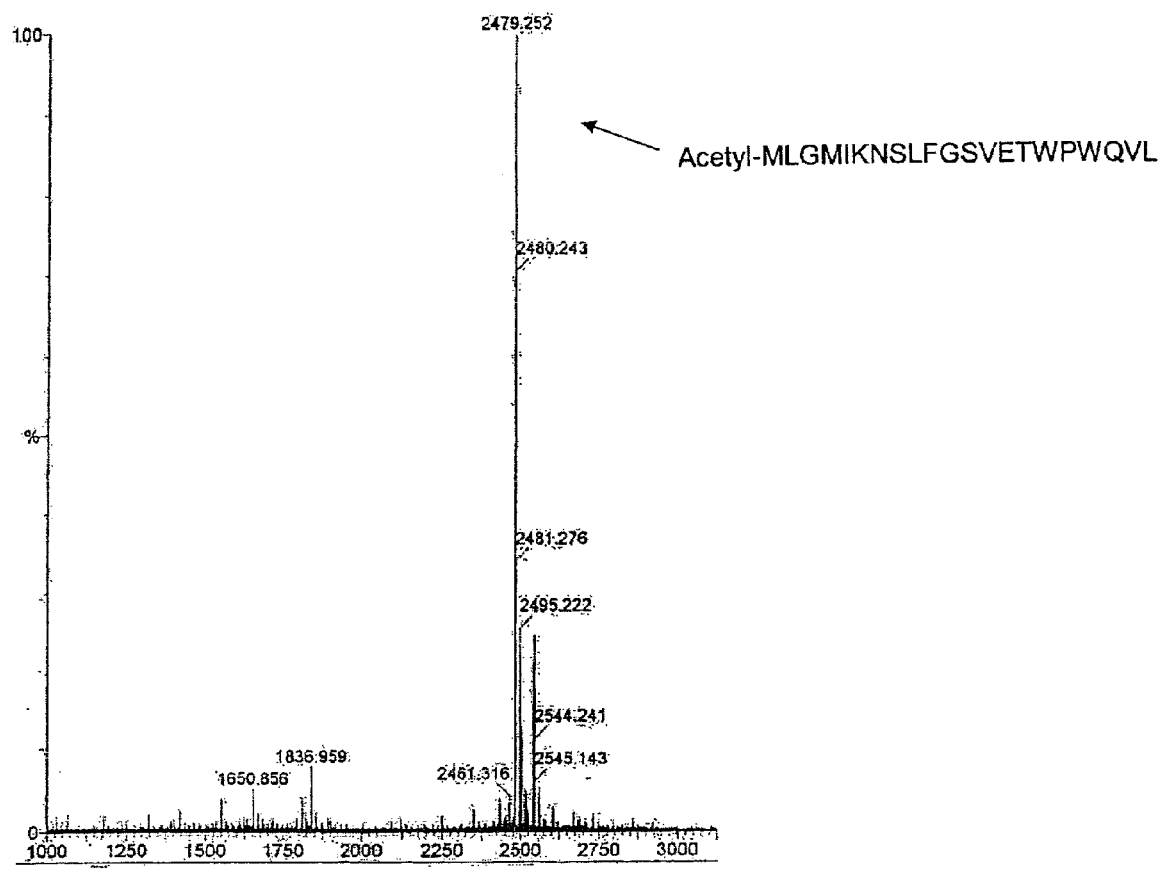
FIG. 3 shows the mass spectrum of the active fraction on a Maldi Q-TOF mass spectrometer. The major monoisotopic mass is indicated by an arrow, as well as its sequence (SEQ ID NO: 18)

The active fractions from one step 4 were pooled and diluted 4 times in water 0.1% TFA. The final volume (2 ml) was loaded at 0.2 ml/min on a C4 column 2.1×250 mm. The column was submitted to a gradient of ACN in the presence of 0.1% TFA at a rate of 0.3%/min between 30 and 50%. The fractions were collected manually according to the absorbance profile and tested for functional activity. This step was repeated 3 times. The purity of the final active fraction was checked by loading an aliquot of it on a C18 column 1×250 mm. This fraction was then dried, resuspended in 20 mM ammonium bicarbonate, boiled, digested by trypsin (50 ng) overnight and finally analysed on a MALDI-Q-TOF mass spectrometer. Direct monoisotopic mass fingerprinting allowed to identify the following peptide: Acetyl-MLG-MIKNSLFGSVETWPWQVL (Sequence ID NO: 18) which corresponds to the 21 first amino acids of the porcine HBP (FIG. 3). The 21 first amino acid of human HBP are 100% identical to the 21 first amino acid of porcine HBP.

Example 4

Functional Assay for FPRL2

FPRL2 expressing clones have been obtained by transfection of CHO-K1 cells to coexpressing mitochondrial apoaequorin and Galpha16, limiting dilution and selection by northern blotting. Positive clones were used for screening with porcine spleen extracts prepared as described above. A functional assay based on the luminescence of mitochondrial aequorin intracellular $Ca^{2+}$ release (Stables et al., 1997, Anal. Biochem. 252:115-126; incorporated herein by reference) was performed as described (Detheux et al., 2000, J. Exp. Med., 192 1501-1508; incorporated herein by reference). Briefly, cells were collected from plates in PBS containing 5 mM EDTA, pelleted and resuspended at $5×10^6$ cells/ml in DMEM-F12 medium. Cells were incubated with 5 µM Coelenterazine H (Molecular Probes) for 4 hours at room temperature. Cells were then washed in DMEM-F12 medium and resuspended at a concentration of $0.5×10^6$ cells/ml. Cells were then mixed with test agonist peptides or plates containing tissue extracts and the light emission was recorded for 30 sec using a Microlumat luminometer (Perkin Elmer). Results are expressed as Relative Light Units (RLU).

Example 5

Activation of Cells Expressing FPRL2 by N-Terminal Peptide of HBP

Figure 4:
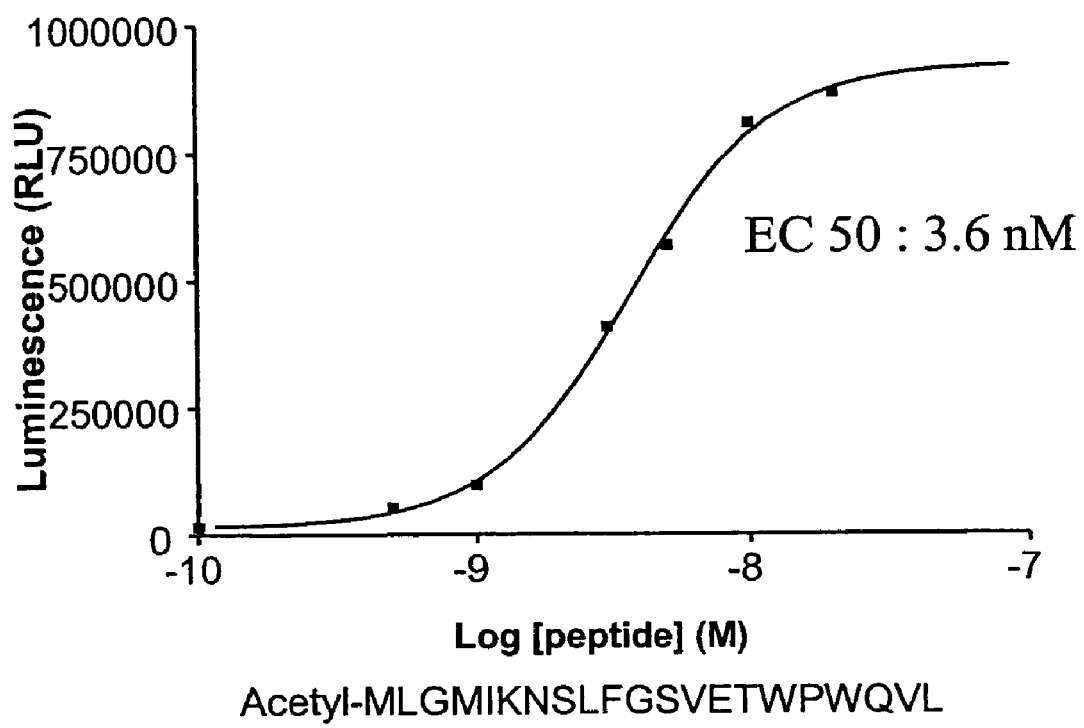
FIG. 4 illustrates the biological activity of the acetylated 21 amino acid peptide corresponding to the N-terminus of porcine HBP (SEQ ID NO: 18) on human FPRL2 receptor.

In order to investigate the potential effect of the N-terminal domain of HBP, we purified the natural peptide from the active spleen fraction (this peptide has the sequence shown in SEQ ID NO: 18), and tested its ability to trigger intracellular calcium release in a cell line coexpressing the FPRL2 receptor and apoaequorin. We have used the aequorin assay as previously described in Detheux et al. (2000 J. Exp. Med. 192, 1501-1508). As shown in FIG. 4, the peptide of 21 amino acids corresponding to the N-terminal end of porcine HBP was able to activate the FPRL2 at nanomolar concentration (mean $EC_{50}$ of 3.6 nM).

Figure 5:
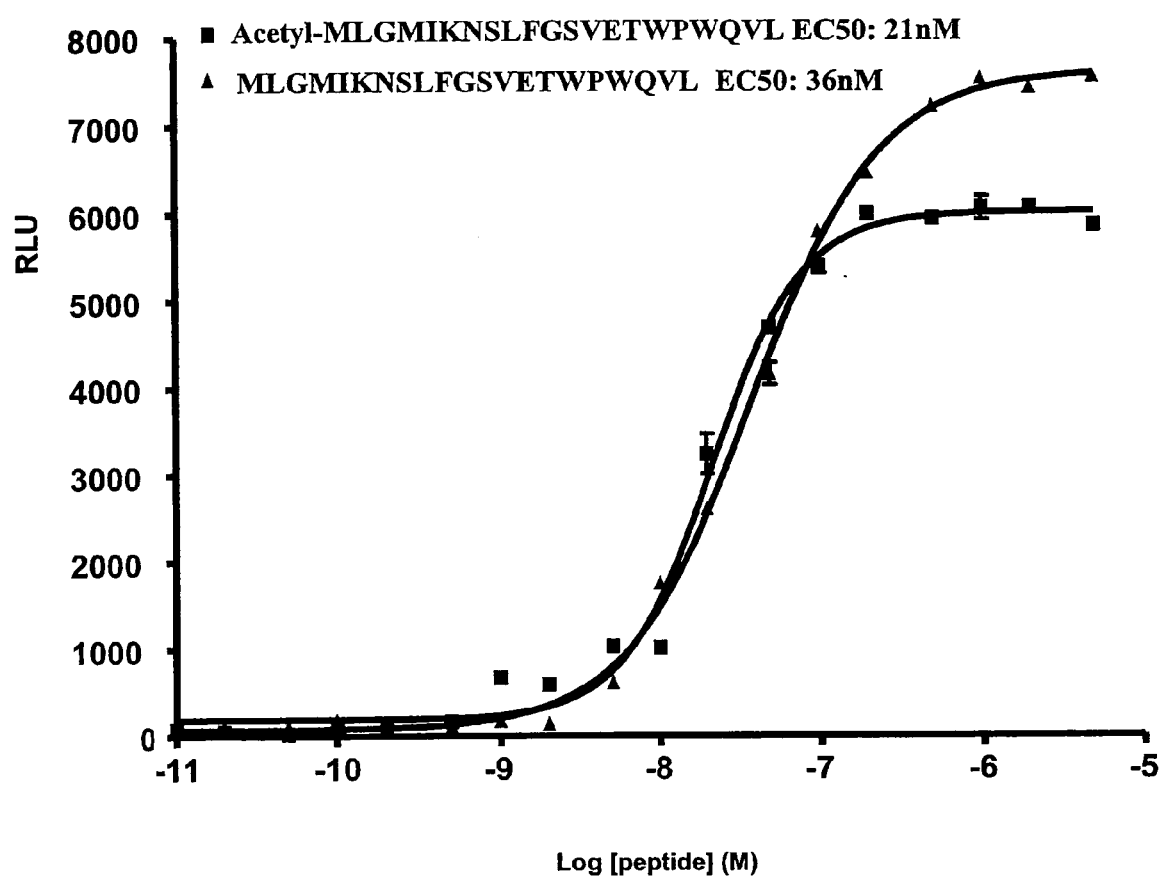
FIG. 5 illustrates the biological activity of the acetylated (SEQ ID NO: 18) and non-acetylated (SEQ ID NO: 19) 21 amino acid peptide on human FPRL2 receptor.

In order to investigate whether the acetyl group, located at the NH2 end of the peptide shown by SEQ ID NO: 18, modulates the activity of the peptide or not, we synthesized this peptide of 21 amino acids with and without acetyl group at its NH2 end. As shown in FIG. 5 the acetyl group does not modify the activity of the peptide on FPRL2 receptor (mean $EC_{50}$ of 21 nM for acetylated peptide and $EC_{50}$ of 36 nM for non acetylated peptide).

Example 6

N-Terminal Peptide of HBP Activates Specifically the FPRL2 Receptor

Figure 6:
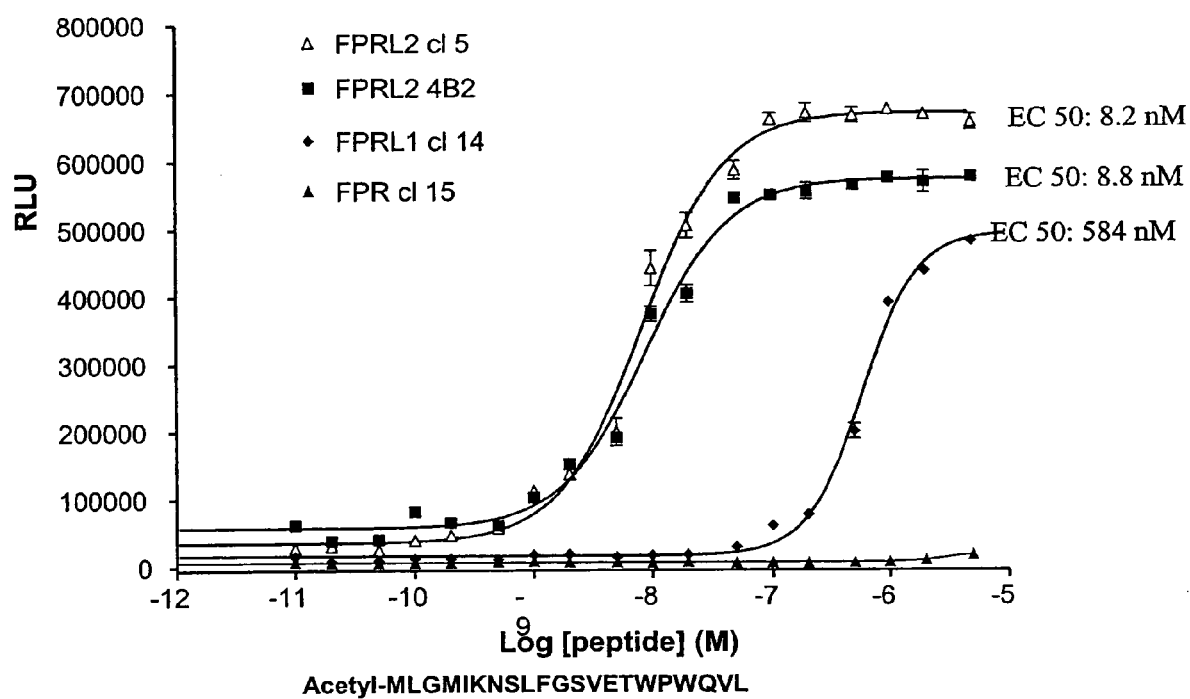
FIG. 6 shows the biological activity of the acetylated 21 amino acid peptide (SEQ ID NO: 18) on human FPR receptor family.

In order to investigate the specificity of the above-mentioned peptide on FPRL2 receptor, we tested the activity of this peptide on two other members of FPR family: FPR receptor and FPRL1 receptor. As shown in FIG. 6, the peptide of 21 amino acids (SEQ ID NO: 18) was able to activate the FPRL2 receptor at nanomolar concentration (mean $EC_{50}$ of 8.8 and 8.2 nM, notice: in this experiment two different clones expressing FPRL2 were tested) but was not able to activate FPR and activated FPRL1 only at high concentration (mean $EC_{50}$ of 584 nM).

Example 7

FPRL2 is a Gi Coupled Receptor

The cAMP concentrations were determined using a HTRF kit, according to manufacturer specifications (HTRF kit, Cis bio International, cat n° 62AM2PEC).

Cells in mid-log phase, grown in media without antibiotics for 18 hours prior to the experiment, are detached by gentle flushing with PBS-EDTA, recovered by centrifugation and resuspended in KRH-IBMX (1 mM) at the concentration of $4.2×10^5$ cells/ml.

For the agonist assay, 6 µl/well of Forskolin 4× (10 µM fmal concentration) and 6 µl of increasing amounts of tested agonist (4×) (peptide 2478: which corresponds to the peptide disclosed in SEQ ID NO: 18) or Forskolin 4× (10 µM final concentration) for the FK control are dispensed in 96 well plate (Costar, cat n°: 3694). 12 µl/well of cell suspension (5000 cells/well) are added onto each well and incubated for 30 min at room temperature.

The reaction was stopped by successive addition of 12 µl of cAMP-XL665 and 12 µl anti-cAMP cryptate diluted in Lysis buffer. The plate was incubated for 60 min. at room temperature and read on Rubystar (BMG). Results are calculated from the 665 nm/620 nm ratio and expressed in Delta F (%). A calibration curve is obtained by plotting deltaF % versus cAMP concentrations. Delta F % obtained from samples can be reported on the calibration curve to deduce respective cAMP concentrations (nM) produced by each sample.

Figure 7:
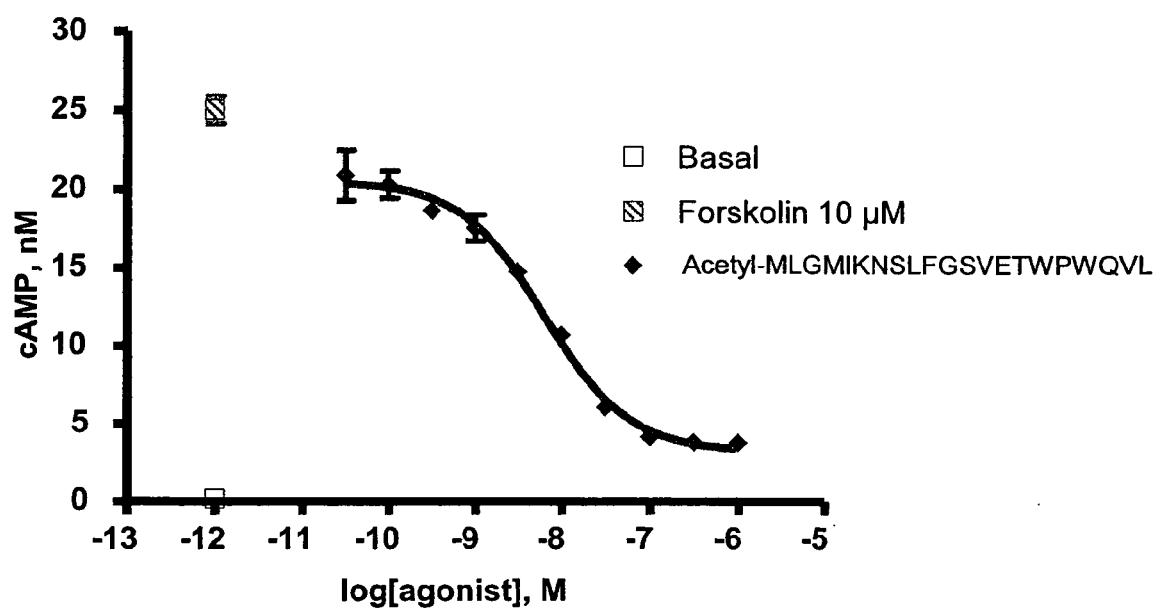
FIG. 7 shows that FPRL2 receptor is coupled negatively to adenylate cyclase in presence of forskolin. Figure discloses SEQ ID NO: 18.

The natural coupling properties and the intracellular signaling pathways activated by FPRL2, upon stimulation by SEQ ID NO: 18 were investigated in CHO-K1 cells expressing the human receptor and the aequorin. We first demonstrated that the FPRL2 receptor coupled negatively to adenylate cyclase in presence of forskolin (FIG. 7), while being unable to promote accumulation of cAMP in the absence of forskolin (not shown).

The peptide shown by SEQ ID NO: 18 is able to decrease the amount of cAMP produced in cells expressing the FPRL2 receptor in a dose-dependent manner and displays an agonist activity on FPRL2 with an $EC_{50}$ of 6.5+/−2.4 nM.

Example 8

Identification, Synthesis, and Characterization of Human FPRL2 Receptor and Ligand A) Material and Methods
Expression of Human FPRL2, FPRL1 and FPR.
The human coding sequences (accession numbers AC005946, M84562 and M60626, respectively) were amplified by PCR from human genomic DNA, cloned into the pcDNA3 (Invitrogen) and pEFIN3 (Euroscreen) vectors and sequenced. The pEFIN3 constructs were transfected, using Fugene 6, into CHO-K1 cells, expressing or not $G_{\alpha 16}$ and apoaequorin. G418-resistant clones were characterized for receptor expression by Northern blotting. A functional assay based on the luminescence of mitochondrial aequorin was performed as described (42). Results were expressed as relative light units (RLU) or as the percentage of the response to 20 µM ATP.

Purification of Bioactive Peptides.

Frozen porcine spleen (350 g) was homogenized in four volumes of ice-cold 20% $CH_3CN$ in water. The homogenate was centrifuged at 10,000 g for 30 minutes at 4° C. and snap-frozen in liquid nitrogen. Aliquots of 200 ml of supernatant were diluted four-fold in 0.1% trifluoroacetic acid (TFA) and loaded on a Poros R2 beads 4.6×150 mm column (Applied Biosystems) at 5 ml/min. A 5-70% $CH_3CN$ gradient (6%/min) in 0.1% TFA was applied, and 1.25 ml fractions were collected and tested for functional activity on FPRL2-expressing CHO-K1 cells in an aequorin assay. Two regions of activity (A1 and A2) were detected on the HPLC profile. The corresponding fractions were pooled, diluted four-fold in 0.1% TFA and loaded at 1 ml/min on a C18 4.6×250 mm column (Vydac), which was submitted to a 30-50% $CH_3CN$ gradient in 0.1% TFA. Two regions of activity were detected and subsequently treated separately. The 1 ml fractions corresponding to the first (A1, lower $CH_3CN$ concentration) and the second (A2, higher $CH_3CN$ concentration) regions from two runs were vacuum-concentrated to 50 µl. A1 and A2 were diluted three-fold in respectively 30% $CH_3CN$/0.05% TFA and 30% $CH_3CN$/0.1% TFA, and loaded on size-exclusion columns (SEC) (A1: TSK-gel Alpha-4000 7.8×300 mm, Tosoh Biosep; A2: Superdex peptide PE 7.5×300 mm, Amersham Pharmacia Biotech) submitted to a 0.5 ml/min flow rate of dilution medium. The active 0.25 ml fractions from one SEC were diluted four-fold in 0.1% TFA and loaded at 0.2 ml/min on a C4 2.1×250 mm column (Vydac), which was submitted to a 25-45% (A1) or 30-50% (A2) $CH_3CN$ gradient at 0.3%/min in 0.1% TFA. The fractions were collected manually according to the absorbance profile. For A1, the active fractions from one run were pooled, diluted five-fold in 0.1% TFA, and loaded at 0.05 ml/min on a C18 1×250 mm column (Vydac), which was submitted to a 23-50% $CH_3CN$ gradient at 0.45%/min in 0.1% TFA. The fractions were collected manually. For A2, the purity of the final active fraction was checked by loading an aliquot on a C18 1×250 mm column. The purification was repeated three times, with different protocols (i.e. the SEC step was replaced by a reverse-phase step on a C18 2.1×250 mm column submitted to a $CH_3CN$ gradient in 0.1% $H_3PO_4$ as ion-pairing agent). The protein concentration in active fractions was determined following SDS/PAGE, by comparison with aprotinin and lysozyme standards following silver staining.

Mass Spectrometry Analysis.

The active fractions were vacuum-dried, resuspended in 20 mM ammonium bicarbonate, heated to 100° C. for 5 min, digested by trypsin (50 ng) overnight or left intact, and purified by solid-phase extraction (C18 ZipTip, Millipore). The peptides were eluted in 1.5 µl of 70% $CH_3CN$/0.1% TFA onto a metallic MALDI target, dried, and then mixed with 1.5 µl of matrix mix (2 mg/ml 2,5-dihydroxybenzoic acid and 10 mg/ml α-cyano-4-hydroxycinnamic acid, 2 mM fucose, 5 mM ammonium acetate). Mass spectrometry analysis was performed on a Q-TOF Ultima Global mass spectrometer equipped with a MALDI source (Micromass), and calibrated using the monoisotopic masses of tryptic and chymotryptic peptides from bovine serum albumin. Ionization was achieved using a nitrogen laser (337 nm beam, 10 Hz) and acquisitions were performed in a V mode reflectron position. Microsequencing was performed by argon-induced fragmentation after selection of the parent ion.

Synthetic Peptides.

Acetylated or non-acetylated MLGMIKNSLFGSVETW-PWQVL(SEQ ID NO: 37) (HBP[1-21], F2L in this Example 8), NSLFGSVETWPWQVL (SEQ ID NO: 20) (F2L[7-21]), WKYMVM (SEQ ID NO: 21), and MLWRRKIG-PQMTLSHAAG (SEQ ID NO: 22)(SHAAG peptide derived from CCL23 N-terminus) were synthesized locally by using the solid phase Fmoc strategy (43) or custom made by Eurogentec. WKYMVM (SEQ ID NO: 21)and WKYMVm (SEQ ID NO: 23) were purchased from Phoenix Pharmaceuticals and FMLP from Neosystem. Monoisotopic masses and sequences of all peptides were verified by mass spectrometry. F2L and WKYMVM (SEQ ID NO: 21) from different origins displayed the same properties. At high concentrations, HBP-derived peptides were dissolved in DMSO and heated at 50° C. for 10 min, due to their high hydrophobicity. Intermediate dilutions were made in 50% $CH_3CN$, and were further diluted 40-fold in assay buffer to reach working concentration.

Quantitative RT-PCR

For the quantitative PCR, FPRL2 transcripts were detected by RT-PCR in cDNA from human blood cell populations obtained commercially (Clontech) or prepared locally as described (44). Primers were 5'-CTGGCCACACCGT-TCTGT-3' (SEQ ID NO: 24) as forward, 5'-GGCCATGG-TAATGAACACGTT-3' (SEQ ID NO: 25) as reverse for FPRL2. Amplification of GAPDH transcripts was performed as a control of the quality of cDNA (not shown). FPRL2 transcripts were detected by quantitative RT-PCR (TaqMan) in total or polyA+RNA samples from human tissues obtained commercially (Clontech and Ambion) or prepared locally (DCs). Primers were 5'-TTACCATGGCCAAGGTCTTTCT-3' (SEQ ID NO: 26) as forward, 5'-GCAGACTGTGAT-GATGGACATAGG-3' (SEQ ID NO: 27) as reverse and 5'FAM-TCCTCCACTTCATTATTGGCTTCAGCGT-3'DABSYL (SEQ ID NO: 28) as probe for FPRL2, and 5'-GAAGGTGAAGGTCGGAGTC-3' (SEQ ID NO: 29) as forward, 5'-GAAGATGGTGATGGGATTTC-3' (SEQ ID NO: 30) as reverse and 5'FAM-CAAGCTTCCCGTTCT-CAGCC-3'DABSYL (SEQ ID NO: 31) as probe for the reference housekeeping gene (GAPDH). Primers were used at 900 nM and probes at 200 nM. Standard curves were run systematically for the two genes, and the transcript copy number of FPRL2 was normalized to the GAPDH transcript copy number for each sample.

Monoclonal Antibodies and Flow Cytometry

Antibodies were generated by injecting BALB/c mice with 100 µg pcDNA3-FPRL2 as described (45). Sera were tested by FACS on the CHO-K1-FPRL2 cell line, and immune mice were used to generate monoclonal antibodies by standard hybridoma technology, using the NSO myeloma cell line. The Ig class of selected hybridomas was determined with a mouse mAb isotyping kit (IsoStrip, Boehringer Mannheim). The antibodies were tested using flow cytometry, performed using anti-FPRL2 antibodies or control IgG2a at 1 µg/ml (for CHO-K1 cells) or 5 µg/ml (for primary cells) in PBS containing 0.1% BSA, 0.1% sodium azide, and FITC-conjugated γ-chain-specific goat anti-mouse IgG (Sigma) as secondary antibody. Fluorescence of 10,000 cells was assayed using a FACScan flow cytofluorimeter (Beckton Dickinson). Intracytoplasmic staining was realised using Cytoperm/Cytowash (Becton Dickinson) according to manufacturer's instructions.

Intracellular Cascade Assays

The cAMP concentrations were determined using a homogeneous time-resolved fluorescence (HTRF) kit (Cis Bio International). Briefly, cells were detached, resuspended in Krebs Ringer Hepes buffer containing 1 mM 3-Isobutyl-1-methylxanthine, and submitted to 10 µM forskolin, alone or together with increasing concentrations of agonists for 30 min at room temperature. The reaction was stopped by the successive addition of cAMP-L665 and anti-cAMP cryptate diluted in lysis buffer. The plates were incubated for 60 min at room temperature and read on a Rubystar fluorimeter (BMG). Results were calculated from the 665 nm/620 nm ratio and expressed in delta F (%). A calibration curve was obtained by plotting delta F % versus cAMP concentrations. ERK1/2 activation was assayed by Western blotting, using an anti-phospho-p42/44 monoclonal antibody (E10, Cell Signaling Technology) as described (46). The aequorin-based assay was performed with or without overnight pretreatment with 100 ng/ml Pertussis toxin. It was shown that such Pertussis toxin pretreatment did not inhibit the functional response to ATP in these cells. For FPRL2 polymorphism analysis, HEK cells were transiently transfected with empty and wild-type or Asp338His FPRL2-containing pcdna vector using calcium phosphate method. Cells were recovered 48 hours later and used for FACS or cAMP experiments.

Binding Assays

A modified F2L peptide, bearing a carboxy-terminal tyrosine, was shown to display a potency similar to that of wild-type F2L in the aequorine assay. 5 µg of peptide was labeled with 2 mCi of $^{125}$I using the Iodogen method. Following separation of unbound $^{125}$I, the resulting specific activity of the peptide was estimated to 900 Ci per mmole. [$^{125}$I]-WKYMVm (SEQ ID NO: 23) (2200Ci/mmole) was purchased from Perkin Elmer Life Sciences. FPRL2, FPRL1 and FPR-expressing CHO-K1 cells were plated in 24 wells plates (200,000 cells per well for FPRL2, and 100,000 cells per well for the two other receptors). The next day, the cells were washed twice with a KRH buffer containing 280 mM saccharose and, for FPRL1 and FPR, 0.1% NaN$_3$. For saturation binding assays, cells were incubated with various amounts of F2L-[$^{125}$I]Tyr and non-specific binding was determined by using 1 µM F2L as competitor. For competition binding assays, cells were incubated with 100,000 cpm of F2L-[$^{125}$I]Tyr or 10,000 cpm of [$^{125}$I]-WKYMVm (SEQ ID NO: 23) and various amounts of F2L or other peptides as competitors, in KRH buffer supplemented with 5% BSA, for 90 min at room temperature. Cells were washed twice with ice cold buffer, total radioactivity was recovered with 1 M NaOH and counted in a gamma counter for 2 min.

Chemotaxis and Ca2+ Mobilization Assays on Primary Cells

Monocyte-derived DCs were generated either from the adherent fraction of PBMCs cultured with GM-CSF (800 U/ml) and Il-4 (500 U/ml), or from Percoll-purified monocytes cultured with GM-CSF (50 ng/ml) and IL-13 (20 ng/ml), for 5 to 7 days. For Ca$^{2+}$ mobilization assay, monocytes were obtained by negative selection with the Monocyte Isolation Kit II (Miltenyi Biotec). Cell migration in response to F2L and FMLP and Mip1 alpha used as controls was evaluated by using a 48-well microchemotaxis chamber technique as described (48). For Ca$^{2+}$ mobilization assays, monocyte-derived DCs or monocytes (5×10$^5$ cells/ml in HBSS without phenol red but containing 0.1% BSA and 1 mM Probenecid (Sigma)) were loaded with 4 µM Fluo 4 (Molecular Probes) for 1 h at 20° C. in the dark. The loaded cells were washed twice, resuspended at 1 to 2×10$^6$ cells/ml and 50 µl of cell suspension was distributed per well of a 96 well plate (Viewplate, Packard Bioscience). Reading was performed in a Fluostar fluorimeter (BMG) at 25° C.: 50 µl of ligand-containing medium was injected, and the fluorescence at 520 nm was recorded every second for 1 to 3 min. Each condition was performed in triplicate, the mean fluorescence for each time point was calculated, and the curves were normalized by subtracting the mean value of the five measurements preceding the injection.

B) Results

Isolation and Identification of the F2L Peptide (SEQ IN NO18) as an Endogenous Ligand of FPRL2.

Figure 9:
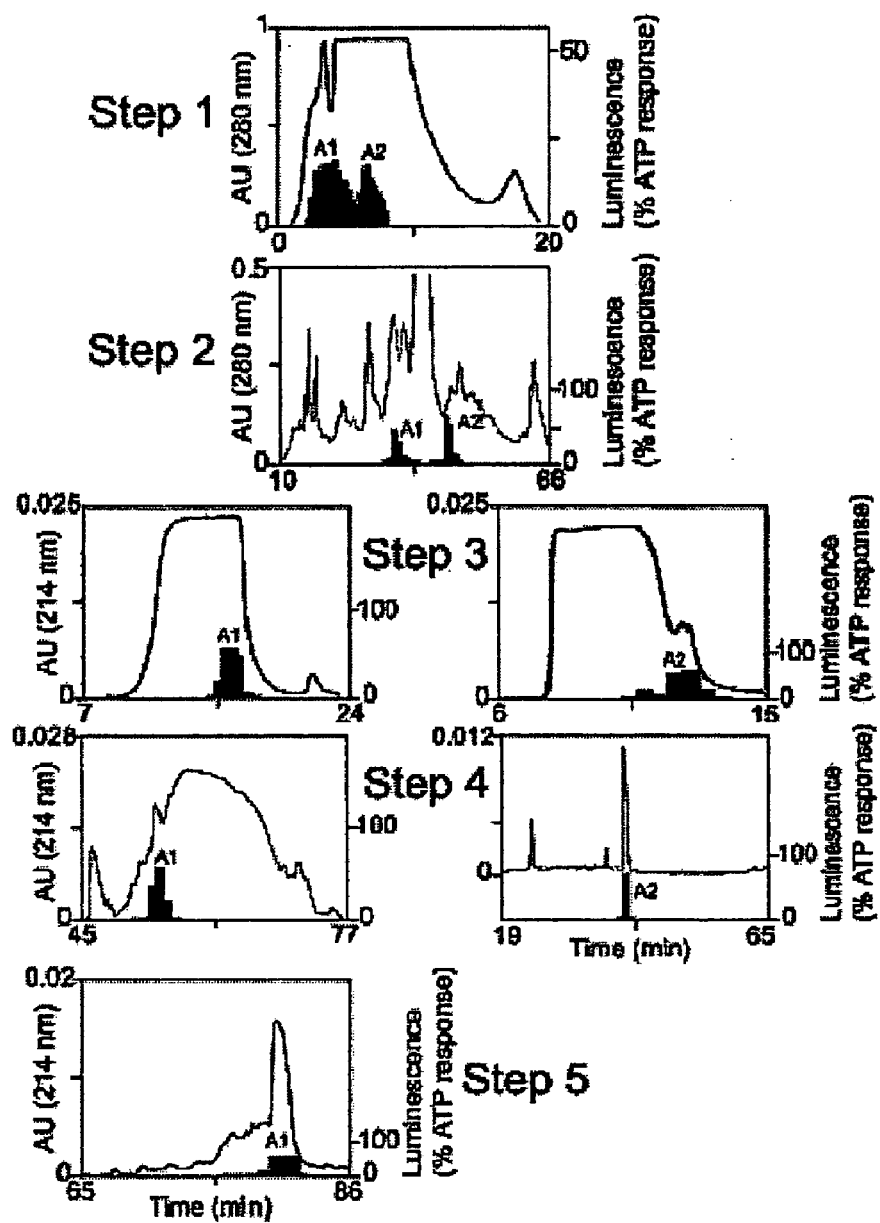
FIG. 9. Purification from porcine spleen of the natural ligand of FPRL2. A porcine spleen homogenate was first fractionated by HPLC onto a Poros column (Step 1). The absorbance (AU) and biological activity on FPRL2-expressing CHO-K1 cells are shown. The luminescence measured in an aequorin-based assay (black bars) was normalized to the response obtained for 20 μM ATP. A1 (Activity 1) and A2 (Activity 2) represent the two active regions on the HPLC profile. They were processed together onto a C18 column (Step 2). Thereafter, A1 and A2 were purified separately onto a SEC column (Step 3), a C4 column (Step 4) and for A1, a last C18 column (Step 5). The X axis is zoomed to focus on the region of interest.
Figure 10:
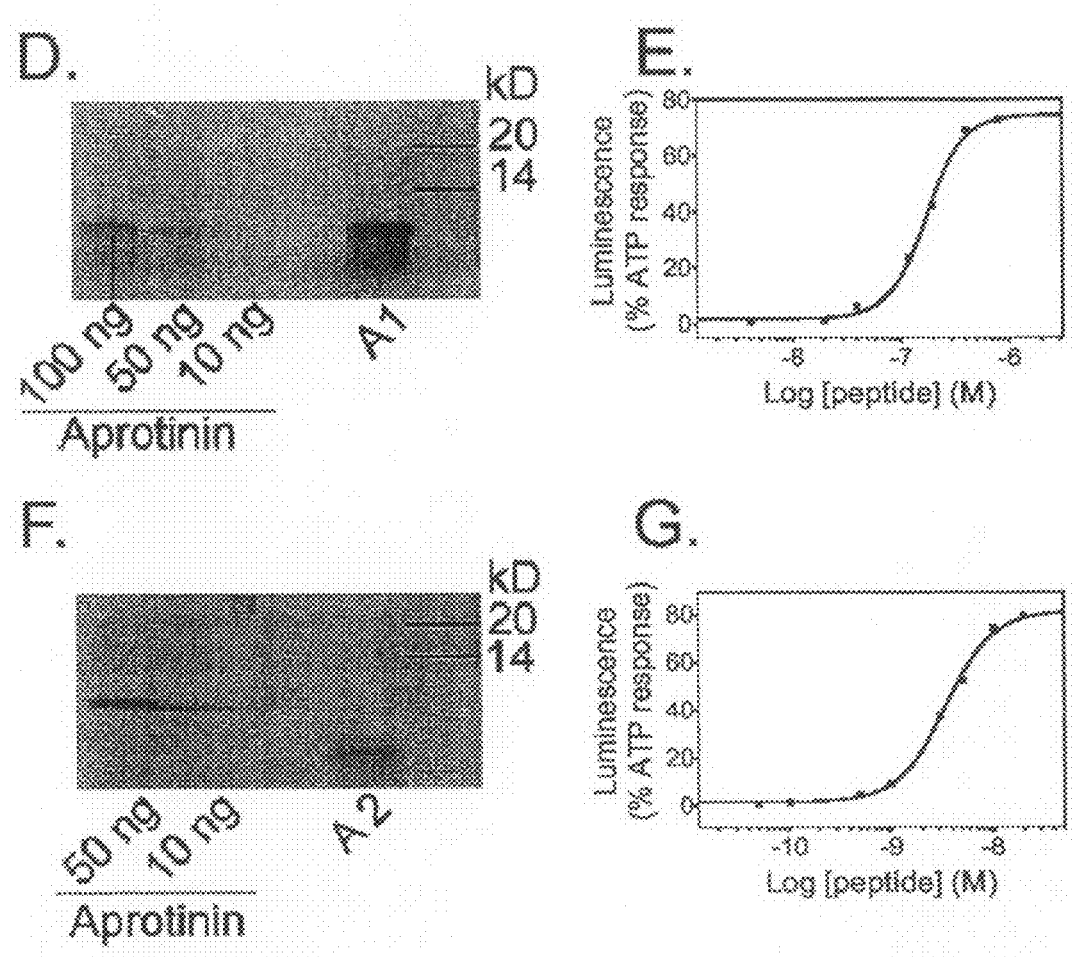
FIG. 10. Identification of F2L as a high affinity natural ligand of FPRL2. A. Mass spectrometry analysis of the undigested fraction A2 resulting from Step 4, using a Maldi Q-TOF mass spectrometer. B. Sequences corresponding to the major peaks of the mass spectra of trypsin-digested A1 (Step 5) (SEQ ID NOS 33-34, respectively, in order of appearance) and A2 (Step 4) (SEQ ID NOS 18 and 20, respectively, in order of appearance) fractions, or undigested A2. All microsequenced peptides were found to derive from the porcine heme-binding protein (HBP). The F2L peptide (A2 fraction) is amino-terminally acetylated. Ac: acetyl. C. Amino acid sequence alignment of human (SEQ ID NO: 8), mouse (SEQ ID NO: 10) and porcine (SEQ ID NO: 35) HBP. The sequence corresponding to the F2L peptide (represented in bold) is identical in human and porcine HBP. The region containing tryptic peptides recovered from fraction A1 is boxed (human HBP: NM 015987 ; murine HBP: NM 013546). D. The A1 fraction (Step 5) was migrated onto SDS-PAGE, together with 10, 50 and 100 ng of aprotinin as standards. The gel was silver-stained and it was estimated that the major band (6 kD) contained around 300 ng of peptide. E. Biological activity of the A1 fraction on CHO-K1 cells expressing human FPRL2, using the aequorin-based assay. F. The A2 fraction (Step 4) was migrated onto SDS-PAGE, together with 10 and 50 ng of aprotinin as standards. The gel was silver-stained and the amount of F2L (3 kD) was estimated to 40 ng. G. Biological activity of F2L (A2, Step 4) on CHO-K1 cells expressing human FPRL2, using the aequorin-based assay.

We developed, as a screening assay, CHO-K1 cell lines coexpressing human FPRL2, apoaequorin and Galpha 16. This allowed to test fractions from human lymphoid organ extracts, conditioned media of leukocyte populations, and inflammatory fluids. A biological activity, specific for FPRL2-expressing cell lines, was detected in fractions resulting from the reverse phase HPLC fractionation of extracts from human spleen (data not shown). For practical reasons, we tested fractions from porcine spleen prepared in a similar way, and identified two regions of the profile containing specific activities for FPRL2 (activities A1 and A2, FIG. 9). Starting from 350 g of porcine spleen, these two activities were purified to homogeneity by five (A1) or four (A2) successive HPLC steps, the first two being common (FIG. 9). The sensitivity of both activities to proteinase K suggested a peptidic nature (not shown). The molecular mass of the active compounds was estimated by size-exclusion chromatography to about 6 kD for activity A1, and 3 kD for activity A2. From the absorbance of the peaks and the biological activities associated with them, the compound present in peak A1 appeared more abundant but less active than that of peak A2. The two fractions were analyzed by SDS/PAGE and silver staining, in order to quantify approximately the active peptides by comparison with known amounts of aprotinin and lysozyme (FIGS. 10D and F). A concentration-action curve performed on the same fractions in the aequorin-based functional assay allowed to estimate an EC50 of 2.32±1.84 nM (n=2) for A2, and of 200±54 nM (n=4) for A1 (FIGS. 10G and E, respectively). Both peptides were analyzed by mass spectrometry, either without (A2) or after tryptic digestion (A1 and A2) (FIGS. 10A and B). For A2, analysis of the undigested peptide permitted to identify the entire microsequence as matching the first 21 aminoacids of a human intracellular heme-binding protein (HBP, accession number NM 015987) with an amino-termiinal acetylation (MW: 2478.28 daltons) (FIGS. 10A and B). For A1, six peptides, of which four were fragments of the two longest tryptic fragments shown in FIG. 10B, were also consistent with HBP. The porcine HBP was cloned by PCR from liver cDNA using degenerate primers, which allowed us to confirm the identification, and the perfect conservation of the first 21 aminoacids, as compared to the human sequence. This sequence was later confirmed following incorporation of porcine HBP ESTs in public databases (accession number AY662687). The two tryptic peptides from A2 covered 50 aminoacids in the amino-terminal domain of the 190 aminoacid-long sequence of porcine HBP (FIG. 10C). We assume that the amino-terminal end of A1 is common to that of A2, although it could not be demonstrated. The carboxy-terminal end of A1 was not determined precisely either, due to the large number of tryptic sites after Arg 56 of HBP. The purification was performed three times with distinct protocols, and the same peptides were identified by mass spectrometry in each case.

Comparative Pharmacology and Intracellular Signaling of Formyl Peptide Receptors.

Figure 11:
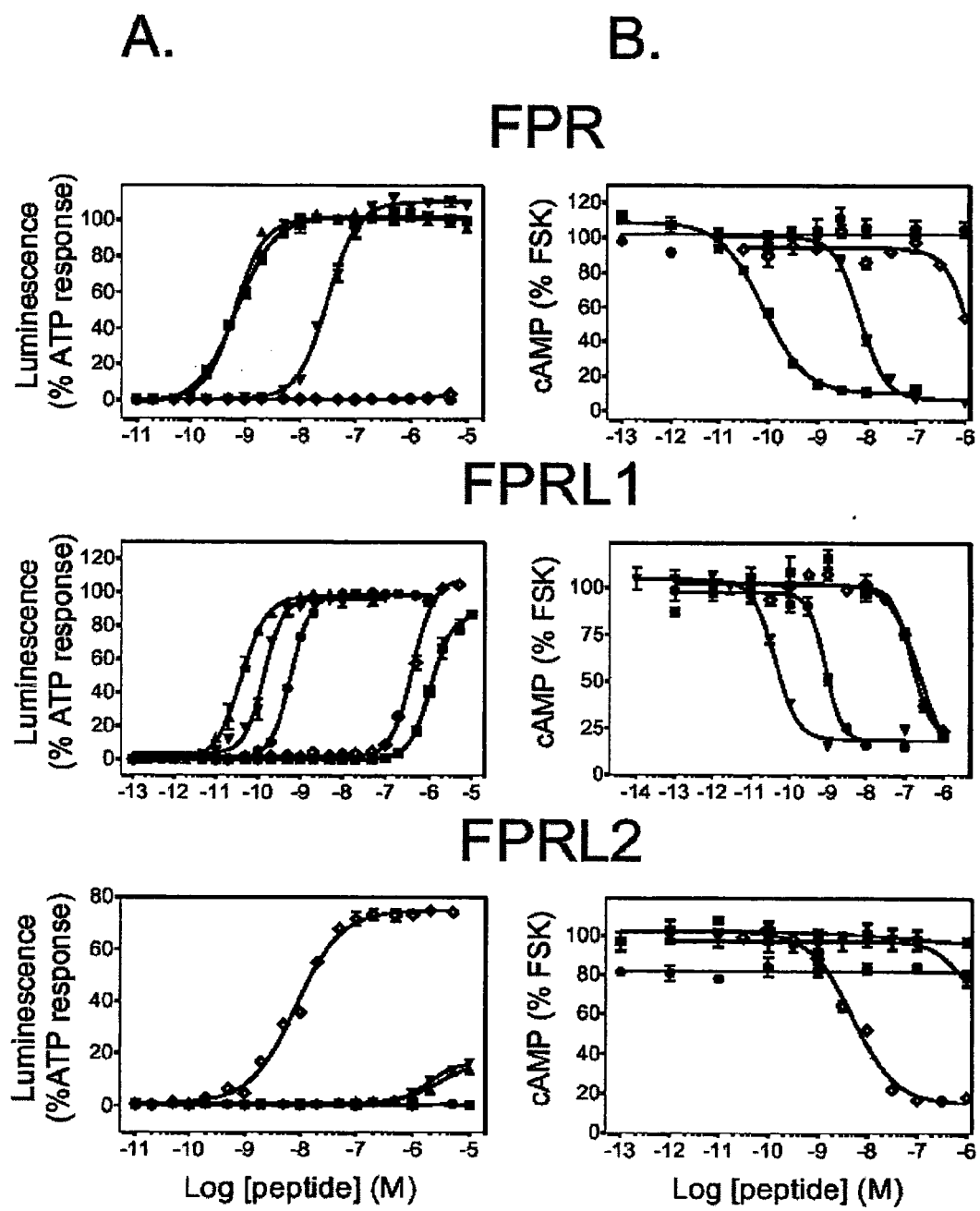
FIG. 11. Pharmacology of the formyl peptide receptors. A. Concentration-action curves of F2L (◇), FMLP (■), WKYMVm (SEQ ID NO: 23)(▲), WKYMVM (SEQ ID NO: 21)(▼) and SHAAG (Residues 14-18 of SEQ ID NO: 22)(●) peptides on CHO-K1 cells expressing FPR, FPRL1 or FPRL2, using the aequorin-based assay. Results are expressed as % of the response elicited by 20 μM ATP. B. Concentration-action curves of the same peptides on CHO-K1 cells expressing the three receptors, using a cAMP accumulation assay. Results are expressed as % of the cAMP level obtained in the presence of 10 μM forskolin, but in the absence of agonists. FSK: forskolin. C. Saturation binding assay (specific binding) on FPRL2-expressing CHO-K1 cells, using F2L bearing a carboxy-terminal [125I]-Tyr as tracer. D. Competition binding assay on FPRL2-expressing CHO-K1 cells using F2L-[125I]Tyr as tracer and F2L as competitor. E. and F. Competition binding assay on FPRL1 (E) and FPR (F) -expressing CHO-K1 cells using [125 I]-WKYMVm (SEQ ID NO: 23) as tracer, and WKYMVm (SEQ ID NO: 23)(▲) or F2L (◇) as competitors. G. Stimulation by F2L of FPRL2-expressing CHO-K1 cells cultured in the absence or presence of 100 ng/ml Pertussis toxin, using the aequorin-based assay. H. Concentration-action curves of acetylated (◇), non-acetylated (○) and [7-21]F2L (□) peptides on FPRL2-expressing CHO-K1 cells using the aequorin assay.
Figure 11:
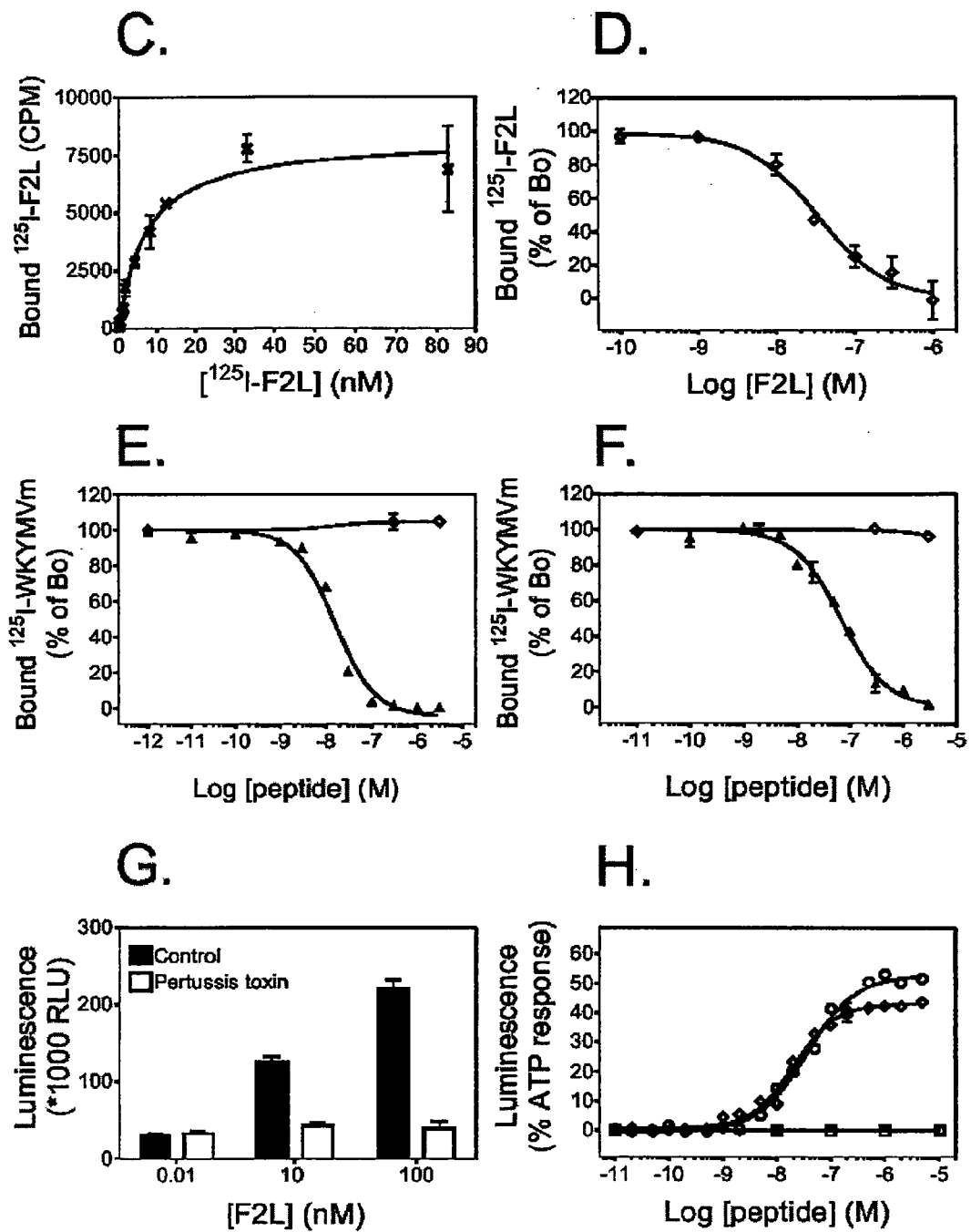
Figure 11:
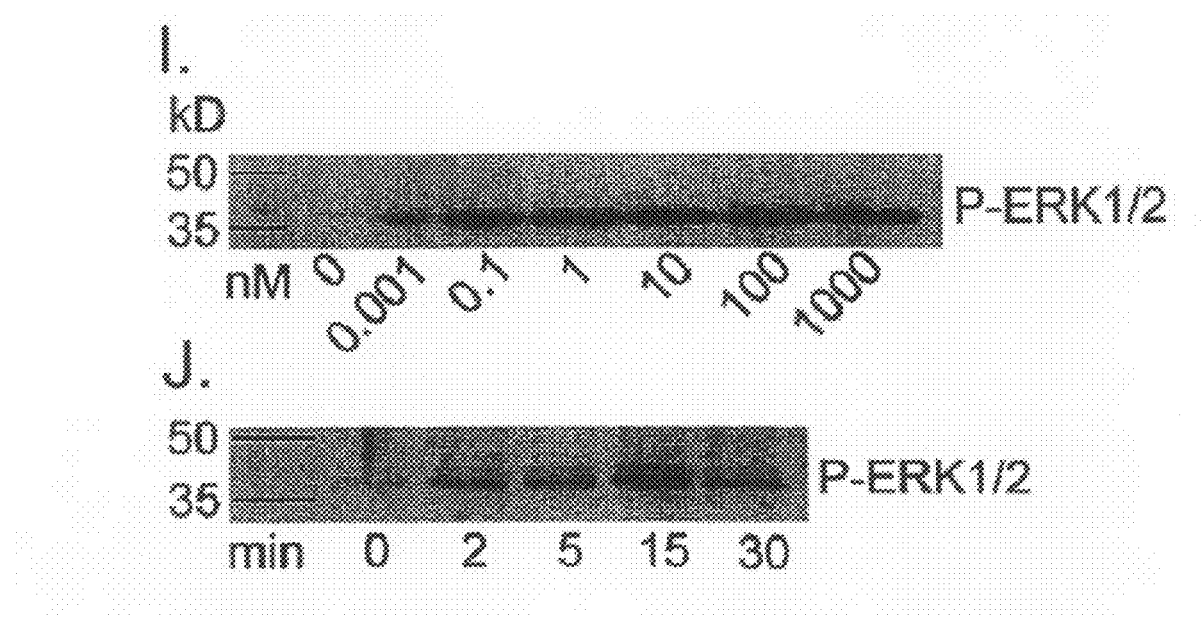

The pharmacology and signaling pathways activated by the three members of the human FMLP receptor family were investigated in CHO-K1 cells expressing the receptors, with or without G alpha 16 and apoaequorin (FIG. 11). The acetylated 21 amino acid peptide, named in Example 8 as F2L (for FPRL2 Ligand), was synthesized and tested in the aequorin-based assay on these three cell lines, as well as on wild-type CHO-K1 cells, and on CHO-K1 cells expressing ChemerinR and other GPCRs. The synthetic F2L peptide was shown to activate the FPRL2-expressing cells with a potency similar to that of the native peptide purified from spleen, and, with a much lower efficiency, FPRL1 and FPR (see below), but was completely inactive on all other cell lines tested (data not shown). F2L was also tested in a cAMP accumulation assay on CHO-K1 cells expressing FPRL2 but not G alpha 16. The synthetic peptide was found to inhibit the cAMP accumulation promoted by forskolin, and was unable to stimulate cAMP production by itself. In the same cells, F2L also promoted intracellular calcium release at low nanomolar concentrations (not shown) and induced at picomolar concentrations the phosphorylation of the ERK1/2 MAP-kinases (FIG. 11I). Kinetics study of MAPK activation showed a maximal phosphorylation at 15 min (FIG. 11J). Calcium signaling was totally inhibited by Pertussis toxin pretreatment, demonstrating the coupling of the FPRL2 receptor to the Gi family of heterotrimeric G proteins (FIG. 11G).

The comparative pharmacology of the three formyl peptide receptors was then studied in more detail, using F2L and four reference agonists of FPR and FPRL1 (FMLP, the hexapeptides WKYMVM (SEQ ID NO: 21) and WKYMVm (SEQ ID NO: 23), and the CCL23-derived SHAAG peptide (Residues 14-18 of SEQ ID NO: 22)). Concentration-action curves and the resulting functional parameters were established both in the aequorin-based assay, and the cAMP accumulation assay following stimulation by 10 µM forskolin (FIGS. 11A and B and Table 1). Among the tested peptides, F2L (SEQ ID NO 18) was by far the most potent on FPRL2, with an EC50 of 10 nM in the aequorin assay and 5 nM in the cAMP assay.

F2L appeared also as highly specific, as a weak activity was obtained on FPRL1 (EC50 of 567 and 234 nM in the aequorin and cAMP assays, respectively), while on FPR, only partial inhibition of cAMP accumulation was obtained for 1 µM F2L, and no activity was detected in the aequorin assay up to 5 µM. For the other peptides, the EC50 values obtained for FPR and FPRL1 (Table 1) were essentially as described in the literature. However, significant differences with published data were observed when testing the two W-hexapeptides on the FPRL2-expressing cells. Indeed, micromolar concentrations of these peptides were required in order to activate FPRL2 (while active at low nanomolar concentrations on FPR and FPRL1). As described, FMLP and SHAAG (Residues 14-18 of SEQ ID NO: 22) were inactive on FPRL2.

To further confirm that F2L is a specific high affinity ligand for FPRL2, we performed binding experiments. The results show that saturation binding assays performed on FPRL2-expressing CHO-K1 cells allowed KD of 11.7 ±4.9 nM to be determined, and a Bmax of roughly 30,000 receptors per cell (FIG. 11C) for the modified F2L peptide, bearing a carboxy-terminal tyrosine. Competition binding assays were performed with F2L, which displayed an IC50 of 33.4 ±0.2 nM (FIG. 11D and Table 1). The hexapeptides WKYMVM (SEQ ID NO: 21) and WKYMVm (SEQ ID NO: 23), SHAAG (Residues 14-18 of SEQ ID NO: 22), and FMLP, did not compete for FPRL2 binding up to concentrations of 3 µM (data not shown). We next confirmed the specificity of F2L for FPRL2 through binding experiments on FPR and FPRL1-expressing CHO-K1 cells, using [$^{125}$I]-WKYMVm (SEQ ID NO: 23) as a tracer. The IC50 values for WKYMVm (SEQ ID NO: 23) were 22.5 ±7.6 nM on FPRL1 (FIG. 11E), and 98.4 ±37.4 nM on FPR (FIG. 11F), but no competition was observed for F2L up to concentrations of 3 µM.

By analogy with formyl peptides, we investigated the role of the amino-terminal acetylation of F2L. The non-acetylated peptide was synthesized and shown to display an EC50 for FPRL2 similar to that of acetylated F2L (21.1±7.6 nM, n=3) (FIG. 11H). We also tested a truncated F2L variant lacking the first six aminoacids (F2L[7-21]), because mouse intracellular HBP was originally described by Edman sequencing as lacking this N-terminal part (47). This truncated peptide was found to be totally inactive in aequorin (FIG. 11H) and binding assay (not shown).

Distribution of Human FPRL2.

We investigated the presence of FPRL2 transcripts in various leukocyte populations by RT-PCR (FIG. 12A). As previously described (41), FPRL2 transcripts were the most abundant in monocytes and immature or mature monocyte-derived DCs. Maturation of DCs was induced by either LPS, LPS+ IFN-γ or CD40L for 3 to 24 hours, with no detectable variation of the level of expression of FPRL2 transcripts (FIG. 12A and not shown). They were either absent, or present at very low levels in all other cell populations tested. Quantitative RT-PCR was performed on a number of tissues, using DCs as reference.

Transcripts were found at low levels in most tissues, and at higher levels in lymph nodes, small intestine, lung and adipose tissue (FIG. 12B).

Monoclonal antibodies also were generated against human FPRL2 by genetic immunization, and characterized by FACS on CHO-K1 cell lines expressing FPR, FPRL1 or FPRL2 (FIG. 12C). The results indicate that one of the three monoclonals (1C4) was essentially specific for FPRL2, exhibiting poor recognition of FPRL1. The two other antibodies (1D2 and 1E1) recognized equally well both receptors. None however cross-reacted significantly with FPR. We investigated the ability of the antibodies to block F2L signaling on FPRL2-expressing CHO-K1 cells. Their blocking properties appeared however weak, as only partial inhibition of the signal was obtained with high concentrations (50 µg/ml) of 1C4 antibody (data not shown). These antibodies were used to confirm the presence of the receptor at the surface of DCs. The three monoclonals allowed to detect FPRL2 on immature and mature monocyte-derived DCs, although at variable levels. FPRL2 expression could be detected in 16 out of 24 donors. The experiments on one representative donor are displayed in FIG. 12D. We then compared intracytoplasmic and surface expression of FPRL2 on DCs by performing FACS analysis following permeabilization of the cells. We found significant intracellular expression of FPRL2 even for donors for which surface expression was very weak or undetectable (FIG. 12E). Additionally, down regulation of cell surface FPRL2 was observed when DCs were cultured in presence of 1 µM F2L for 48 hours (not shown). Altogether these data suggest that the variation of expression among donors can be attributed to trafficking parameters, such as internalization of the receptor following its stimulation by a ligand present in plasma. For 4 tested donors, maturation of DCs by LPS induced a slight decrease in surface expression of FPRL2 (FIG. 12F). Finally, we evaluated the only variant of FPRL2 described to date (accession number AAA58482), characterized by an aspartic acid to histidine substitution at position 338. No difference in expression or functional response (cAMP inhibition) was detected following transient expression in HEK cells, as compared to the FPRL2 form used initially (data not shown).

Biological Activity of F2L in Primary Immune Cells.

The biological function of F2L was investigated on leukocyte populations. By analogy to the role of FPR and FPRL1 in chemoattraction, and given the distribution of FPRL2, we focused on the measurement of calcium mobilisation and chemotaxis on monocytes and monocyte-derived DCs.

The results show that F2L promoted intracellular $Ca^{2+}$ flux in immature DCs (FIG. 13A), as well as mature DCs (not shown), in a dose-dependent manner. The amplitude of the response, although variable according to individuals, was comparable to that resulting from the stimulation by 10 nM FMLP (FIG. 13B). Out of 12 donors tested, a strong response was obtained in 7 cases, a weak response in 2 cases, and no response for 3 donors. This is attributed to the variable expression level of FPRL2, as determined by FACS analysis. Calcium mobilization was also observed in purified monocytes, in response to 100 nM F2L, although the amplitude of the signal was lower than with DCs (FIG. 13C). Human F2L also promoted ex vivo migration of immature DCs and monocytes (FIGS. 13D and E). Cell migration in response to F2L was mainly due to chemotaxis rather than chemokinesis as assessed in checkerboard experiments (data not shown). Maximal chemotactic responses were obtained for concentrations of 300 pM to 1 nM. The bell-shaped chemotactic response, with a maximum corresponding to concentrations below the EC50 derived from other functional assays, is typically observed for other chemotactic factors such as chemokines.

In this example, a natural ligand for the receptor FPRL2 has been identified. Starting from spleen, F2L has been isolated and characterized, as the first natural agonist displaying both high affinity and high selectivity for FPRL2. F2L binds and activates FPRL2 in the low nanomolar range, while the previously described ligands of the receptor (annexin I-derived Ac-1-25, bacterial Hp 2-20, and synthetic W peptides) are essentially FPRL1 agonists displaying weak activities on FPRL2. It should be noted that the synthetic hexapeptides WKYMVM (SEQ ID NO: 21) and WKYMVm (SEQ ID NO: 23) were initially described as high affinity agonists of FPRL2, on the basis of experiments conducted on purified leukocyte populations or FPRL2-expressing HL-60 cells (40, 41). Other data contradict these observations, describing activities of these peptides in the micromolar range on FPRL2 expressed in RINm5F (40) or HEK 293 cells (39). These two peptides effectively required micromolar concentrations to elicit calcium influx in FPRL2-expressing CHO- K1 cells, while they were active at low nanomolar concentrations on FPR and FPRL1 expressed in the same system.

TABLE 1

Binding and activation of CHO-K1 cells expressing FPRL2, FPRL1 or FPR by F2L, FMLP, WKYMVm (SEQ ID NO: 23), WKYMVM (SEQ ID NO: 21) and SHAAG (Residues 14-18 of SEQ ID NO: 22) were studied using a binding assay, an aequorin-based assay and an assay measuring the inhibition of cAMP accumulation.

| Receptor | Ligand | $pEC_{50}$ (aequorin assay) | $pEC_{50}$ (cAMP assay) | $pIC_{50}$ (binding assay) |
|---|---|---|---|---|
| FPRL2 | F2L | 8.02 ± 0.13 (n = 9) | 8.24 ± 0.06 (n = 4) | 7.48 ± 0.003 (n = 3) |
|  | WKYMVm | <6 | NT | <6 |
|  | WKYMVM | <6 | <6 | NT |
|  | SHAAG | <6 | <6 | <6 |
|  | FMLP | <6 | <6 | <6 |
| FPRL1 | F2L | 6.26 ± 0.12 (n = 3) | 6.65 ± 0.16 (n = 8) | <6 |
|  | WKYMVm | 10.57 ± 0.10 (n = 3) | NT | 7.66 ± 0.15 (n = 3) |
|  | WKYMVM | 10.04 ± 0.18 (n = 3) | 10.27 ± 0.27 (n = 4) | NT |
|  | SHAAG | 9.27 ± 0.06 (n = 3) | 9.23 ± 0.17 (n = 6) | NT |
|  | FMLP | 5.94 ± 0.03 (n = 3) | <6 | NT |
| FPR | F2L | <6 | <6 | <6 |
|  | WKYMVm | 9.18 ± 0.16 (n = 3) | NT | 7.03 ± 0.16 (n = 3) |
|  | WKYMVM | 7.48 ± 0.08 (n = 3) | 8.23 ± 0.13 (n = 4) | NT |
|  | SHAAG | <6 | <6 | NT |
|  | FMLP | 9.39 ± 0.33 (n = 3) | 10.15 ± 0.08 (n = 4) | NT |

The EC50 and IC50 parameters of the dose-response curves were determined by non-linear regression using the Graphpad Prism software. The results represent the mean pEC50 or pIC50 (-Log values of EC50 or IC50 expressed in Mol/L) ± s.e.m. for at least three independent experiments (n). NT: not tested.

Example 9

Anti-FPRL2 Monoclonal Antibodies Modulate the Intracellular Response of Human FPRL2

Aequorine Assays

Functional responses were analyzed by recording the luminescence of aequorine in human FPRL2 and FPRL1 expressing cells following the addition of agonists or purified monoclonal antibodies.

In brief, cells were collected from plates with PBS containing 5 mM EDTA, pelleted, resuspened at $5 \times 10^6$ cells /ml in DMEM/F-12 medium containing 0.1% bovine serum albumin, incubated with 5 μM coelenterazine H (molecular probes, Inc. Eugene, Oreg.) for 4 h at room temperature and diluted in DMEM/F-12 medium at a concentration of $5 \times 10^5$ cells/ml. Cells where then mixed in an 96 wells plate with the ligands or purified monoclonal antibodies. The light emission was recorded over 60 sec using a microlumat Luminometer (EG&G Berthold, microplate luminometer LB 96V).

Experimental Design

Reagents, Ligands and Monoclonal Antibodies (Modulators) Used in Assays.

Aequorine medium (base line of expressing cells).
ATP 20 μM and triton 0.1% (maximum light emission in cells).
F2L peptide (SEQ ID NO 18), specific ligand of human FPRL2 receptor as described in (Migeotte et al. (2005) J. Exp. Med, 201: 83-93). Two different batches F2L (1) and F2L (2) have been used.
Humanin (HN (N)) peptide (Phoenix Pharmaceuticals, Inc.) as described in (Masataka et al. (2004) Biochemical and Biophysical Research Communications, 324: 255-261). This peptide is disclosed as a ligand for FPRL2 and FPRL1.
Purified monoclonal antibodies (Mab):
  1. FPRL2 145C 4F2 1C4
  2. FPRL2 422F 2B9 1C11
  3. FPRL2 422F 2G3 1A10
  4. unrelated antibody which does not bind to FPRL2 (Control Mab)

Antibodies were purified with protein A sepharose 4B beads according to Amersham protocol (Amersham Pharmacia Biotech, Uppsala, Sweden). Antibodies FPRL2 145C 4F2 1C4, FPRL2 422F 2B9 1C11 and FPRL2 422F 2G3 1A10 have been deposited with the BCCM/LMBP Plasmid collection, Department of Molecular Biology, Gent University, Technologiepark 927, B-9052, Gent-Zwijnaarde, Belgium, under the Budapest treaty. They have the provisional accession numbers LMBP 6404CB (FPRL2 145C 4F2 1C4), LMBP 6405CB (FPRL2 422F 2B9 1C11), and LMBP 6406CB (FPRL2 422F 2G3 1A10). The dates of deposition are Apr. 21, 2005 (LMBP 6404CB/FPRL2 145C 4F2 1C4), and Apr. 28, 2005 (LMBP 6405CB/FPRL2 422F 2B9 1C11, and LMBP 6406CB/FPRL2 422F 2G3 1A10).

Reagents, peptidic ligands and monoclonal antibodies have been used at different concentrations in assays as indicated in Tables 2 and 3. Each data point is in duplicate. F2L and Humanin peptides were used at concentrations from 2.5 μM to 0.4 nM and Mab at concentrations from 500 ug/ml to 5 ug/ml. Human FPRL1 expressing cells were used as negative control to Mab. Functionality of these cells has been control with Humanin.

TABLE 2

96 wells plate scheme in an aequorine assay using human FPRL2 expressing cells.

| | 1 | 2 | 3 | 4 | 5 | 6 | 7 | 8 | 9 | 10 | 11 | 12 |
|---|---|---|---|---|---|---|---|---|---|---|---|---|
| A | Medium | | ATP 20 μM | | Triton 0.1% | | | | | | | |
| B | F2L (1) $2.5 \times 10^{-6}$M | | F2L (1) $8.3 \times 10^{-7}$M | | F2L (1) $2.8 \times 10^{-7}$M | | F2L (1) $9.3 \times 10^{-8}$M | | F2L (1) $3.1 \times 10^{-8}$M | | F2L (1) $1 \times 10^{-8}$M | |
| C | F2L (1) $3.4 \times 10^{-9}$M | | F2L (1) $1.1 \times 10^{-9}$M | | F2L (1) $4 \times 10^{-10}$M | | F2L (2) $2.5 \times 10^{-6}$M | | F2L (2) $8.3 \times 10^{-7}$M | | F2L (2) $2.8 \times 10^{-7}$M | |
| D | F2L (2) $9.3 \times 10^{-8}$M | | F2L (2) $3.1 \times 10^{-8}$M | | F2L (2) $1 \times 10^{-8}$M | | F2L (2) $3.4 \times 10^{-9}$M | | F2L (2) $1.1 \times 10^{-9}$M | | F2L (2) $4 \times 10^{-10}$M | |
| E | Humanin $2.5 \times 10^{-6}$M | | Humanin $8.3 \times 10^{-7}$M | | Humanin $2.8 \times 10^{-7}$M | | Humanin $9.3 \times 10^{-8}$M | | Humanin $3.1 \times 10^{-8}$M | | Humanin $1 \times 10^{-8}$M | |
| F | Humanin $3.4 \times 10^{-9}$M | | Humanin $1.1 \times 10^{-9}$M | | Humanin $4 \times 10^{-10}$M | | Control Mab 500 ug/ml | | Control Mab 100 ug/ml | | Control Mab 20 ug/ml | |
| G | M1 | M1 | M1 | M1 | M2 | M2 | M2 | M2 | M3 | M3 | M3 | M3 |
| H | 500 ug/ml | 100 ug/ml | 20 ug/ml | 5 ug/ml | 300 ug/ml | 100 ug/ml | 20 ug/ml | 5 ug/ml | 500 ug/ml | 100 ug/ml | 20 ug/ml | 5 ug/ml |

M1 = mAb FPRL2 145C 4F2 1C4,
M2 = mAb FPRL2 422F 2B9 1C11,
M3 = mAb FPRL2 422F 2G3 1A10.

TABLE 3

96 wells plate scheme in an aequorine assay using human FPRL1 expressing cells.

| | 1 | 2 | 3 | 4 | 5 | 6 | 7 | 8 | 9 | 10 | 11 | 12 |
|---|---|---|---|---|---|---|---|---|---|---|---|---|
| A | Medium | | ATP 20 μM | | Triton 0.1% | | | | | | | |
| B | Humanin $2.5 \times 10^{-6}$M | | Humanin $8.3 \times 10^{-7}$M | | Humanin $2.8 \times 10^{-7}$M | | Humanin $9.3 \times 10^{-8}$M | | Humanin $3.1 \times 10^{-8}$M | | Humanin $1 \times 10^{-8}$M | |
| C | Humanin $3.4 \times 10^{-9}$M | | Humanin $1.1 \times 10^{-9}$M | | Humanin $4 \times 10^{-10}$M | | Control Mab 500 ug/ml | | Control Mab 100 ug/ml | | Control Mab 20 ug/ml | |
| D | M1 | M1 | M1 | M1 | M2 | M2 | M2 | M2 | M3 | M3 | M3 | M3 |
| E | 500 ug/ml | 100 ug/ml | 20 ug/ml | 5 ug/ml | 300 ug/ml | 100 ug/ml | 20 ug/ml | 5 ug/ml | 500 ug/ml | 100 ug/ml | 20 ug/ml | 5 ug/ml |

M1 = mAb FPRL2 145C 4F2 1C4,
M2 = mAb FPRL2 422F 2B9 1C11,
M3 = mAb FPRL2 422F 2G3 1A10.

Results

The charts in FIGS. 14 and 15 depict the results expressed in RLU corresponding to the 96-well plates indicated in Table 2.

Observations

F2L peptides activates human FPRL2 expressing cells (B1-D6) and Humanin activates both human FPRL1 (data not shown) and FPRL2 expressing cells (E1-F6) demonstrating the functionality of cells. Mab FPRL2 422F 2B9 1C11 (G5-G8 and H5-H8) is clearly able to activate human FPRL2 expressing cells in a dose dependent manner. Mab FPRL2 422F 2G3 1A10 (G9-G12 and H9-H12) is also able to active these cells but to a lesser extent. The control Mab (F7-F12) does not activate FPRL2 expressing cells. No activation on human FPRL1 expressing cells has been observed with the Mab panel tested (data not shown).

The above-mentioned observations indicate that Mab FPRL2 422F 2B9 1C11 and Mab 422F 2G3 1A10 are able to induce a FPRL2 functional response. These two monoclonal antibodies bind to and activate (as agonist) the FPRL2 receptor.

REFERENCES

1. Abbrachio, M. P. and Bumstock, G. (1994) Pharmacol. Ther. 64, 445-475.
2. Fredhohn, B. B. et al.(1997) Trends Pharmacol. Sci. 18, 79-82.
3. Webb, T. E. et al. (1993) FEBS Lett. 324, 219-225.
4. Léon, C. et al. (1997) FEBS Lett. 403, 26-30.
5. Communi, D. et al. (1997) J. Biol. Chem. 272, 31969-31973.
6. Lustig, K. D. et al. (1993) Proc. Natl. Acad. Sci. U.S.A. 90, 5113-5117.
7. Parr, C. E. et al. (1994) Proc. Natl. Acad. Sci. U.S.A. 91, 3275-3279.
8. Bogdanov, Y. et al. (1997) J. Biol. Chem. 272, 12583-12590.
9. Boyer, J. L. et al. (2000) Mol. Pharmacol. 57, 805-810.
10. Webb, T. E. et al. (1996) Mol. Pharmacol. 50, 258-265.
11. Chang, K. et al. (1995) J. Biol. Chem. 270, 26152-26158.
12. Communi, D. et al. (1996) Biochem. Biophys. Res. Commun. 222, 303-308.
13. Nicholas, R. A. et al. (1996) Mol. Pharmacol. 50, 224-229.
14. Communi, D. et al. (1995) J. Biol. Chem. 270, 30849-30852.
15. Nguyen, T. et al. (1995) J. Biol. Chem. 270, 30845-30848.
16. Webb, T. E. et al. (1996) Biochem. Biophys. Res. Commun. 219, 105-110.
17. Akbar, G. K. M. et al. (1996) J. Biol. Chem. 271, 18363-18367.
18. Yokomizo, T. et al. (1997) Nature 387, 620-624.
19. Li, Q. et al. (1997) Biochem. Biophys. Res. Commun. 236, 455-460.
20. Janssens, R. et al. (1997) Biochem. Biophys. Res. Commun. 226, 106-112.
21. Zhang, F. L et al. (2001) J. Biol. Chem. 276 (11), 8608-8615.
22. Hollopeter, G. et al. (2001) Nature 409, 202-207.
23. Chambers, J. K. et al. (2000) J. Biol. Chem. 275 (15), 10767-10771.
24. Wittenberger, T. et al. (2001) J. Mol. Biol. 307, 799-813.
25. Communi, D. et al. (1995b). Circ. Res., 76, 191-198.
26. Brooker, G. et al. (1979) Adv. Cyclic Nucleotide Res. 10, 1-33.
27. Minamide, L. S. and Bamburg, J. R. (1990) Anal. Biochem. 190, 66-70.
28. Erb, L. et al. (1995) J. Biol. Chem. 270, 4185-4188.
29. Baltensperger, K. and Porzig, H. (1997) J. Biol. Chem. 272, 10151-10159.
30. Eason, M. G. et al. (1992) J. Biol. Chem. 267 (22), 15795-15801.
31. Chabre, O. et al. (1994) J. Biol. Chem. 269 (8), 5730-5734.
32. Boyer, J. L. et al. (1993) J. Pharmacol. Exp. Ther. 267, 1140-1146.
33. Simon, J. et al. (2001) Br. J. Pharmacol. 132, 173-182.
34. Gudermann et al. (1995) J. Mol. Med. 73, 51-63.
35. Lundquist F. (1960) Acta Physiol. Scand. 175, 97
36. Bergman E. (1990) Physiol. Rev. 70, 567-590
37. Cummings J. H., et al. (1987) Gut 28:1221-7μ
38. Mirzabekov et al. (2000) Nature Biotechnology 18, 649-654
39. Ernst, S., C. Lange, A. Wilbers, V. Goebeler, V. Gerke, and U. Rescher. 2004, *J. Immunol.* 172:7669-7676.
40. Christophe, T., A. Karlsson, C. Dugave, M. J. Rabiet, F. Boulay, and C. Dahlgren. 2001. *J. Biol. Chem.* 276:21585-21593.
41. Yang, D., Q. Chen, B. Gertz, R. He, M. Phulsuksombati, R. D. Ye, and J. J. Oppenheim. 2002. *J. Leukoc. Biol.* 72:598-607.
42. Stables, J., A. Green, F. Marshall, N. Fraser, E. Knight, M. Sautel, G. Milligan, M. Lee, and S. Rees. 1997. *Anal. Biochem.* 252:115-126.
43. Gourlet, P., J. Rathe, P. De Neef, J. Cnudde, M. C. Vandermeers-Piret, M. Waelbroeck, and P. Robberecht. 1998. *Eur. J. Pharmacol.* 354:105-111.
44. Migeotte, I., J. D. Franssen, S. Goriely, F. Willems, and M. Parmentier. 2002. *Eur. J. Immunol.* 32:494-501.
45. Costagliola, S., P. Rodien, M. C. Many, M. Ludgate, and G. Vassart. 1998. *J. Immunol.* 160:1458-1465.
46. Kotani, M., M. Detheux, A. Vandenbogaerde, D. Communi, J. M. Vanderwinden, E. Le Poul, S. Brezillon, R. Tyldesley, N. Suarez-Huerta, F. Vandeput, C. Blanpain, S. N. Schiffmann, G. Vassart, and M. Parmentier. 2001. *J. Biol. Chem.* 276:34631-34636.
47. Taketani, S., Y. Adachi, H. Kohno, S. Ikehara, R. Tokunaga, and T. Ishii. 1998. *J. Biol. Chem.* 273:31388-31394.
48. Wittamer, V., J. D. Franssen, M. Vulcano, J. F. Mirjolet, E. Le Poul, I. Migeotte, S. Brezillon, R. Tyldesley, C. Blanpain, M. Detheux, A. Mantovani, S. Sozzani, G. Vassart, M. Parmentier, and D. Communi. 2003. *J. Exp. Med.* 198:977-985.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed is:

1. An isolated nucleic acid molecule encoding a heme binding protein (HBP) polypeptide consisting essentially of the amino acid sequence represented by SEQ ID NO:18 or SEQ ID NO:19, wherein said polypeptide specifically binds FPRL2 having the amino acid sequence represented by SEQ ID NO: 2.

* * * * *

SEQUENCE LISTING

<160> NUMBER OF SEQ ID NOS: 37

<210> SEQ ID NO 1
<211> LENGTH: 1062
<212> TYPE: DNA
<213> ORGANISM: Homo sapiens

<400> SEQUENCE: 1

```
atggaaacca acttctccat tcctctgaat gaaactgagg aggtgctccc tgagcctgct      60
ggccacaccg ttctgtggat cttctcattg ctagtccacg gagtcacctt tgtcttcggg     120
gtcctgggca atgggcttgt gatctgggtg ctggattcc ggatgacacg cacagtcaac      180
accatctgtt acctgaacct ggccctagct gacttctctt tcagtgccat cctaccattc     240
cgaatggtct cagtcgccat gagagaaaaa tggcctttg gctcattcct atgtaagtta      300
gttcatgtta tgatagacat caacctgttt gtcagtgtct acctgatcac catcattgct     360
ctggaccgct gtatttgtgt cctgcatcca gcctgggccc agaaccatcg caccatgagt     420
ctggccaaga gggtgatgac gggactctgg attttcacca tagtccttac cttaccaaat     480
ttcatcttct ggactacaat aagtactacg aatggggaca catactgtat tttcaacttt     540
gcattctggg gtgacactgc tgtagagagg ttgaacgtgt tcattaccat ggccaaggtc     600
tttctgatcc tccacttcat tattggcttc agcgtgccta tgtccatcat cacagtctgc     660
tatgggatca tcgctgccaa aattcacaga aaccacatga ttaaatccag ccgtccctta     720
cgtgtcttcg ctgctgtggt ggcttctttc ttcatctgtt ggttccctta tgaactaatt     780
ggcattctaa tggcagtctg gctcaaagag atgttgttaa atggcaaata caaaatcatt     840
cttgtcctga ttaacccaac aagctccttg gcctttttta acagctgcct caacccaatt     900
ctctacgtct ttatgggtcg taacttccaa gaaagactga ttcgctcttt gcccactagt     960
ttggagaggg ccctgactga ggtccctgac tcagcccaga ccagcaacac agacaccact    1020
tctgcttcac ctcctgagga gacggagtta caagcaatgt ga                       1062
```

<210> SEQ ID NO 2
<211> LENGTH: 353
<212> TYPE: PRT
<213> ORGANISM: Homo sapiens

<400> SEQUENCE: 2

Met Glu Thr Asn Phe Ser Ile Pro Leu Asn Glu Thr Glu Glu Val Leu
 1               5                  10                  15

Pro Glu Pro Ala Gly His Thr Val Leu Trp Ile Phe Ser Leu Leu Val
            20                  25                  30

His Gly Val Thr Phe Val Phe Gly Val Leu Gly Asn Gly Leu Val Ile
        35                  40                  45

Trp Val Ala Gly Phe Arg Met Thr Arg Thr Val Asn Thr Ile Cys Tyr
    50                  55                  60

Leu Asn Leu Ala Leu Ala Asp Phe Ser Phe Ser Ala Ile Leu Pro Phe
65                  70                  75                  80

Arg Met Val Ser Val Ala Met Arg Glu Lys Trp Pro Phe Gly Ser Phe
                85                  90                  95

Leu Cys Lys Leu Val His Val Met Ile Asp Ile Asn Leu Phe Val Ser
            100                 105                 110

Val Tyr Leu Ile Thr Ile Ile Ala Leu Asp Arg Cys Ile Cys Val Leu
        115                 120                 125

His Pro Ala Trp Ala Gln Asn His Arg Thr Met Ser Leu Ala Lys Arg
    130                 135                 140

Val Met Thr Gly Leu Trp Ile Phe Thr Ile Val Leu Thr Leu Pro Asn
145                 150                 155                 160

Phe Ile Phe Trp Thr Thr Ile Ser Thr Thr Asn Gly Asp Thr Tyr Cys
                165                 170                 175

Ile Phe Asn Phe Ala Phe Trp Gly Asp Thr Ala Val Glu Arg Leu Asn
            180                 185                 190

Val Phe Ile Thr Met Ala Lys Val Phe Leu Ile Leu His Phe Ile Ile
        195                 200                 205

Gly Phe Ser Val Pro Met Ser Ile Ile Thr Val Cys Tyr Gly Ile Ile
    210                 215                 220

Ala Ala Lys Ile His Arg Asn His Met Ile Lys Ser Ser Arg Pro Leu
225                 230                 235                 240

Arg Val Phe Ala Ala Val Val Ala Ser Phe Phe Ile Cys Trp Phe Pro
                245                 250                 255

Tyr Glu Leu Ile Gly Ile Leu Met Ala Val Trp Leu Lys Glu Met Leu
            260                 265                 270

Leu Asn Gly Lys Tyr Lys Ile Ile Leu Val Leu Ile Asn Pro Thr Ser
        275                 280                 285

Ser Leu Ala Phe Phe Asn Ser Cys Leu Asn Pro Ile Leu Tyr Val Phe
    290                 295                 300

Met Gly Arg Asn Phe Gln Glu Arg Leu Ile Arg Ser Leu Pro Thr Ser
305                 310                 315                 320

Leu Glu Arg Ala Leu Thr Glu Val Pro Asp Ser Ala Gln Thr Ser Asn
                325                 330                 335

Thr Asp Thr Thr Ser Ala Ser Pro Pro Glu Glu Thr Glu Leu Gln Ala
            340                 345                 350

Met

<210> SEQ ID NO 3
<211> LENGTH: 1053
<212> TYPE: DNA
<213> ORGANISM: Homo sapiens

<400> SEQUENCE: 3
atggagacaa attcctctct ccccacgaac atctctggag ggacacctgc tgtatctgct      60
ggctatctct tcctggatat catcacttat ctggtatttg cagtcacctt gtcctcgggg     120
gtcctgggca acgggcttgt gatctgggtg ctggattcc ggatgacaca cacagtcacc     180
accatcagtt acctgaacct ggccgtggct gacttctgtt tcacctccac tttgccattc     240
ttcatggtca ggaaggccat ggaggacat ggcctttcg gctggttcct gtgcaaattc      300
ctctttacca gtggacat caacttgttc ggaagtgtct tcctgatcgc cctcattgct      360
ctggaccgct gtgtttgcgt cctgcatcca gtctggaccc agaaccaccg caccgtgagc     420
ctggccaaga ggtgatcat tgggccctgg gtgatggctc tgctcctcac attgccagtt     480
atcattcgtg tgactacagt acctggtaaa acggggacag tagcctgcac tttaactt      540 tcgccctgga ccaacgaccc taaagagagg ataaatgtgg ccgttgccat gttgacggtg     600
agaggcatca tccggttcat cattggcttc agcgcaccca tgtccatcgt tgctgtcagt     660
tatgggctta ttgccaccaa gatcacaag caaggcttga ttaagtccag tcgtcccta      720 cgggtcctct cctttgtcgc agcagccttt tttctctgct ggtccccata tcaggtggtg     780

-continued

```
gcccttatag ccacagtcag aatccgtgag ttattgcaag gcatgtacaa agaaattggt    840
attgcagtgg atgtgacaag tgccctggcc ttcttcaaca gctgcctcaa ccccatgctc    900
tatgtcttca tgggccagga cttccgggag aggctgatcc acgccttcc cgccagtctg     960 gagagggccc tgaccgagga ctcaacccaa accagtgaca cagctaccaa ttctacttta   1020
ccttctgcag aggtggcgtt acaggcaaag tga                                1053
```

<210> SEQ ID NO 4
<211> LENGTH: 350
<212> TYPE: PRT
<213> ORGANISM: Homo sapiens

<400> SEQUENCE: 4

```
Met Glu Thr Asn Ser Ser Leu Pro Thr Asn Ile Ser Gly Gly Thr Pro
  1               5                  10                  15

Ala Val Ser Ala Gly Tyr Leu Phe Leu Asp Ile Ile Thr Tyr Leu Val
             20                  25                  30

Phe Ala Val Thr Phe Val Leu Gly Val Leu Gly Asn Gly Leu Val Ile
         35                  40                  45

Trp Val Ala Gly Phe Arg Met Thr His Thr Val Thr Thr Ile Ser Tyr
     50                  55                  60

Leu Asn Leu Ala Val Ala Asp Phe Cys Phe Thr Ser Thr Leu Pro Phe
 65                  70                  75                  80

Phe Met Val Arg Lys Ala Met Gly Gly His Trp Pro Phe Gly Trp Phe
                 85                  90                  95

Leu Cys Lys Phe Leu Phe Thr Ile Val Asp Ile Asn Leu Phe Gly Ser
            100                 105                 110

Val Phe Leu Ile Ala Leu Ile Ala Leu Asp Arg Cys Val Cys Val Leu
        115                 120                 125

His Pro Val Trp Thr Gln Asn His Arg Thr Val Ser Leu Ala Lys Lys
    130                 135                 140

Val Ile Ile Gly Pro Trp Val Met Ala Leu Leu Leu Thr Leu Pro Val
145                 150                 155                 160

Ile Ile Arg Val Thr Thr Val Pro Gly Lys Thr Gly Thr Val Ala Cys
                165                 170                 175

Thr Phe Asn Phe Ser Pro Trp Thr Asn Asp Pro Lys Glu Arg Ile Asn
            180                 185                 190

Val Ala Val Ala Met Leu Thr Val Arg Gly Ile Ile Arg Phe Ile Ile
        195                 200                 205

Gly Phe Ser Ala Pro Met Ser Ile Val Ala Val Ser Tyr Gly Leu Ile
    210                 215                 220

Ala Thr Lys Ile His Lys Gln Gly Leu Ile Lys Ser Ser Arg Pro Leu
225                 230                 235                 240

Arg Val Leu Ser Phe Val Ala Ala Ala Phe Phe Leu Cys Trp Ser Pro
                245                 250                 255

Tyr Gln Val Val Ala Leu Ile Ala Thr Val Arg Ile Arg Glu Leu Leu
            260                 265                 270

Gln Gly Met Tyr Lys Glu Ile Gly Ile Ala Val Asp Val Thr Ser Ala
        275                 280                 285

Leu Ala Phe Phe Asn Ser Cys Leu Asn Pro Met Leu Tyr Val Phe Met
    290                 295                 300

Gly Gln Asp Phe Arg Glu Arg Leu Ile His Ala Leu Pro Ala Ser Leu
305                 310                 315                 320

Glu Arg Ala Leu Thr Glu Asp Ser Thr Gln Thr Ser Asp Thr Ala Thr
```

```
                          325                 330                 335
Asn Ser Thr Leu Pro Ser Ala Glu Val Ala Leu Gln Ala Lys
            340                 345                 350

<210> SEQ ID NO 5
<211> LENGTH: 1056
<212> TYPE: DNA
<213> ORGANISM: Homo sapiens

<400> SEQUENCE: 5
atggaaacca acttctccac tcctctgaat gaatatgaag aagtgtccta tgagtctgct      60
ggctacactg ttctgcggat cctcccattg gtggtgcttg ggtcacctt tgtcctcggg      120 gtcctgggca atgggcttgt gatctgggtg gctggattcc ggatgacacg cacagtcacc     180
accatctgtt acctgaacct ggccctggct gacttttctt tcacggccac attaccattc    240
ctcattgtct ccatggccat gggagaaaaa tggccttttg ctggttcct gtgtaagtta     300 attcacatcg tggtggacat caacctcttt ggaagtgtct tcttgattgg tttcattgca    360
ctggaccgct gcatttgtgt cctgcatcca gtctgggccc agaaccaccg cactgtgagt    420
ctggccatga aggtgatcgt cggaccttgg attcttgctc tagtccttac cttgccagtt    480
ttcctctttt tgactacagt aactattcca aatggggaca catactgtac tttcaacttt    540
gcatcctggg gtggcacccc tgaggagagg ctgaaggtgg ccattaccat gctgacagcc    600
agagggatta tccggtttgt cattggcttt agcttgccga tgtccattgt tgccatctgc    660
tatgggctca ttgcagccaa gatccacaaa aagggcatga ttaaatccag ccgtcccta    720 cgggtcctca ctgctgtggt ggcttctttc ttcatctgtt ggtttccctt tcaactggtt    780
gcccttctgg gcaccgtctg gctcaaagag atgttgttct atggcaagta caaaatcatt    840
gacatcctgg ttaacccaac gagctccctg gccttcttca acagctgcct caaccccatg    900
ctttacgtct ttgtgggcca agacttccga gagagactga tccactccct gcccaccagt    960
ctggagaggg ccctgtctga ggactcagcc ccaactaatg acacggctgc caattctgct   1020
tcacctcctg cagagactga gttacaggca atgtga                             1056

<210> SEQ ID NO 6
<211> LENGTH: 351
<212> TYPE: PRT
<213> ORGANISM: Homo sapiens

<400> SEQUENCE: 6

Met Glu Thr Asn Phe Ser Thr Pro Leu Asn Glu Tyr Glu Glu Val Ser
 1               5                  10                  15

Tyr Glu Ser Ala Gly Tyr Thr Val Leu Arg Ile Leu Pro Leu Val Val
            20                  25                  30

Leu Gly Val Thr Phe Val Leu Gly Val Leu Gly Asn Gly Leu Val Ile
        35                  40                  45

Trp Val Ala Gly Phe Arg Met Thr Arg Thr Val Thr Thr Ile Cys Tyr
    50                  55                  60

Leu Asn Leu Ala Leu Ala Asp Phe Ser Phe Thr Ala Thr Leu Pro Phe
65                  70                  75                  80

Leu Ile Val Ser Met Ala Met Gly Glu Lys Trp Pro Phe Gly Trp Phe
                85                  90                  95

Leu Cys Lys Leu Ile His Ile Val Val Asp Ile Asn Leu Phe Gly Ser
            100                 105                 110

Val Phe Leu Ile Gly Phe Ile Ala Leu Asp Arg Cys Ile Cys Val Leu
```

```
              115                 120                 125
His Pro Val Trp Ala Gln Asn His Arg Thr Val Ser Leu Ala Met Lys
            130                 135                 140

Val Ile Val Gly Pro Trp Ile Leu Ala Leu Val Leu Thr Leu Pro Val
145                 150                 155                 160

Phe Leu Phe Leu Thr Thr Val Thr Ile Pro Asn Gly Asp Thr Tyr Cys
                165                 170                 175

Thr Phe Asn Phe Ala Ser Trp Gly Gly Thr Pro Glu Glu Arg Leu Lys
            180                 185                 190

Val Ala Ile Thr Met Leu Thr Ala Arg Gly Ile Ile Arg Phe Val Ile
            195                 200                 205

Gly Phe Ser Leu Pro Met Ser Ile Val Ala Ile Cys Tyr Gly Leu Ile
        210                 215                 220

Ala Ala Lys Ile His Lys Lys Gly Met Ile Lys Ser Ser Arg Pro Leu
225                 230                 235                 240

Arg Val Leu Thr Ala Val Val Ala Ser Phe Phe Ile Cys Trp Phe Pro
                245                 250                 255

Phe Gln Leu Val Ala Leu Leu Gly Thr Val Trp Leu Lys Glu Met Leu
            260                 265                 270

Phe Tyr Gly Lys Tyr Lys Ile Ile Asp Ile Leu Val Asn Pro Thr Ser
        275                 280                 285

Ser Leu Ala Phe Phe Asn Ser Cys Leu Asn Pro Met Leu Tyr Val Phe
        290                 295                 300

Val Gly Gln Asp Phe Arg Glu Arg Leu Ile His Ser Leu Pro Thr Ser
305                 310                 315                 320

Leu Glu Arg Ala Leu Ser Glu Asp Ser Ala Pro Thr Asn Asp Thr Ala
                325                 330                 335

Ala Asn Ser Ala Ser Pro Pro Ala Glu Thr Glu Leu Gln Ala Met
            340                 345                 350

<210> SEQ ID NO 7
<211> LENGTH: 570
<212> TYPE: DNA
<213> ORGANISM: Homo sapiens

<400> SEQUENCE: 7
atgttgggca tgatcaagaa ctcgctgttc ggaagcgtag agacgtggcc ttggcaggtc      60
ctaagcaaag gggacaagga agaagttgcc tatgaagaaa gggcctgtga aggcggcaaa     120
tttgccacag tagaagtgac agataagcct gtggatgagc tctacgggaa gcaatgccc     180 aaggtcgcaa agtatgcggg gggcaccaat gacaagggaa ttgggatggg gatgacagtc     240
cctatttcct ttgctgtgtt ccccaatgaa gatggctctc tgcagaagaa attaaaagtc     300
tggttccgga ttccaaacca atttcaaagc gacccaccag ctcccagtga caaaagcgtt     360
aagattgagg aacgggaagg catcactgtc tattccatgc agtttggtgg ttatgccaag     420
gaagcagact acgtagcaca agccacccgt ctgcgtgctg ccctggaggg cacagccacc     480
taccgggggg acatctactt ctgcacgggt tatgaccctc ccatgaagcc ctacggacgg     540
cgcaatgaga tctggctgtt gaagacatga                                      570

<210> SEQ ID NO 8
<211> LENGTH: 189
<212> TYPE: PRT
<213> ORGANISM: Homo sapiens

<400> SEQUENCE: 8
```

Met Leu Gly Met Ile Lys Asn Ser Leu Phe Gly Ser Val Glu Thr Trp
1               5                   10                  15

Pro Trp Gln Val Leu Ser Lys Gly Asp Lys Glu Val Ala Tyr Glu
            20                  25                  30

Glu Arg Ala Cys Glu Gly Gly Lys Phe Ala Thr Val Glu Val Thr Asp
                35                  40                  45

Lys Pro Val Asp Glu Ala Leu Arg Glu Ala Met Pro Lys Val Ala Lys
        50                  55                  60

Tyr Ala Gly Gly Thr Asn Asp Lys Gly Ile Gly Met Gly Met Thr Val
65                  70                  75                  80

Pro Ile Ser Phe Ala Val Phe Pro Asn Glu Asp Gly Ser Leu Gln Lys
                85                  90                  95

Lys Leu Lys Val Trp Phe Arg Ile Pro Asn Gln Phe Gln Ser Asp Pro
            100                 105                 110

Pro Ala Pro Ser Asp Lys Ser Val Lys Ile Glu Glu Arg Glu Gly Ile
        115                 120                 125

Thr Val Tyr Ser Met Gln Phe Gly Gly Tyr Ala Lys Glu Ala Asp Tyr
    130                 135                 140

Val Ala Gln Ala Thr Arg Leu Arg Ala Ala Leu Glu Gly Thr Ala Thr
145                 150                 155                 160

Tyr Arg Gly Asp Ile Tyr Phe Cys Thr Gly Tyr Asp Pro Pro Met Lys
                165                 170                 175

Pro Tyr Gly Arg Arg Asn Glu Ile Trp Leu Leu Lys Thr
            180                 185

<210> SEQ ID NO 9
<211> LENGTH: 573
<212> TYPE: DNA
<213> ORGANISM: Mus musculus

<400> SEQUENCE: 9
atgttgggca tgatcaggaa ctcactgttc gggagcgtgg aaacgtggcc ttggcaggtt      60
ctaagcaccg ggggcaagga agatgtctcc tatgaggaaa gagcctgtga aggggggcaag    120
tttgctactg tggaagtgac agacaagcca gtggatgagg ctctccggga agcgatgccc    180
aagatcatga gtatgtgggt ggcaccaat gacaaaggag tcggcatggg tatgacagtc    240
cctgtctctt ttgccgtgtt tcccaatgaa gatggctccc tacagaagaa actgaaagtc    300
tggttccgga ttccgaacca atttcaaggc agcccaccgg cccccagtga tgagagtgtg    360
aagatcgagg aacgggaggg catcactgtc tattccacgc aatttggagg ctatgccaag    420
gaagcagact atgttgctca tgccacccag ctacggacca cactggaggg cacaccagcg    480
acctaccagg gtgatgtcta ttactgtgcc ggatatgacc ctcccatgaa gccctatgga    540
cgccgtaacg aggtctggct tgtgaaggca tga                                 573

<210> SEQ ID NO 10
<211> LENGTH: 190
<212> TYPE: PRT
<213> ORGANISM: Mus musculus

<400> SEQUENCE: 10

Met Leu Gly Met Ile Arg Asn Ser Leu Phe Gly Ser Val Glu Thr Trp
1               5                   10                  15

Pro Trp Gln Val Leu Ser Thr Gly Gly Lys Glu Asp Val Ser Tyr Glu
            20                  25                  30

```
Glu Arg Ala Cys Glu Gly Gly Lys Phe Ala Thr Val Glu Val Thr Asp
         35                  40                  45

Lys Pro Val Asp Glu Ala Leu Arg Glu Ala Met Pro Lys Ile Met Lys
     50                  55                  60

Tyr Val Gly Gly Thr Asn Asp Lys Gly Val Gly Met Gly Met Thr Val
 65                  70                  75                  80

Pro Val Ser Phe Ala Val Phe Pro Asn Glu Asp Gly Ser Leu Gln Lys
                 85                  90                  95

Lys Leu Lys Val Trp Phe Arg Ile Pro Asn Gln Phe Gln Gly Ser Pro
             100                 105                 110

Pro Ala Pro Ser Asp Glu Ser Val Lys Ile Glu Arg Glu Gly Ile
         115                 120                 125

Thr Val Tyr Ser Thr Gln Phe Gly Gly Tyr Ala Lys Glu Ala Asp Tyr
     130                 135                 140

Val Ala His Ala Thr Gln Leu Arg Thr Thr Leu Glu Gly Thr Pro Ala
145                 150                 155                 160

Thr Tyr Gln Gly Asp Val Tyr Cys Ala Gly Tyr Asp Pro Pro Met
                 165                 170                 175

Lys Pro Tyr Gly Arg Arg Asn Glu Val Trp Leu Val Lys Ala
             180                 185                 190

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<223> OTHER INFORMATION: C-term amidated

<400> SEQUENCE: 11

Phe Lys Lys Ser Phe Lys Leu
 1               5

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Arg Leu Ile Glu Asp Ala Glu Tyr Ala Ala Arg Gly
 1               5                  10

<210> SEQ ID NO 13
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ggggactttc c                                                          11

<210> SEQ ID NO 14
<211> LENGTH: 31
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 14
accggaattc accatggaaa ccaacttctc c                                    31

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
atcatctaga acgcagggta gaaagagaca g                                    31

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cgcacagtca acaccatctg                                                 20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
agctgttaaa aaaggccaag                                                 20

<210> SEQ ID NO 18
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated

<400> SEQUENCE: 18

Met Leu Gly Met Ile Lys Asn Ser Leu Phe Gly Ser Val Glu Thr Trp
 1               5                  10                  15

Pro Trp Gln Val Leu
            20

<210> SEQ ID NO 19
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Met Leu Gly Met Ile Lys Asn Ser Leu Phe Gly Ser Val Glu Thr Trp
```

```
                1               5                  10                 15
Pro Trp Gln Val Leu
                20

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asn Ser Leu Phe Gly Ser Val Glu Thr Trp Pro Trp Gln Val Leu
 1               5                  10                 15

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Trp Lys Tyr Met Val Met
 1               5

<210> SEQ ID NO 22
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Met Leu Trp Arg Arg Lys Ile Gly Pro Gln Met Thr Leu Ser His Ala
 1               5                  10                 15
Ala Gly

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: D-Met

<400> SEQUENCE: 23

Trp Lys Tyr Met Val Met
 1               5

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ctggccacac cgttctgt                                                   18
```

-continued

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ggccatggta atgaacacgt t                                          21

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ttaccatggc caaggtcttt ct                                         22

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gcagactgtg atgatggaca tagg                                       24

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
tcctccactt cattattggc ttcagcgt                                   28

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gaaggtgaag gtcggagtc                                             19

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gaagatggtg atgggatttc                                            20

```
<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
caagcttccc gttctcagcc                                                    20

<210> SEQ ID NO 32
<211> LENGTH: 1119
<212> TYPE: DNA
<213> ORGANISM: Homo sapiens
<220> FEATURE:
<221> NAME/KEY: CDS
<222> LOCATION: (10)..(1068)

<400> SEQUENCE: 32 gaattcacc atg gaa acc aac ttc tcc att cct ctg aat gaa act gag gag        51
           Met Glu Thr Asn Phe Ser Ile Pro Leu Asn Glu Thr Glu Glu
             1               5                  10 gtg ctc cct gag cct gct ggc cac acc gtt ctg tgg atc ttc tca ttg          99
Val Leu Pro Glu Pro Ala Gly His Thr Val Leu Trp Ile Phe Ser Leu
 15                  20                  25                  30 cta gtc cac gga gtc acc ttt gtc ttc ggg gtc ctg ggc aat ggg ctt         147
Leu Val His Gly Val Thr Phe Val Phe Gly Val Leu Gly Asn Gly Leu
                 35                  40                  45 gtg atc tgg gtg gct gga ttc cgg atg aca cgc aca gtc aac acc atc         195
Val Ile Trp Val Ala Gly Phe Arg Met Thr Arg Thr Val Asn Thr Ile
             50                  55                  60 tgt tac ctg aac ctg gcc cta gct gac ttc tct ttc agt gcc atc cta         243
Cys Tyr Leu Asn Leu Ala Leu Ala Asp Phe Ser Phe Ser Ala Ile Leu
 65                  70                  75 cca ttc cga atg gtc tca gtc gcc atg aga gaa aaa tgg cct ttt ggc         291
Pro Phe Arg Met Val Ser Val Ala Met Arg Glu Lys Trp Pro Phe Gly
                 80                  85                  90 tca ttc cta tgt aag tta gtt cat gtt atg ata gac atc aac ctg ttt         339
Ser Phe Leu Cys Lys Leu Val His Val Met Ile Asp Ile Asn Leu Phe
 95                 100                 105                 110 gtc agt gtc tac ctg atc acc atc att gct ctg gac cgc tgt att tgt         387
Val Ser Val Tyr Leu Ile Thr Ile Ile Ala Leu Asp Arg Cys Ile Cys
                115                 120                 125 gtc ctg cat cca gcc tgg gcc cag aac cat cgc acc atg agt ctg gcc         435
Val Leu His Pro Ala Trp Ala Gln Asn His Arg Thr Met Ser Leu Ala
            130                 135                 140 aag agg gtg atg acg gga ctc tgg att ttc acc ata gtc ctt acc tta         483
Lys Arg Val Met Thr Gly Leu Trp Ile Phe Thr Ile Val Leu Thr Leu
145                 150                 155 cca aat ttc atc ttc tgg act aca ata agt act acg aat ggg gac aca         531
Pro Asn Phe Ile Phe Trp Thr Thr Ile Ser Thr Thr Asn Gly Asp Thr
                160                 165                 170 tac tgt att ttc aac ttt gca ttc tgg ggt gac act gct gta gag agg         579
Tyr Cys Ile Phe Asn Phe Ala Phe Trp Gly Asp Thr Ala Val Glu Arg
175                 180                 185                 190 ttg aac gtg ttc att acc atg gcc aag gtc ttt ctg atc ctc cac ttc         627
Leu Asn Val Phe Ile Thr Met Ala Lys Val Phe Leu Ile Leu His Phe
                195                 200                 205 att att ggc ttc agc gtg cct atg tcc atc atc aca gtc tgc tat ggg         675
Ile Ile Gly Phe Ser Val Pro Met Ser Ile Ile Thr Val Cys Tyr Gly
            210                 215                 220
```

```
atc atc gct gcc aaa att cac aga aac cac atg att aaa tcc agc cgt       723
Ile Ile Ala Ala Lys Ile His Arg Asn His Met Ile Lys Ser Ser Arg
        225                 230                 235 ccc tta cgt gtc ttc gct gct gtg gtg gct tct ttc ttc atc tgt tgg       771
Pro Leu Arg Val Phe Ala Ala Val Val Ala Ser Phe Phe Ile Cys Trp
240                 245                 250 ttc cct tat gaa cta att ggc att cta atg gca gtc tgg ctc aaa gag       819
Phe Pro Tyr Glu Leu Ile Gly Ile Leu Met Ala Val Trp Leu Lys Glu
255                 260                 265                 270 atg ttg tta aat ggc aaa tac aaa atc att ctt gtc ctg att aac cca       867
Met Leu Leu Asn Gly Lys Tyr Lys Ile Ile Leu Val Leu Ile Asn Pro
                275                 280                 285 aca agc tcc ttg gcc ttt ttt aac agc tgc ctc aac cca att ctc tac       915
Thr Ser Ser Leu Ala Phe Phe Asn Ser Cys Leu Asn Pro Ile Leu Tyr
            290                 295                 300 gtc ttt atg ggt cgt aac ttc caa gaa aga ctg att cgc tct ttg ccc       963
Val Phe Met Gly Arg Asn Phe Gln Glu Arg Leu Ile Arg Ser Leu Pro
        305                 310                 315 act agt ttg gag agg gcc ctg act gag gtc cct gac tca gcc cag acc      1011
Thr Ser Leu Glu Arg Ala Leu Thr Glu Val Pro Asp Ser Ala Gln Thr
    320                 325                 330 agc aac aca gac acc act tct gct tca cct cct gag gag acg gag tta      1059
Ser Asn Thr Asp Thr Thr Ser Ala Ser Pro Pro Glu Glu Thr Glu Leu
335                 340                 345                 350 caa gca atg tgaggtcggg gatattttg ggctctgtct ctttctaccc               1108
Gln Ala Met tgcgttctag a                                                          1119

<210> SEQ ID NO 33
<211> LENGTH: 17
<212> TYPE: PRT
<213> ORGANISM: Sus sp.

<400> SEQUENCE: 33

Asn Ser Leu Phe Gly Ser Val Glu Thr Trp Pro Trp Gln Val Leu Ser
1               5                   10                  15

Lys

<210> SEQ ID NO 34
<211> LENGTH: 16
<212> TYPE: PRT
<213> ORGANISM: Sus sp.

<400> SEQUENCE: 34

Phe Ala Thr Val Glu Met Thr Asp Lys Pro Val Asp Glu Ala Leu Arg
1               5                   10                  15

<210> SEQ ID NO 35
<211> LENGTH: 189
<212> TYPE: PRT
<213> ORGANISM: Sus sp.

<400> SEQUENCE: 35

Met Leu Gly Met Ile Arg Asn Ser Leu Phe Gly Ser Val Glu Thr Trp
1               5                   10                  15

Pro Trp Gln Val Leu Ser Lys Gly Asp Lys Gln Asp Ile Ser Tyr Glu
            20                  25                  30

Glu Arg Ala Cys Glu Gly Gly Lys Phe Ala Thr Val Glu Met Thr Asp
        35                  40                  45
```

```
Lys Pro Val Asp Glu Ala Leu Arg Glu Ala Met Pro Lys Val Met Lys
     50                  55                  60

Tyr Val Gly Gly Ser Asn Asp Lys Gly Ile Gly Met Gly Met Thr Val
 65                  70                  75                  80

Pro Ile Ser Phe Ala Val Phe Pro Ser Asp Gly Gly Ser Leu Gln Lys
                 85                  90                  95

Lys Leu Lys Val Trp Phe Arg Ile Pro Asn Glu Phe Gln Ser Asn Pro
             100                 105                 110

Pro Val Pro Ser Asp Asp Ser Ile Lys Ile Glu Glu Arg Glu Ser Ile
             115                 120                 125

Thr Val Tyr Ser Leu Gln Phe Gly Gly Tyr Ala Lys Glu Ala Asp Tyr
             130                 135                 140

Val Ala Arg Ala Ala Gln Leu Arg Thr Ala Leu Glu Gly Ile Ala Thr
145                 150                 155                 160

Cys Arg Ser Asp Val Tyr Phe Cys Thr Gly Tyr Asp Pro Pro Met Lys
                 165                 170                 175

Pro Tyr Gly Arg Arg Asn Glu Val Trp Leu Val Lys Ala
             180                 185

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 36

His His His His His His
 1               5

<210> SEQ ID NO 37
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: May or may not be N-term acetylated

<400> SEQUENCE: 37

Met Leu Gly Met Ile Lys Asn Ser Leu Phe Gly Ser Val Glu Thr Trp
 1               5                  10                  15

Pro Trp Gln Val Leu
             20
```